United States Patent [19]
Bock et al.

[11] Patent Number: 5,686,454
[45] Date of Patent: Nov. 11, 1997

[54] CAMPHORCARBONYL

[75] Inventors: Mark G. Bock, Hatfield; Doug W. Hobbs, Lansdale, both of Pa.

[73] Assignee: Merck & Co., Inc., Rahway, N.J.

[21] Appl. No.: 578,640

[22] PCT Filed: Jul. 11, 1994

[86] PCT No.: PCT/US94/07769

§ 371 Date: Jan. 16, 1996

§ 102(e) Date: Jan. 16, 1996

[87] PCT Pub. No.: WO95/02587

PCT Pub. Date: Jan. 26, 1995

Related U.S. Application Data

[63] Continuation-in-part of Ser. No. 93,502, Jul. 16, 1993, abandoned.

[51] Int. Cl.$^6$ .............. A61K 31/495; C07D 295/185; C07D 403/12; C07D 405/12

[52] U.S. Cl. .......... 514/252; 514/253; 514/254; 514/255; 514/212; 514/226.8; 514/227.2; 514/235.8; 544/230; 544/53; 544/54; 544/121; 544/360; 544/362; 544/364; 544/365; 544/370; 544/372; 544/373; 544/374; 544/379; 544/383; 544/391; 540/598

[58] Field of Search .............. 544/230, 360, 544/362, 364, 365, 370, 372, 373, 374, 379, 383, 384, 385, 391, 53, 54, 121; 540/598; 514/212, 226.8, 227.2, 235.8, 252–255

[56] References Cited

U.S. PATENT DOCUMENTS

| | | | |
|---|---|---|---|
| 4,087,425 | 5/1978 | Garcia et al. | 544/383 |
| 4,147,870 | 4/1979 | Garcia et al. | 544/383 |
| 4,547,505 | 10/1985 | Oepen et al. | 514/255 |
| 5,091,387 | 2/1992 | Evans et al. | 514/278 |
| 5,204,349 | 4/1993 | Bock et al. | 514/253 |
| 5,464,788 | 11/1995 | Bock et al. | 514/252 |

FOREIGN PATENT DOCUMENTS

| | | |
|---|---|---|
| 0 384 843 | 8/1990 | European Pat. Off. |
| 0 450 761 | 10/1991 | European Pat. Off. |
| 0 469 984 A2 | 2/1992 | European Pat. Off. |
| 0 486 280 | 5/1992 | European Pat. Off. |
| 532097 | 3/1993 | European Pat. Off. |
| 533240 | 3/1993 | European Pat. Off. |
| 533241 | 3/1993 | European Pat. Off. |
| 533242 | 3/1993 | European Pat. Off. |
| 2 081 346 | 12/1970 | France. |
| 2 292 477 | 10/1975 | France. |
| WO 94/07496 | 4/1994 | WIPO. |

OTHER PUBLICATIONS

Evans et al, *J. Med. Chem*, 36, pp. 3993–4005 (1993).
Chemical abstracts, vol. 86, No. 5, 31 Jan. 1977, abstract No. 29877c, p. 376, col. R.
Chemical abstracts, vol. 78, No. 5, 5 Feb. 1973, abstract No. 29818u, p. 510, col. L.
J. Pharm. Exp. Ther., vol. 264, No. 1, pp. 308–314, by Pettibone et al., entitled Identification of an Orally Active, Nonpeptidyl Oxytocin Antagonist.
Evans et al., J. Med. Chem., (1993), vol. 36, pp. 3993–4005 Nanomolar-Affinity, Non-Peptide Oxytocin Receptor Antagonists.
Evans et al., J. Med. Chem., (1992), vol. 35, pp. 3919–3927, Orally Active Nonpeptide Oxytocin Antagonists.

*Primary Examiner*—Emily Bernhardt
*Attorney, Agent, or Firm*—Mary A. Appollina; Melvin Winokur

[57] ABSTRACT

The invention is directed to a series of novel compounds of the formula where Y is carbonyl or sulfonyl; $R^7$ and $R^8$ are alkyl, or $R^7$ and $R^8$, together with the carbon to which they are attached, form a $C_{3-6}$ carbocyclic ring; $R^9$ and $R^{10}$ are each independently selected from hydrogen, hydroxyl, oximido, methyl, carboxyl, carboxyalkyl, unsubstituted or substituted alkoxycarbonyl, alkylcarbonyloxyalkyl, cyanoalkyl, hydroxyalkyl or unsubstituted amino; $R^{11}$ is hydrogen, oxo, $-N(R^{12})-CO-R^{13}$ or $-CO-N(R^{14})-R^{15}$; $R^{12}$ is hydrogen or unsubstituted or substituted alkyl; $R^{13}$ is alkoxyl, unsubstituted or substituted heterocyclic rings selected from or unsubstituted or substituted alkyl; and $R^{14}$ and $R^{15}$ are each independently selected from hydrogen or unsubstituted or substituted alkyl. The Y moiety cannot be bonded to the camphor ring at the 3 or 6 positions. Such compounds are oxytocin antagonists useful in the treatment of preterm labor, dysmenorrhea and for the stoppage of labor preparatory to cesarean delivery.

12 Claims, No Drawings

CAMPHORCARBONYL

This application is a 371 of PCT/US94/07769 filed Jul. 11, 1994 which is a continuation-in-part of U.S. application Ser. No. 08/093,502, filed Jul. 16, 1993 (now abandoned).

FIELD OF THE INVENTION

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens. An additional use for the present invention is for the stoppage of labor preparatory to Cesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of the instant invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Cesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

Compounds of the present invention are also inhibitors of vasopressin and can bind to the vasopressin receptor. These compounds are useful in inducing vasodilation, treating hypertension, inducing diuresis and inhibiting platelet agglutination

SUMMARY OF THE INVENTION

The compounds and their pharmaceutically acceptable salts of the present invention are of the general formula

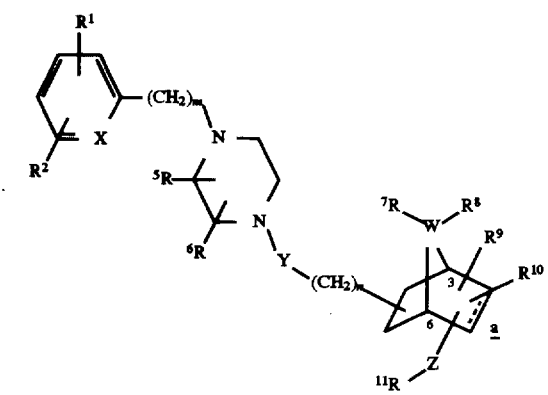

wherein a is a single or double bond;

W is
- (1) C or
- (2) O, provided that when W is O, then $R^7$ and $R^8$ are not present;

X is
- (1) CH or
- (2) N;

Y is
- (1) carbonyl,
- (2) sulfonyl or
- (3) —CONH—;

Z is an optional substituent that, when present, is substituted or unsubstituted alkyl where said substituent is carboxyl;

$R^1$ is
- (1) hydrogen,
- (2) unsubstituted or substituted alkyl where said substituent is halogen,
- (3) halogen or
- (4) alkoxy;

$R^2$ is
- (1) hydrogen,
- (2) unsubstituted or substituted alkyl where said substituent is halogen,
- (3) halogen or
- (4) alkoxy;

$R^5$ and $R^6$ are each independently selected from
- (1) hydrogen,
- (2) alkyl,
- (3) phenylalkyl or
- (4) oxo;

$R^7$ and $R^8$ are each independently selected from
- (1) hydrogen, or
- (2) alkyl, or $R^7$ and $R^8$ together with W, when W is carbon, form a $C_{3-6}$ carbocyclic ring;

$R^9$ and $R^{10}$ are together joined to form cyclic epoxide, whereby the $R^9$ and $R^{10}$ substituents are on the same carbon or on adjacent carbon atoms; or $R^9$ and $R^{10}$ are each independently selected from
- (1) hydrogen,
- (2) hydroxyl,
- (3) halogen,
- (4) oximido,
- (5) methyl,
- (6) carboxyl,
- (7) carboxyalkyl,
- (8) oxo,
- (9) unsubstituted or substituted alkoxycarbonyl where said substituent is selected from pyridyl or piperidinyl,
- (10) alkylcarbonyloxy,
- (11) alkylcarbonyloxyalkyl,
- (12) alkoxycarbonylalkoxy,
- (13) cyanoalkyl,
- (14) hydroxyalkyl,
- (15) trihaloalkylsulfonyloxo, or
- (16) unsubstituted or substituted amino where said substituent is one or more of alkyl, carboxyalkyl or alkoxycarbonylalkyl;

$R^{11}$, which is bonded to substituent Z when Z is present or which is bonded directly to the camphor ring when Z is not present, is
- (1) hydrogen,
- (2) oxo,
- (3) —N($R^{12}$)—CO—$R^{13}$ or
- (4) —CO—N($R^{14}$)—$R^{15}$;

$R^{12}$ is
- (1) hydrogen,
- (2) alkoxy,
- (3) unsubstituted or substituted alkyl where said substituent is one or more of carboxyl, hydroxyl, alkoxyl, alkoxycarbonyl, alkylsulfonyl or arylsulfonyl,
- (4) alkoxycarbonyl or
- (5) alkoxycarbonylamino;

$R^{13}$ is
- (1) hydrogen,
- (2) alkoxyl,
- (3) aralkoxyl,
- (4) carboxyl,
- (5) alkoxycarbonyl,
- (6) alkoxycarbonylamino,
- (7) unsubstituted or substituted cycloalkyl, wherein said substituent is carboxyl,
- (8) unsubstituted or substituted phenyl wherein said substituent is one or more of carboxyl, carboxyalkyl or $SO_3H$,
- (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
- (10) unsubstituted or substituted heterocyclic rings selected from the group consisting of: pyrrolidinyl, tetrahydroimidazolyl, imidazolyl, triazolyl, tetrazolyl, tetrahydrofuranyl, furanyl, dioxolanyl, thienyl, piperidinyl, piperizinyl, pyridinyl, quinuclidinyl, morpholinyl, thiazinyl, azepinyl, tetrahydropyranyl, tetrahydrothiopyranyl, 1-oxotetrahydrothiopyranyl and 1,1-dioxotetrahydrothiopyranyl and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spirodioxolanyl and Het is defined as heterocyclic rings selected from the group consisting of: pyrrolidinyl, tetrahydroimidazolyl, imidazolyl, triazolyl, tetrazolyl, tetrahydrofuranyl, furanyl, dioxolanyl, thienyl, piperidinyl, piperizinyl, pyridinyl, quinuclidinyl, morpholinyl, thiazinyl, azepinyl, tetrahydropyranyl, tetrahydrothiopyranyl, 1-oxotetrahydrothiopyranyl and 1,1-dioxotetrahydrothiopyranyl; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl;

$R^{14}$ and $R^{15}$ are each independently selected from
(1) hydrogen,
(2) unsubstituted or substituted alkyl where said substituent is one or more of hydrogen, carboxyl, amino, dialkylamino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or
(3) unsubstituted or substituted heterocyclic rings selected from the group consisting of: pyrrolidinyl, tetrahydroimidazolyl, imidazolyl, triazolyl, tetrazolyl, tetrahydrofuranyl, furanyl, dioxolanyl, thienyl, piperidinyl, piperizinyl, pyridinyl, quinuclidinyl, morpholinyl, thiazinyl, azepinyl, tetrahydropyranyl, tetrahydrothiopyranyl, 1-oxotetrahydrothiopyranyl and 1,1-dioxotetrahydrothiopyranyl and wherein said substituent is one or more of alkyl, oxo, carboxyl, phenylalkyl, carboxyphenylalkyl or alkoxycarbonyl; and m and n are integers of from 0 to 1;

with the proviso that the bridging methylene moiety —$(CH_2)_n$—, when n is equal to 1, or the moiety Y, when n is equal to 0, shall not be bonded to the camphor ring at either bridgehead position 3 or bridgehead position 6 unless Y is —CONH—.

In one embodiment are the compounds of the formula

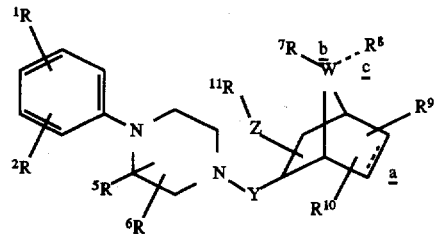

wherein
Y is
(1) carbonyl or
(2) sulfonyl;
$R^7$ and $R^8$ are each independently selected from
(1) alkyl, or
$R^7$ and $R^8$ together with W, when W is carbon, form a $C_{3-6}$ carbocyclic ring;
$R^9$ and $R^{10}$ are each independently selected from
(1) hydrogen,
(2) hydroxyl,
(3) oximido,
(4) methyl,
(5) carboxyl,
(6) carboxyalkyl,
(7) unsubstituted or substituted alkoxycarbonyl where said substituent is selected from pyridyl or piperidinyl,
(8) alkylcarbonyloxy,
(9) alkylcarbonyloxyalkyl,
(10) cyanoalkyl,
(11) hydroxyalkyl or
(12) unsubstituted or substituted amino where said substituent is one or more of alkyl, carboxyalkyl or alkoxycarbonylalkyl; and
$R^{12}$ is
(1) hydrogen or
(2) unsubstituted or substituted alkyl where said substituent is one or more of carboxyl, hydroxyl, alkoxyl, alkoxycarbonyl, alkylsulfonyl or arylsulfonyl.

In a class are the compounds of the formula

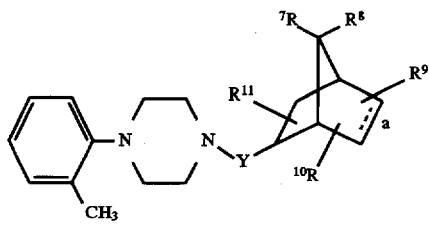

wherein
$R^9$ and $R^{10}$ are each independently selected from
(1) hydrogen,
(2) hydroxyl,
(3) oximido,
(4) methyl,
(5) carboxyl, (6) carboxyalkyl,
(7) unsubstituted or substituted alkoxycarbonyl where said substituent is selected from pyridyl or piperidinyl,
(8) alkylcarbonyloxyalkyl,
(9) cyanoalkyl,
(10) hydroxyalkyl or
(11) unsubstituted amino;

$R^{13}$ is
(1) alkoxyl,
(2) unsubstituted or substituted heterocyclic rings selected from the group consisting of: pyrrolidinyl, tetrahydroimidazolyl, imidazolyl, triazolyl, tetrazolyl, tetrahydrofuranyl, furanyl, dioxolanyl, thienyl, piperidinyl, piperizinyl, pyridinyl, quinuclidinyl, morpholinyl, thiazinyl, azepinyl, tetrahydropyranyl, tetrahydrothiopyranyl, 1-oxotetrahydrothiopyranyl and 1,1-dioxotetrahydrothiopyranyl and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or
(3) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spirodioxolanyl and Het is defined as heterocyclic rings selected from the group consisting of: pyrrolidinyl, tetrahydroimidazolyl, imidazolyl, triazolyl, tetrazolyl, tetrahydrofuranyl, furanyl, dioxolanyl, thienyl, piperidinyl, piperizinyl, pyridinyl, quinuclidinyl, morpholinyl, thiazinyl, azepinyl, tetrahydropyranyl, tetrahydrothiopyranyl, 1-oxotetrahydrothiopyranyl and 1,1-dioxotetrahydrothiopyranyl; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl;

$R^{14}$ and $R^{15}$ are each independently selected from
(1) hydrogen or
(2) unsubstituted or substituted alkyl where said substituent is one or more of hydrogen, carboxyl, amino, dialkylamino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N.

In a subclass are the compounds of the formula

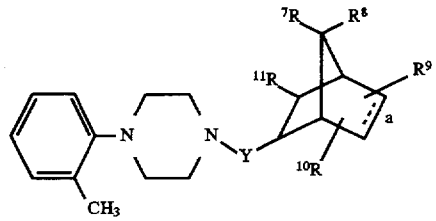

wherein $R^{12}$ is hydrogen; and
$R^{14}$ and $R^{15}$ are each independently selected from
(1) hydrogen or
(2) unsubstituted or substituted alkyl where said substituent is one or more of dialkylamino, hydroxyl, alkylthio or thioalkyl.

Illustrative of the subclass are the compounds wherein
Y is carbonyl;
$R^{11}$ is
(1) —N($R^{12}$)—CO—$R^{13}$ or
(2) —CO—N($R^{14}$)—$R^{15}$; and
$R^{13}$ is
(1) hydrogen,
(2) alkoxyl,
(3) unsubstituted or substituted pyrrolidinyl wherein said substituent is alkoxycarbonylalkyl or
(11) unsubstituted or substituted alkyl, wherein said substituent is one or more of hydroxyl, alkylsulfonyl, imidazolyl, or unsubstituted or substituted amino, wherein said substituent is one or more of tetrahydropyranyl or alkoxycarbonyl.

Further illustrating this subclass are the compounds selected from the group consisting of

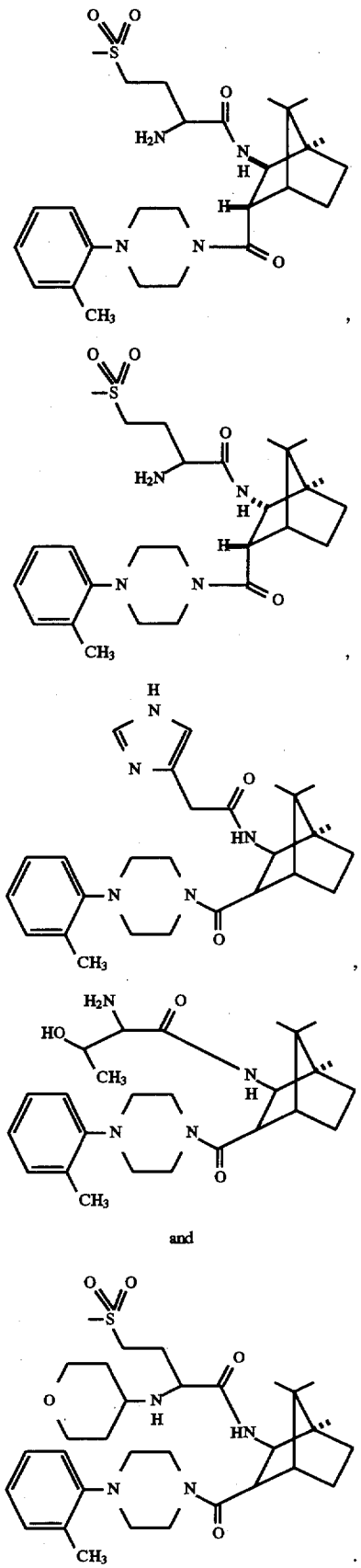

Exemplifying the present invention is a pharmaceutical composition comprising a pharmaceutically acceptable carrier and a pharmacologically effective amount of a compound of the instant invention.

More specifically illustrating the invention is a method of antagonizing the binding of oxytocin to its receptor binding site in a mammalian biologic system, comprising the step of introducing a pharmacologically effective amount of a compound of the instant invention into the mammalian biologic system.

Further illustrating the invention is a method of preventing preterm labor in a mammal in need thereof, comprising the step of administering to the mammal a pharmacologically effective amount of a compound of the instant invention.

A further illustration of the instant invention is a method of stopping labor prior to cesarian delivery in a mammal in need thereof, comprising the step of administering to the mammal a pharmacologically effective amount of a compound of the instant invention.

Specifically exemplifying the instant invention is a method of treating dysmenorrhea in a mammal in need thereof, comprising the step of administering to the mammal a pharmacologically effective amount of of the instant invention.

A further example of the invention is a method of antagonizing vasopressin from binding to its receptor site in a mammal, comprising the step of administering to the mammal a pharmacologically effective amount of a compound of the instant invention.

Another example is a method of inducing vasodilation in a mammal in need thereof, comprising the step of administering to the mammal a pharmacologically effective amount of a compound of the instant invention.

More particularly illustrating the instant invention is a method of treating hypertension in a mammal in need thereof, comprising the step of administering to the mammal a pharmacologically effective amount of a compound of the instant invention.

Another illustration of the invention is a method of inducing diuresis in a mammal in need thereof, comprising the step of administering to the mammal a pharmacologically effective amount of a compound of the instant invention.

More particularly exemplifying the invention is a method of inhibiting platelet agglutination in a mammal in need thereof, comprising the step of administering to the mammal a pharmacologically effective amount of a compound of the instant invention.

A further exemplification of the invention is a method of causing contraception in a mammal in need thereof, comprising the step of administering to the mammal a pharmacologically effective amount of a compound of the instant invention.

A further illustration of the invention is a method of improving fertility rates in a farm animal, comprising the step of administering to the farm animal a pharmacologically effective amount of a compound of the instant invention.

The terms "bridgehead position 3 and bridgehead position 6 are with reference to the following numbering scheme of camphor-type bicyclic rings:

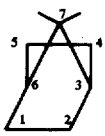

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The compounds of the present invention, may have asymmetric centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "alkenyl" shall mean straight or branched chain alkenes with one or more degrees of unsaturation at any position on the chain, of two to ten total carbon atoms, or any number within this range.

The term "alkynyl" shall mean straight or branched chain alkynes with one or more degrees of unsaturation at any position on the chain, of two to ten total carbon atoms, or any number within this range.

The term ""aryl" shall mean phenyl, naphthyl or fluorenyl.

The term "cycloalkyl" shall mean cyclic rings of alkanes of three to eight total carbon atoms.

The term "trihaloalkylsulfonyloxo" shall mean the substituent

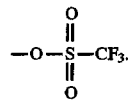

Whenever the terms "alkyl" or "aryl" or either of their prefix roots appear in a name of a substituent (e.g. aralkoxyaryloxy) they shall be interpreted as including those limitations given above for "alkyl" and "aryl". Designated numbers of carbon atoms (e.g. $C_{1-10}$) shall refer independently to the number of carbon atoms in an alkyl or cyclic alkyl moiety or to the alkyl portion of a larger substituent in which alkyl appears as its prefix root.

The term "oxo" shall refer to the substituent=O.

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of the instant invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

The compounds of the present invention also bind to the vasopressin receptor and are therefore useful as vasopressin antagonists. Vasopressin antagonists are useful in the treatment or prevention of disease states involving vasopressin disorders, including their use as diuretics and their use in congestive heart failure.

In addition, the compounds of the instant invention are useful for improving fertility rates in farm animals. In certain farm animals (sheep, cattle, swine, goats), the secretion of oxytocin from the ovary and/or pituitary acts on the uterine endometrium to stimulate the secretion of prostaglandins which in turn, causes the regression of the corpus luteum of the ovary. In the cycling animal, destruction of the corpus luteum removes the source of progesterone that is key to the preparation of the uterus for pregnancy. In the animal where fertilization has occurred, the conceptus secretes a factor that antagonizes the action of oxytocin to induce luteolysis, resulting in the continued secretion of progesterone. The maintenance of a functioning corpus luteum is obligatory to the initiation of pregnancy. An oxytocin antagonist given at this critical period supplements the natural signal from the conceptus to prolong corpus luteal function. The result is to increase pregnancy rates by enhancing the chances of impregnation through a reduction in embryonic loss.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal mutes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the an will readily understand that known variations of the conditions and processes of the following preparative procedures can be used to prepare these compounds. All temperatures are degrees Celsius unless noted otherwise.

SCHEME 1

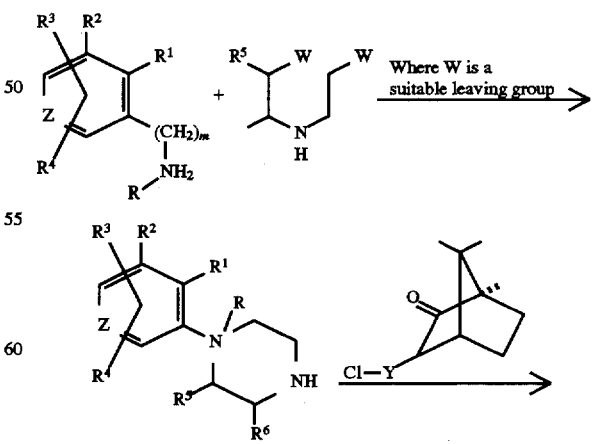

SCHEME 1
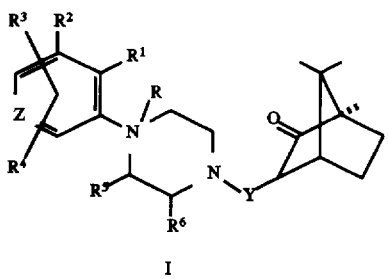
I
SCHEME 2
I $\xrightarrow{\text{1) NaH}}{\text{2) R}^7\text{—I}}$
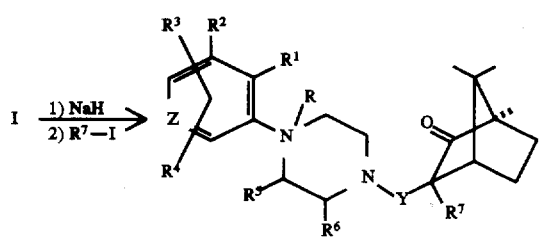
SCHEME 3
I $\xrightarrow{\text{NH}_2\text{OH}}$
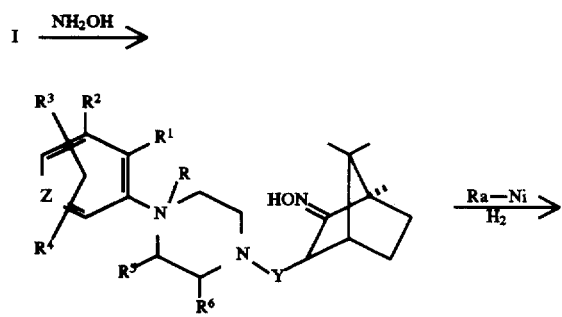
$\xrightarrow{\text{Ra—Ni}}{\text{H}_2}$
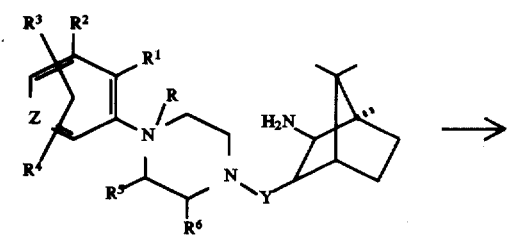
SCHEME 4
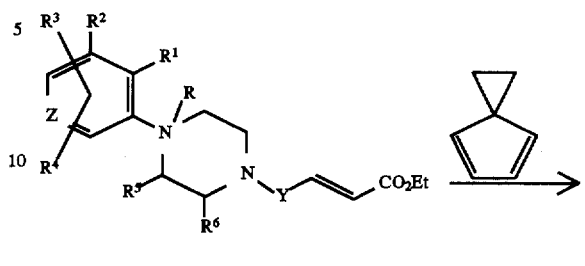
II
SCHEME 5
II $\xrightarrow{\text{LiOH}}$
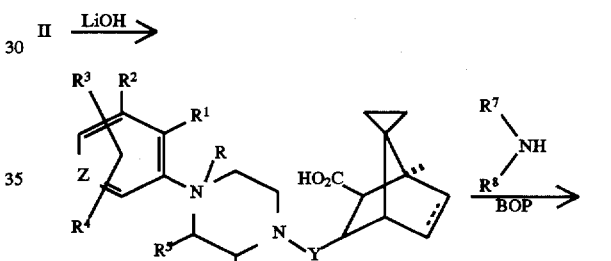
III
SCHEME 6
III $\xrightarrow{\text{DPPA}}{\text{t-butanol}}$
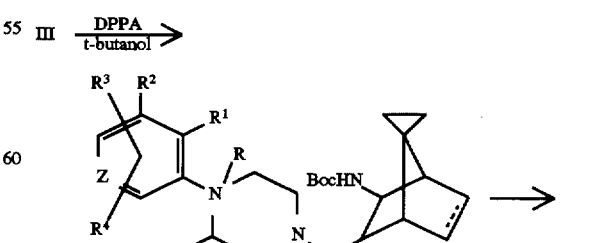

17
-continued
SCHEME 6
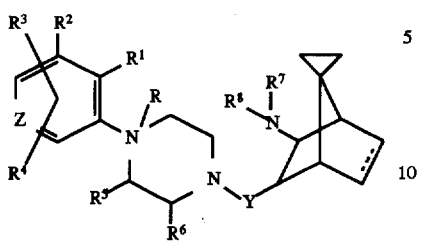
SCHEME 7
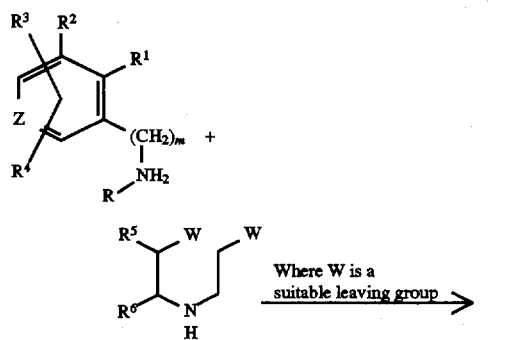
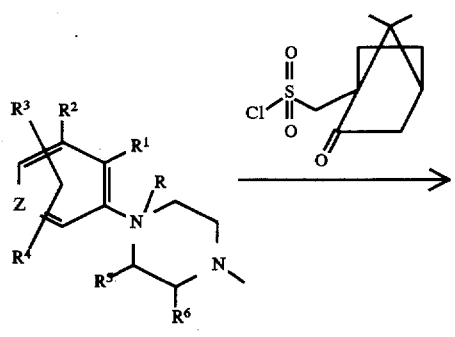
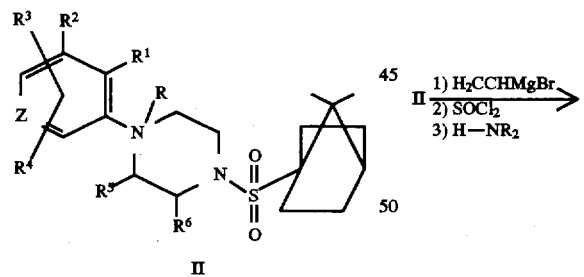
SCHEME 8
$$\text{II} \xrightarrow[\text{2) H—NR}_2]{\text{1) CH}_2\text{—S—(CH}_3)_2}$$
18
-continued
SCHEME 8
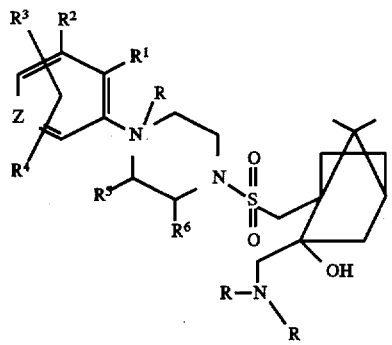
SCHEME 9
$$\text{II} \xrightarrow[\substack{\text{2) LAH} \\ \text{3) R}\underset{\text{O}}{\overset{}{\text{C}}}\text{Cl}}]{\text{1) Me}_3\text{—Si—CN}}$$
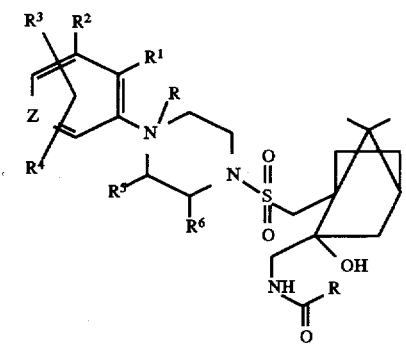
SCHEME 10
$$\text{II} \xrightarrow[\substack{\text{2) SOCl}_2 \\ \text{3) H—NR}_2}]{\text{1) H}_2\text{CCHMgBr}}$$
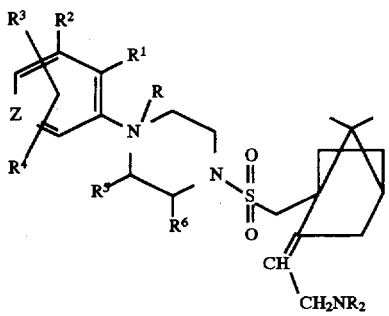

SCHEME 11

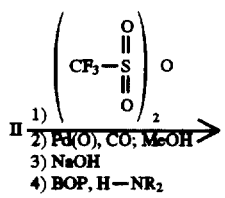

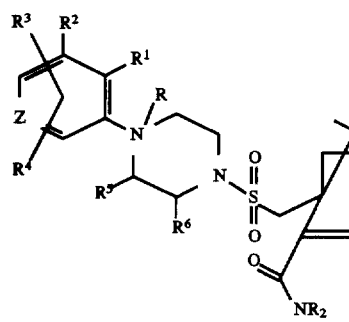

SCHEME 12

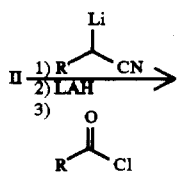

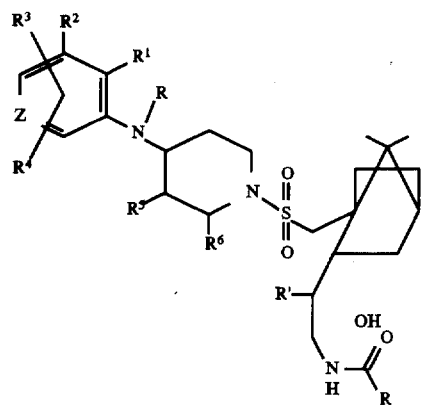

SCHEME 13

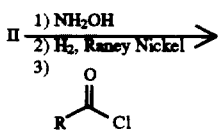

-continued
SCHEME 13

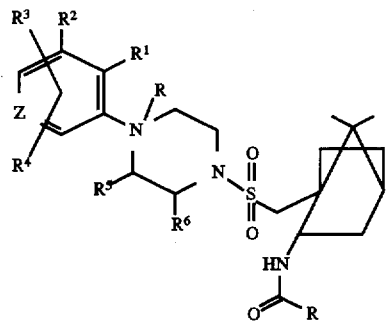

SCHEME 14

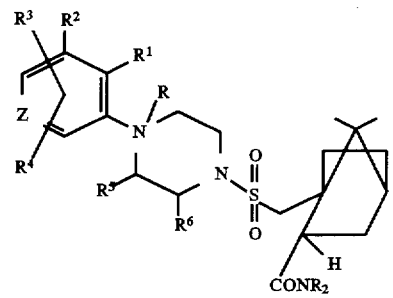

Abbreviations used in the Examples are as follows:

| | | |
|---|---|---|
| TEA | = | triethylamine |
| DIEA | = | diisopropylethylamine |
| BOP | = | benzotriazolyloxytris(dimethylamino) phosphonium hexafluorophosphate |
| THF | = | tetrahydrofuran |
| DMF | = | dimethylformamide |
| LAH | = | lithium aluminum hydride |
| TFA | = | trifluoroacetic acid |

HPLC Method A=15 min. linear gradient

95:5 A:B to 0:100 A:B

A—$H_2O$ containing 0.1% by vol. TFA

B=$CH_3CN$ containing 0.1% by vol. TFA 2.0 mL/min flow rate 12 cm $C_{18}$ reverse phase column UV detection (215 nm)

TLC was performed on 20 cm plates coated with silica gel (250 microns) from Analtech.

EXAMPLE 1

1-(2-methylphenyl)-4-[(4,7,7-trimethyl-3-oxobicyclo[2.2.1]hept-2-endo-yl)carbonyl]piperazine and 1-(2-methylphenyl)-4-[(4,7,7-trimethyl-3-oxobicyclo[2.2.1]hept-2-exo-yl)carbonyl]piperazine

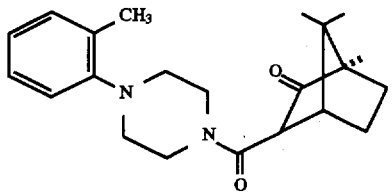

To a solution of (−) camphor-α-carboxylic acid (200 mg, 1.02 mmol) in methylene chloride (50 mL) at 0° C. was added oxallyl chloride (0.098 mL, 1.1 eq.), followed by dimethyl formamide (2 drops). After warming to room temp., and stirring for 1.5 h the solution was concentrated. The residue was redissolved in methylene chloride (50 mL) and o-tolyl piperazine hydrochloride (239 mg, 1.12 mmol) was added, followed by N-methylmorpholine (0.224 mL, 2.04 mmol). After stirring at room temperature for 4 h, the mixture was concentrated, then partitioned between ethyl acetate and water (100 mL of each). The ethyl acetate layer was dried over sodium sulfate, then concentrated. The residue was passed through a silica gel column using 30% ethyl acetate in petroleum ether as eluant. Crystallization from methylene chloride/petroleum ether afforded pure endo isomer as fine needles (173 mg). The exo isomer was obtained as a white solid from concentration of the mother liquor (62 mg).

The 2-endo and 2-exo diastereomers derived from (+) camphor-α-carboxylic acid were also prepared in the same way. Analytical data for the 2-endo and 2-exo compounds in the (+) camphor series was identical to that shown for the corresponding isomers in the (−) series.

Exo isomer: TLC: Rf (15% ethyl acetate in hexane)=0.30

Analysis: ($C_{22}H_{30}N_2O_2$) calc. C, 74.54; N, 7.90; H, 8.53 found C, 74.29; N, 7.55; H, 8.88

HPLC: (method A) $R_t$=12.10 min.

FABMS: m/z=355 (M$^+$+H)

$^1$H NMR: consistent with structure.

Endo isomer: TLC: Rf (15% ethyl acetate in hexane)= 0.09 m.p.: 185°–187° C.

Analysis: ($C_{22}H_{30}N_2O_2$) calc. C, 74.54; N, 7.90; H, 8.53 found C, 74.42; N, 7.79; H, 8.67

HPLC: (method A) $R_t$=11.73 min.

FABMS: m/z=355 (M$^+$+H)

$^1$H NMR: consistent with structure.

EXAMPLE 2

1-[(3-hydroxy-4,7,7-trimethylbicyclo[2.2.1]hept-2-yl)carbonyl]-4-(2-methylphenyl)-piperazine

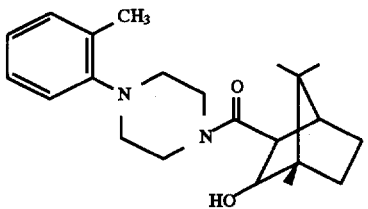

To a solution of 1-(2-Methylphenyl)-4-[(4,7,7-trimethyl-3-oxobicyclo[2.2.1]hept-2-endo-yl)carbonyl]piperazine (50 mg, 0.141 mmol) in methanol (15 mL) was added, while stirring rapidly, small scoops of sodium borohydride. When the reaction was complete, as judged by TLC, the mixture was concentrated, then partitioned between ethyl acetate and water (25 mL of each). The aqueous layer was washed 2×10 mL with ethyl acetate, then the combined ethyl acetate extracts were dried over sodium sulfate and concentrated. The title compound was purified by silica gel chromatography (15% ethyl acetate in petroleum ether as eluant) to yield 42 mg of white powder.

Analysis: ($C_{22}H_{32}N_2O_2$) calc. C, 74.12; H, 9.05; N, 7.86 found C, 74.07; H, 9.39; N, 7.76

HPLC: (method A) $R_t$=11.05 min.

FABMS: m/z=357 (M$^+$+H)

$^1$H NMR: consistent with structure.

EXAMPLE 3

1-(2-methylphenyl)-4-[(2,4,7,7-tetramethyl-3-oxobicyclo[2.2.1]hept-2-yl)carbonyl]-piperazine

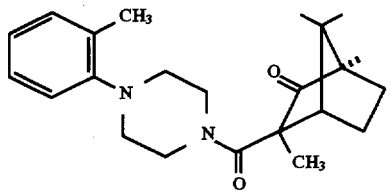

To a solution of 1-(2-Methylphenyl)-4-[(4,7,7-trimethyl-3-oxobicyclo[2.2.1]hept-2-endo-yl)carbonyl]piperazine (50 mg, 0.141 mmol) in tetrahydrofuran (25 mL) was added sodium hydride (60% dispersion in oil, 7 mg, 0.169 mmol), followed by methyl iodide (0.044 mL, 0.705 mmol). After 5 h, additional sodium hydride was added (3 mg). After 3 days, the mixture was concentrated, then partitioned between ethyl acetate and water (25 mL of each). The ethyl acetate layer was dried over sodium sulfate then concentrated. Purification by silica gel chromatography (10% ethyl acetate in petroleum ether as eluant) afforded 42 mg of the title compound as a clear film.

TLC: Rf (20% ethyl acetate in hexanes)=0.62

HPLC: (method A) $R_t$=12.70 min.

FABMS: m/z=369 (M$^+$+H)

$^1$H NMR: consistent with structure.

EXAMPLE 4

1-(2-methylphenyl)-4-[(4,7,7-trimethyl-3-oxo-2-carboxymethyl-bicyclo[2.2.1]hept-2-yl)carbonyl]-piperazine

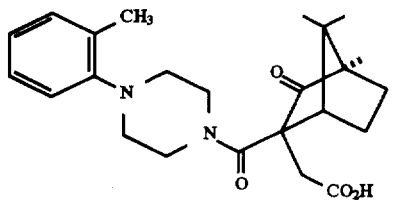

To a solution of 1-(2-Methylphenyl)-4-[(4,7,7-trimethyl-3-oxobicyclo[2.2.1]hept-2-endo-yl)carbonyl]piperazine (341 mg, 0.962 mmol) in tetrahydrofuran (50 mL) was added sodium hydride (60% dispersion in oil, 58 mg, 1.44 mmol), followed by 2-iodoethyl acetate (0.228 mL, 1.92 mmol). After stirring at room temperature for 18 h, the mixture was concentrated to afford the ethyl ester intermediate.

To a solution of the ester (150 mg, 0.352 mmol) in methanol (50 mL) was added 1M sodium hydroxide (0.703 mL, 0.703 mmol). The solution was warmed to 50° C. After 2 h the mixture was concentrated, then partitioned between ethyl acetate and 1M HCl (100 mL of each). The ethyl acetate layer was dried over sodium sulfate, then concentrated. The title compound was purified by silica gel chromatography (5% methanol in methylene chloride as eluant).

TLC: Rf (5% methanol in methylene chloride)=0.24

Analysis: $(C_{23}H_{30}N_2O_4)$+0.15 ethyl acetate calc. C, 69.40; H, 7.86; N, 6.58 found C, 69.46; H, 7.84; N, 6.23

HPLC: (method A) $R_t$=11.23 min.

FABMS: m/z=413 (M$^+$+H)

$^1$H NMR: consistent with structure.

EXAMPLE 5

1-(2-methylphenyl)-4-[(4,7,7-trimethyl-3-oxo -2-cyanomethyl-bicyclo[2.2.1 hept-2-yl)carbonyl]-piperazine

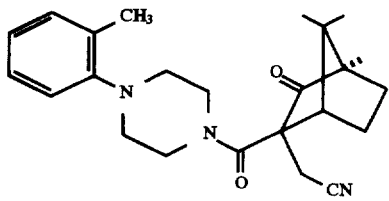

To a solution of 1-(2-Methylphenyl)-4-[(4,7,7-trimethyl-3-oxobicyclo[2.2.1]hept-2-endo-yl)carbonyl]piperazine (316 mg, 0.891 mmol) in tetrahydrofuran (50 mL) was added sodium hydride (60% dispersion in oil, 54 mg, 1.34 mmol), followed by 2-iodoacetonitrile (0.129 mL, 1.78 mmol). After stirring at room temperature for 18 h, the mixture was concentrated. The title compound was purified by silica gel chromatography (15% ethyl acetate in petroleum ether as eluant).

TLC: Rf (10% ethyl acetate in petroleum ether)=0.26

Analysis: $(C_{24}H_{31}N_3O_2)$+0.34 ethyl ether calc. C, 72.74; H, 8.28; N, 10.04 found C, 72.67; H, 7.99; N, 10.03

HPLC: (method A) $R_t$=12.8 min.

FABMS: m/z=*(M$^+$+H)

$^1$H NMR: consistent with structure.

EXAMPLE 6

1-(2-methylphenyl)-4-[(4,7,7-trimethyl-3-hydroxyimino-bicyclo[2.2.1]-hept-2-endo-yl) carbonyl]-piperazine

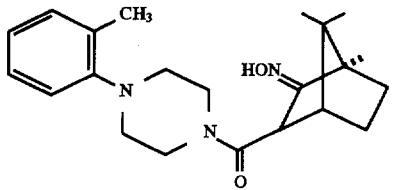

To a solution of 1-(2-Methylphenyl)-4-[(4,7,7-trimethyl-3-oxobicyclo[2.2.1]hept-2-exo-yl)carbonyl]piperazine (750 mg, 2.1 mmol) in pyridine (30 mL) was added hydroxylamine hydrochloride (300 mg, 8.57 mmol), then the temperature was increased to 70° C. When the starting material had disappeared from the TLC, the mixture was concentrated. Silica gel chromatography (96:4:0.4 chloroform: methanol: ammonia as eluant) afforded the title compound as a white solid.

Analysis: $(C_{22}H_{32}N_3O_2)$+0.30 chloroform +0.25 methanol calc. C, 65.36; H, 8.10; N, 10.14 found C, 65.38; H, 7.83; N, 9.80

HPLC: (method A) $R_t$=10.46 min.

FABMS: m/z=371 (M$^+$+H)

$^1$H NMR: consistent with structure.

EXAMPLE 7

1-(2-methylphenyl)-4-[(4,7,7-trimethyl-3-exo-aminobicyclo[2.2.1]hept-2-endo-yl)carbonyl]-piperazine and 1-(2-methylphenyl)-4-[(4,7,7-trimethyl-3-endo -aminobicyclo [2.2.1]-hept-2-endo-yl)carbonyl]-piperazine

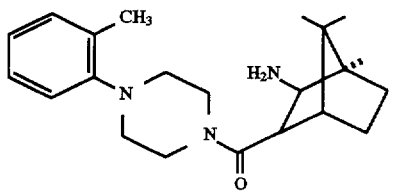

To a solution of 1-(2-methylphenyl)-4-[(4,7,7-trimethyl-3-hydroxyimino-bicyclo[2.2.1]hept-2-endo-yl)carbonyl]-piperazine (3 g, 2.29 mmol) in 2-methoxyethanol (100 mL) was added freshly prepared Raney-nickel (8–10 g of the Ra-Ni/ethanol slurry), then the reaction vessel was placed under hydrogen atmosphere (60 psi) on a Parr hydrogenator. After 2 days, the mixture was filtered. Purification by flash chromatography (98:2:0.2 chloroform: methanol: ammonium hydroxide as eluant) yielded endo and exo reduction product amines.

TLC: Rf (95:5:0.5 chloroform:methanol:ammonium hydroxide)=0.59

Analysis: $(C_{22}H_{33}N_3O_1)+0.1$ ethyl acetate calc. C, 73.84; H, 9.35; N, 11.53 found C, 73.88; H, 9.23; N, 11.60

HPLC: (method A) $R_t$=9.39 min.

FABMS: m/z=356 (M$^+$+H)

$^1$H NMR: consistent with the structure.

TLC: Rf (95:5:0.5 chloroform:methanol:ammonium hydroxide)=0.42

Analysis: $(C_{22}H_{33}N_3O_1)+0.2$ chloroform calc. C, 70.27; H, 8.82; N, 11.08 found C, 70.44; H, 9.22; N, 11.07

HPLC: (method A) $R_t$=10.12 min.

FABMS: m/z=356 (M$^+$+H)

$^1$H NMR: consistent with the structure.

EXAMPLE 8

General Coupling Procedure: For coupling carboxylic acids with the amine products of Example 7

To the amine (400 mg, 1.17 mmol) in dimethylformamide (6 mL) was added the carboxylic acid component (1.4 mmol) and Benzotriazol-1-yloxy-tris(dimethylamino) phosphonium hexafluorophosphate (BOP reagent, 619 mg, 1.4 mmol). Triethylamine was added to adjust the pH to 8. After stirring at room temperature for 18 h, the mixture was concentrated, then partitioned between ethyl acetate and 1M aqueous sodium hydroxide (75 mL of each). The ethyl acetate solution was washed with 1M HCl, and brine, then dried over sodium sulfate and concentrated. The products were obtained by flash chromatography.

EXAMPLE 9

1-(2-methylphenyl)-4-[(4,7,7-trimethyl-3-exo-(4-methylsulfonyl-2-t-butoxycarbonylamino) butanoylamino bicyclo[2.2.1]hept-2-endo-yl) carbonyl]-piperazine

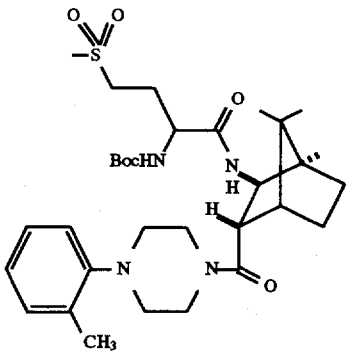

The title compound was prepared from 1-(2-methylphenyl)-4-[(4,7,7-trimethyl-3-exo-aminobicyclo [2.2.1]hept-2-endo-yl)carbonyl]-piperazine and N-Boc methionine sulfone according to the General Coupling Procedure.

TLC: Rf (95:5:0.5 chloroform:methanol:ammonium hydroxide)=0.37

Analysis: $(C_{32}H_{50}N_4O_6S_1)+0.25$ chloroform+0.50 ethyl acetate calc. C, 59.38; H, 7.89; N, 8.09 found C, 59.47; H, 8.16; N, 8.07

HPLC: (method A) $R_t$=12.58 min.

FABMS: m/z=619 (M$^+$+H)

$^1$H NMR: consistent with the structure.

EXAMPLE 10

1-(2-methylphenyl)-4-[(4,7,7-trimethyl-3-exo-(4-methylsulfonyl-2-amino) butanoylamino bicyclo [2.2.1]hept-2-endo-yl)carbonyl]-piperazine

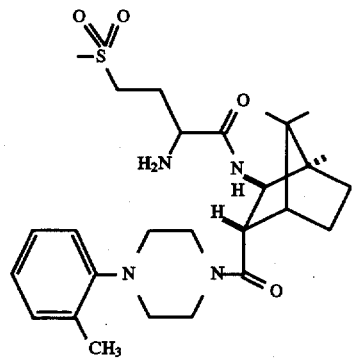

To a solution of 1-(2-methylphenyl)-4-[(4,7,7-trimethyl-3-exo-(4-methylsulfonyl-2-t-butoxycarbonylamino) butanoylamino bicyclo[2.2.1]hept-2-yl)carbonyl]-piperazine in ethyl acetate at 0° C. was introduced HCl gas. After 3 h, the mixture was concentrated. The title compound was purified by preparative HPLC (95:5 to 5:95 acetonitrile: water with 0.1% TFA) to yield 200 mg of the TFA salt.

TLC: Rf (95:5:0.5 chloroform:methanol:ammonium hydroxide)=0.11 m.p.: 96°–97° C.

Analysis: $(C_{27}H_{42}N_4O_4S_1)+2.05$ TFA+0.7 water calc. C, 48.82; H, 5.99; N, 7.32 found C, 48.82; H, 6.01; N, 7.54

HPLC: (method A) $R_t$=9.94 min.

FABMS: m/z=519 (M$^+$+H)

$^1$H NMR: consistent with the structure.

EXAMPLE 11

1-(2-methylphenyl)-4-[(4,7,7-trimethyl-3-endo-(4-methylsulfonyl-2-t-butoxycarbonylamino) butanoylamino bicyclo[2.2.1]hept-2-endo-yl) carbonyl]-piperazine

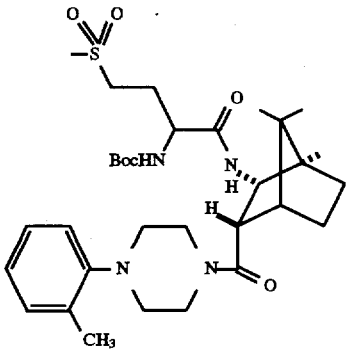

The title compound was prepared from 1-(2-methylphenyl)-4-[(4,7,7-trimethyl-3-endo-aminobicyclo [2.2.1]hept-2-endo-yl)carbonyl]-piperazine and N-Boc methionine sulfone according to the General Coupling Procedure.

Analysis: $(C_{32}H_{50}N_4O_6S_1)+0.5$ CHCl$_3$ calc. C, 57.52; H, 7.50; N, 8.26 found C, 57.54; H, 7.72; N, 8.02

HPLC: (method A) R$_t$=13.44 min.
FABMS: m/z=619 (M$^+$+H)
$^1$H NMR: consistent with the structure.

EXAMPLE 12

1-(2-methylphenyl)-4-[(4,7,7-trimethyl-3-endo-(4-methylsulfonyl-2-amino) butanoylamino bicyclo[2.2.1]hept-2-endo-yl)carbonyl]-piperazine

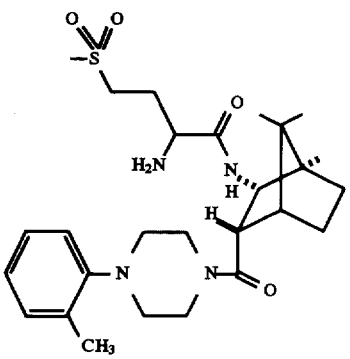

The title compound was prepared from 1-(2-methylphenyl)-4-[(4,7,7-trimethyl-3-endo-(4-methylsulfonyl-2-t-butoxycarbonylamino) butanoylamino bicyclo[2.2.1]hept-2-endo-yl)carbonyl]-piperazine by an route analogous to that described for 1-(2-methylphenyl)-4-[(4,7,7-trimethyl-3-exo-(4-methylsulfonyl-2-amino) butanoylamino bicyclo[2.2.1]hept-2-endo-yl)carbonyl]-piperazine.

Analysis: (C$_{27}$H$_{42}$N$_4$O$_4$S$_1$)+2.15 water calc. C, 58.17; H, 8.37; N, 9.76 found C, 58.16; H, 8.16; N,10.05

HPLC: (method A) R$_t$=10.58 min.
FABMS: m/z=519 (M$^+$+H)
$^1$H NMR: consistent with the structure.

EXAMPLE 13

1-(2-Methylphenyl)-4-[(4,7,7-trimethyl-3-(2-(4-imidazolyl)) acetylamino bicyclo[2.21]hept-2-yl)carbonyl]-piperazine

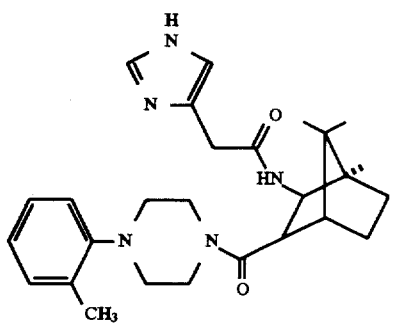

The title compound was prepared from 1-(2-methylphenyl)-4-[(4,7,7-trimethyl-3-aminobicyclo[2.2.1]hept-2-yl)carbonyl]-piperazine and imidazole acetic acid according to the General Coupling Procedure.

TLC: Rf (90:10:1 chloroform:methanol:ammonium hydroxide)=0.41

Analysis: (C$_{27}$H$_{37}$N$_5$O$_2$)+1.0 ethyl acetate+0.05 chloroform calc. C, 66.87; H, 8.14; N, 12.56 found C, 66.99; H, 8.19; N, 12.55

HPLC: (method A) R$_t$=10.19 min.
FABMS: m/z=464 (M$^+$+H)
$^1$H NMR: consistent with the structure.

EXAMPLE 14

1-(2-methylphenyl)-4-[(4,7,7-trimethyl-3-acetylamino bicyclo[2.2.1]hept-2-yl)carbonyl]-piperazine

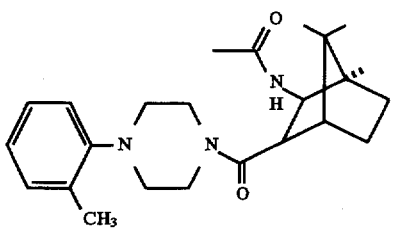

To a solution of 1-(2-methylphenyl)-4-[(4,7,7-trimethyl-3-aminobicyclo[2.2.1]hept-2-yl)carbonyl]-piperazine (50 mg, 0.14 mmol) in methylene chloride (3 mL) was added acetic anhydride (0.016 mL, 0.169 mmol) followed by 4-dimethylaminopyridine (DMAP, 21 mg, 0.169 mmol). After 3 h, the mixture was concentrated, then partitioned between ethyl acetate and 10% aqueous citrate (25 mL each). The ethyl acetate layer was then washed with brine, dried over magnesium sulfate and concentrated. The title compound was purified by preparative TLC (3×0.25 mm plates, 96:4:0.4 chloroform:methanol:ammonium hydroxide as eluant)

TLC: Rf (95:5:0.5 chloroform:methanol:ammonium hydroxide)=0.39

Analysis: (C$_{24}$H$_{35}$N$_3$O$_2$)+0.8 water calc. C, 69.85; H, 8.52; N, 10.18 found C, 69.92; H, 8.41; N,10.12

HPLC: (method A) R$_t$=11.82 min.
FABMS: m/z=398 (M$^+$+H)
$^1$H NMR: consistent with the structure.

EXAMPLE 15

1-(2-methylphenyl)-4-[(4,7,7-trimethyl-3-prolyl amino bicyclo[2.2.1]hept-2-yl)carbonyl]-piperazine

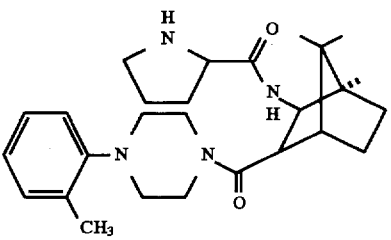

N-Boc Proline was coupled to 1-(2-methylphenyl)-4-[(4,7,7-trimethyl-3-aminobicyclo[2.2.1]hept-2-yl)carbonyl]-piperazine using BOP reagent as described in the General Coupling Procedure.

The Boc protected intermediate was dissolved in ethyl acetate and cooled to 0° C. HCl gas was introduced. After 5 h, the mixture was concentrated. The title compound was purified by preparative HPLC (90:10 to 10:90 water:acetonitrile+0.1% TFA as eluant).

TLC: Rf (95:5:0.5 chloroform:methanol:ammonium hydroxide)=0.46

Analysis: $(C_{27}H_{40}N_4O_2)+0.55$ water$+2.0$ TFA calc. C, 53.91; H, 6.29; N, 8.11 found C, 53.92; H, 6.27; N, 8.19

HPLC: (method A) $R_t=9.88$ min.

FABMS: m/z=453 ($M^++H$)

$^1H$ NMR: consistent with the structure.

EXAMPLE 16

1-(2-methylphenyl)-4-[(4,7,7-trimethyl-3-(1-(ethoxycarbonylethyl)prolyl amino bicyclo[2.2.1] hept-2-yl)carbonyl]-piperazine

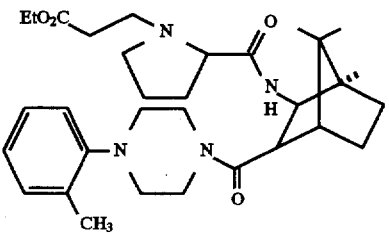

To a solution of 1-(2-methylphenyl)-4-[(4,7,7-trimethyl-3-prolyl amino bicyclo[2.2.1]hept-2-yl)carbonyl]-piperazine (100 mg, 0.221 mmol) in methanol (3 mL) was added ethyl acrylate (0.024 mL, 0.221 mmol) and triethylamine (0.045 mL, 0.44 mmol). After stirring at room temperature for 18 h, the mixture was concentrated, then partitioned between ethyl acetate and sat'd sodium bicarbonate (50 mL each). The ethyl acetate was washed with brine, then dried over magnesium sulfate and concentrated. The title compound was purified by preparative TLC (3×0.5 mm plates, 96:4:0.4 chloroform: methanol:ammonium hydroxide as eluant) to yield a 70:30 mixture of ethyl:methyl esters.

TLC: Rf (95:5:0.5 chloroform:methanol:ammonium hydroxide)=0.35

Analysis: $(C_{32}H_{48}N_4O_4)+0.15$ methanol$+0.20$ chloroform calc. C, 66.68; H, 8.42; N, 9.71 found C, 66.63; H, 8.42; N,10.40

HPLC: (method A) $R_t=10.77$ min (methyl ester), 11.15 min (ethyl ester)

FABMS: m/z=539 ($M^++H$, methyl ester), 553 ($M^++H$, ethyl ester)

$^1H$ NMR: consistent with 70:30 ratio of ethyl:methyl esters.

EXAMPLE 17

1-(2-methylphenyl)-4-[(4,7,7-trimethyl-3-(2-hydroxy-2,2-dimethyl)acetylaminobicyclo[2.2.1] hept-2-yl)carbonyl-piperazine

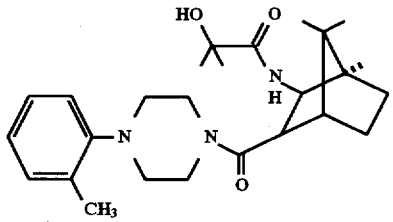

2-hydroxy isobutyric acid was coupled to 1-(2-methylphenyl)-4-[(4,7,7-trimethyl-3-aminobicyclo[2.2.1] hept-2-yl)carbonyl]-piperazine using BOP reagent as described in the General Coupling Procedure. The title compound was purified by flash chromatography (2:1 hexanes:ethyl acetate as eluant).

TLC: Rf (2:3 ethyl acetate:hexanes)=0.38

Analysis: $(C_{26}H_{39}N_3O_3)+0.4$ chloroform$+0.65$ ethyl acetate calc. C, 63.71; H, 8.22; N, 7.69 found C, 63.71; H, 8.19; N, 7.82

HPLC: (method A) $R_t=11.59$ min.

FABMS: m/z=442 ($M^++H$)

$^1H$ NMR: consistent with the structure.

EXAMPLE 18

1-(2-methylphenyl)-4-[(4,7,7-trimethyl-3-(2,3-dihydroxy) propionyl aminobicyclo[2.2.1]hept-2-yl) carbonyl]-piperazine

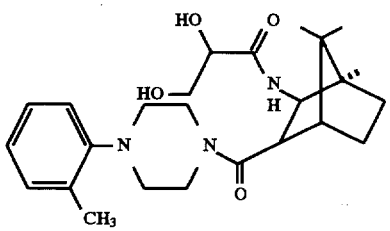

Glyceric acid was coupled to 1-(2-methylphenyl)-4-[(4,7,7-trimethyl-3-exo-aminobicyclo[2.2.1]hept-2-endo-yl) carbonyl]-piperazine using BOP reagent as described in the General Coupling Procedure. The title compound was purified by preparative TLC (2×0.5 mm plates, 92:8:0.8 chloroform:methanol:ammonium hydroxide as eluant).

TLC: Rf (95:5:0.5 chloroform:methanol:ammonium hydroxide)=0.28

Analysis: $(C_{25}H_{37}N_3O_4)+0.1$ chloroform$+0.1$ methanol calc. C, 65.98; H, 8.24; N, 9.16 found C, 65.95; H, 8.39; N,9.21

HPLC: (method A) $R_t=10.63$ min.

FABMS: m/z=434 ($M^++H$)

$^1H$ NMR: consistent with the structure.

EXAMPLE 19

1-(2-methylphenyl)-4-[(4,7,7-trimethyl-3-(2-(t-butoxycarbonyl)amino-3-hydroxy) butyryl aminobicyclo[2.2.1]hept-2-yl)carbonyl]-piperazine

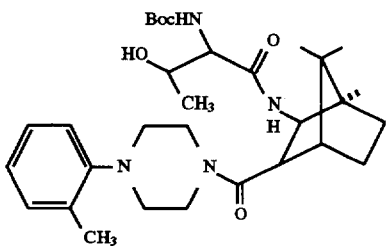

N-Boc threonine was coupled to 1-(2-methylphenyl)-4-[(4,7,7-trimethyl-3-exo-aminobicyclo[2.2.1]hept-2-endo-yl) carbonyl]-piperazine using BOP reagent as described in the General Coupling Procedure. The title compound was purified by flash chromatography (2:1 ethyl acetat:hexanes as eluant)

TLC: Rf (95:5:0.5 chloroform:methanol:ammonium hydroxide)=0.41

Analysis: $(C_{31}H_{48}N_4O_5)$+0.25 chloroform calc. C, 63.98; H, 8.29; N, 9.55 found C, 64.05; H, 8.33; N, 9.83

HPLC: (method A) $R_t$=13.07 min.

FABMS: m/z=557 (M$^+$+H)

$^1$H NMR: consistent with the structure.

EXAMPLE 20

1-(2-methylphenyl)-4-[(4,7,7-trimethyl-3-(2-amino-3-hydroxy) butyryl aminobicyclo[2.2.1]hept-2-yl) carbonyl]-piperazine

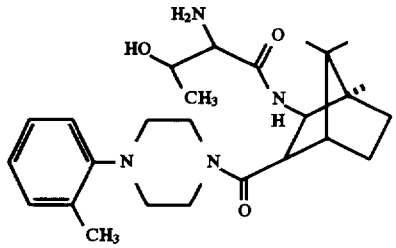

To a solution of 1-(2-methylphenyl)-4-[(4,7,7-trimethyl-3-(2-(t-butoxycarbonyl)amino-3-hydroxy) butyryl aminobicyclo[2.2.1]hept-2-yl)carbonyl]-piperazine (30 mg, 0.059 mmol) in ethyl acetate (10 mL) at 0° C. was introduced a stream of HCl gas. After 2 h, the mixture was filtered, then the filtrate was dried under high vac. to yield 25 mg.

Analysis: $(C_{31}H_{40}N_4O_3)$+0.36 ethyl acetate calc. C, 51.24; H, 7.39; N, 8.72 found C, 51.20; H, 7.28; N, 8.68

HPLC: (method A) $R_t$=10.29 min.

FABMS: m/z=457 (M$^+$+H)

$^1$H NMR: consistent with the structure.

EXAMPLE 21

1-(2-Methylphenyl)-4-[(4,7,7-trimethyl-3-endo-(4-methylsulfonyl-2-(4-tetrahydropyranyl)amino) butanoylamino bicyclo[2.2.1]hept-2-endo-yl) carbonyl]-piperazine

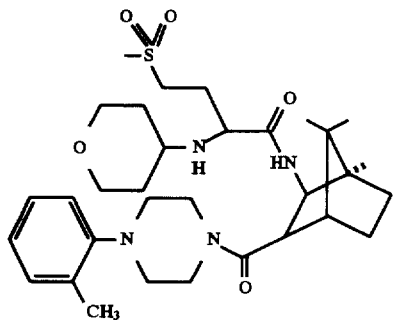

To a solution of 1-(2-methylphenyl)-4-[(4,7,7-trimethyl-3-endo-(4-methylsulfonyl-2-amino) butanoylamino bicyclo [2.2.1]hept-2-endo-yl)carbonyl]-piperazine (150 mg, 0.28 mmol) in 1% acetic acid/methanol (5 mL) at 0° C. was added pyran-4-one (0.072 mL, 0.34 mmol) followed by sodium cyanoborohydride (21 mg, 0.34 mmol). After 18 h, the mixture was concentrated, then partitioned between ethyl acetate and brine (50 mL each). The ethyl acetate solution was dried over magnesium sulfate, then concentrated. The title compound was purified by flash chromatography (2:1 hexanes:ethyl acetate as eluant) to afford 110 mg of white solid.

TLC: Rf (95:5:0.5 chloroform:methanol:ammonium hydroxide)=0.18

Analysis: $(C_{32}H_{50}N_4O_5S_1)$+0.1 chloroform calc. C, 62.71; H, 8.21; N, 9.11 found C, 62.47; H, 8.24; N, 9.14

HPLC: (method A) $R_t$=10.34 min.

FABMS: m/z=603 (M$^+$+H)

$^1$H NMR: consistent with the structure.

EXAMPLE 22

General Procedure for the Diels-Alder Reaction

To a solution of dienophile in toluene was added the diene. The temperature was increased to reflux. After 2 days the mixture was concentrated to yield crude cycloadduct.

EXAMPLE 23

1-(2-methylphenyl)-4-[spiro(bicyclo[2.2.1]hept-5-ene-7,1'-cyclopropan-2-endo-ethoxycarbonyl-3-exo-yl)carbonyl]piperazine and 1-(2-methylphenyl)-4-[spiro(bicyclo[2.2.1]hept-5-ene-7,1'-cyclopropan-2-exo-ethoxycarbonyl-3-endo-yl)carbonyl]piperazine

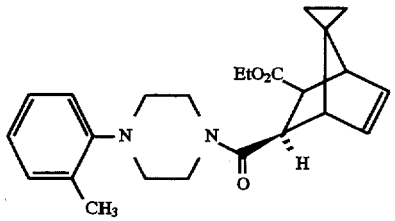

Spiro[2.4]hepta-4,6-diene and ethyl, o-tolylpiperazinyl fumarate were condensed as described in the General Procedure for the Diels-Alder Reaction. The title compounds were separated and purified by flash chromatography (10% ethyl acetate in petroleum ether as eluant).

Analysis: $(C_{24}H_{30}N_2O_3)$+0.12 water calc. C, 72.64; H, 7.70; N, 7.06 found C, 72.55; H, 7.83; N, 6.73

HPLC: (method A) $R_t$=12.91 min.

FABMS: m/z=395 (M$^+$+H)

$^1$H NMR: consistent with structure.

Analysis: $(C_{24}H_{30}N_2O_3)$ calc. C, 73.05; H, 7.68; N, 7.10 found C, 72.74; H, 7.84; N, 6.81

HPLC: (method A) $R_t$=12.22 min.

FABMS: m/z=395 (M$^+$+H)

$^1$H NMR: consistent with structure.

EXAMPLE 24

1-(2-methylphenyl)-4-[spiro(bicyclo[2.2.1]hept-5-ene-7,1'-cyclopropan-2-endo-carboxyl-3-exo-yl)carbonyl]piperazine

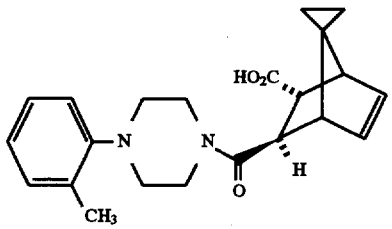

To a solution of 1-(2-methylphenyl)-4-[spiro(bicyclo[2.2.1]hept-5-ene-7,1'-cyclopropan-2-endo-ethoxycarbonyl-3-exo-yl)carbonyl]piperazine (700 mg, 1.8 mmol) in tetrahydrofuran (13.8 mL) was added a 1M aqueous solution of lithium hydroxide (18 mL, 18 mmol). After stirring for 18 h at room temperature followed by 18 h at 50° C., the mixture was concentrated then partitioned between ethyl acetate and 1M HCl (75 mL each). The ethyl acetate layer was dried over sodium sulfate then concentrated to yield 580 mg of the title compound.

m.p.: 185°–187° C.

Analysis: $(C_{22}H_{26}N_2O_3)+0.5$ water calc. C, 70.36; H, 7.26; N, 7.46 found C, 70.75; H, 6.91; N, 7.67

HPLC: (method A) $R_t$=10.62 min.

FABMS: m/z=367 (M$^+$+H)

$^1$H NMR: consistent with the structure.

EXAMPLE 25

1-(2-methylphenyl)-4-[spiro(bicyclo[2.2.1]hept-5-ene-7,1'-cyclopropan-2-(t-butoxycarbonyl)amino-3-yl)carbonyl]piperazine

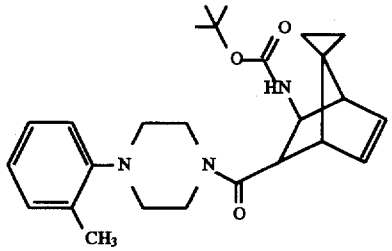

To a solution of 1-(2-methylphenyl)-4-[spiro(bicyclo[2.2.1]hept-5-ene-7,1'-cyclopropan-2-carboxyl-3-yl)carbonyl]piperazine (200 mg, 0.54 mmol) in t-butanol (4 mL) was added diphenylphosphorylazide (DPPA, 0.12 mL, 0.57 mmol) followed by the dropwise addition of triethylamine (0.08 mL, 0.58 mmol). The temperature was increased to reflux. After 1 h, CuCl (11 mg, 0.11 mmol) was added. After 2 h, the mixture was cooled, diluted with diethyl ether (50 mL) then washed with 1M sodium hydroxide, water, and brine. The ethyl ether layer was dried over sodium sulfate, then concentrated to an orange foam. The title compound was purified by flash chromatography (20% ethyl acetate in hexanes as eluant) to yield 82 mg of pure product.

m.p.: 164°–166° C.

Analysis: $(C_{26}H_{35}N_3O_3)+0.75$ water calc. C, 69.21; H, 8.17; N, 9.32 found C, 69.53; H, 8.56; N, 9.46

HPLC: (method A) $R_t$=13.17 min.

FABMS: m/z=438 (M$^+$+H)

$^1$H NMR: consistent with the structure.

EXAMPLE 26

1-(2-methylphenyl)-4-[spiro(bicyclo[2.2.1]hept-5-ene-7,1'-cyclopropan-2-(2-ethylmercaptoethyl)aminocarbonyl-3-yl)carbonyl]piperazine

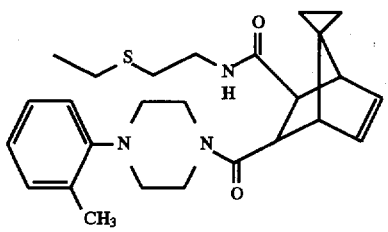

To a solution of 1-(2-methylphenyl)-4-[spiro(bicyclo[2.2.1]hept-5-ene-7,1'-cyclopropan-2-endo-carboxyl-3-exo-yl)carbonyl]piperazine (75 mg, 0.20 mmol) in dimethylformamide (3 mL) was added 2-(ethylthio)ethylamine hydrochloride (28 mg, 0.2 mmol), N-ethyl, N',N'-(dimethylamino)propyl carbodiimide (EDC, 38 mg, 0.2 mmol), hydroxybenzotriazole (27 mg, 0.2 mmol), and triethylamine (0.055 mL, 0.4 mmol). After stirring at room temperature for 18 h, the mixture was diluted with ethyl acetate (50 mL) then washed with saturated aqueous sodium bicarbonate and brine (50 mL each), then dried over sodium sulfate and concentrated. The title compound was isolated with flash chromatography (40% ethyl acetate in hexanes as eluant) to yield 64 mg.

m.p.: 111°–112° C.

Analysis: $(C_{26}H_{35}N_3O_2S)+0.5$ water calc. C, 67.48; H, 7.86; N, 9.08 found C, 67.35; H, 7.87; N, 8.93

HPLC: (method A) $R_t$=10.27 min.

FABMS: m/z=454 (M$^+$+H)

$^1$H NMR: consistent with the structure.

EXAMPLE 27

1-(2-methylphenyl)-4-[spiro(bicyclo[2.2.1]heptane-7,1'-cyclopropan-2-ethoxycarbonyl-3-yl)carbonyl]piperazine

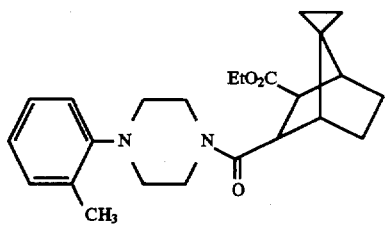

To a solution of 1-(2-methylphenyl)-4-[spiro(bicyclo[2.2.1]hept-5-ene-7,1'-cyclopropan-2-endo-carboxyl-3-exo-yl)carbonyl]piperazine (1 g, 2.5 mmol) in ethanol (28 mL) was added 10% palladium on carbon (100 mg). The mixture was then placed under hydrogen atmosphere at room pressure. After 3 h, the mixture was filtered then concentrated to yield 1 g.

m.p.: 102°–103° C.

Analysis: $(C_{24}H_{32}N_2O_3)$ calc. C, 72.68; H, 8.15; N, 7.06 found C, 72.43; H, 8.08; N, 7.08

HPLC: (method A) R_f=14.15 min.
FABMS: m/z=397 (M⁺+H)
¹H NMR: consistent with the structure.

EXAMPLE 28

1-(2-methylphenyl)-4-[spiro(bicyclo[2.2.1]heptane-7,1'-cyclopropan-2-(N,N-diethylamino)carbonyl-3-yl)carbonyl]piperazine

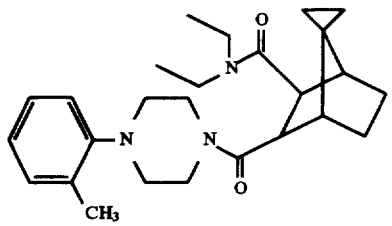

Part I: To a solution of 1-(2-methylphenyl)-4-[spiro(bicyclo[2.2.1]hept-5-ene-7,1'-cyclopropan-2-ethoxycarbonyl-3-yl)carbonyl]piperazine (390 mg, 1.06 mmol, in ethanol (12 mL) was added 10% palladium on carbon (39 mg). The mixture was then placed under hydrogen atmosphere at room pressure. After 18 h, the mixture was filtered and concentrated to yield 390 mg of the carboxylic acid.

Part II: To a solution of the carboxylic acid from part I (75 mg, 0.20 mmol) in dimethylformamide (3 mL) was added diethylamine (0.062 mL, 0.44 mmol), N-ethyl, N',N'-(dimethylamino)propyl carbodiimide (EDC, 38 mg, 0.2 mmol), and hydroxybenzotriazole (27 mg, 0.2 mmol). After stirring at room temperature for 18 h, the mixture was diluted with ethyl acetate (50 mL) then washed with saturated aqueous sodium bicarbonate and brine (50 mL each), then dried over sodium sulfate and concentrated. The title compound was isolated with flash chromatography (30% ethyl acetate in hexanes as eluant) to yield 91 mg as an amorphous foam.

Analysis: $(C_{26}H_{37}N_3O_2)$+0.5 water calc. C, 72.17; H, 8.87; N, 9.71 found C, 72.16; H, 8.66; N, 9.50

HPLC: (method A) R_f=13.05 min.
FABMS: m/z=424 (M⁺+H)
¹H NMR: consistent with the structure.

EXAMPLE 29

1-(2-methylphenyl)-4-[spiro(bicyclo[2.2.1]heptane-7,1'-cyclopropan-2-(2-(N,N-dimethylaminoethyl)amino carbonyl-3-yl)carbonyl]piperazine

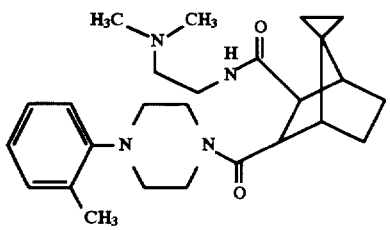

To a solution of 1-(2-methylphenyl)-4-[spiro(bicyclo[2.2.1]heptane-7,1'-cyclopropan-2-carboxyl-3-yl)carbonyl] piperazine (75 mg, 0.20 mmol) in dimethylformamide (3 mL) was added N,N-(dimethylaminoethyl)amine (0.087 mL, 0.80 mmol), N-ethyl, N',N'-(dimethylamino)propyl carbodiimide (EDC, 50 mg, 0.26 mmol), and hydroxybenzotriazole (35 mg, 0.26 mmol). After stirring at room temperature for 18 h, the mixture was diluted with ethyl acetate (50 mL) then washed with saturated aqueous sodium bicarbonate and brine (50 mL each), then dried over sodium sulfate and concentrated. The title compound was purified by flash chromatography (92:8:0.8 chloroform:methanol:ammonium hydroxide as eluant).

m.p.: 158°–159° C.

Analysis: $(C_{26}H_{38}N_4O_2)$+0.5 water calc. C, 69.75; H, 8.80; N, 12.52 found C, 70.01; H, 8.45; N, 12.34

HPLC: (method A) R_f=10.10 min.

FABMS: m/z=439 (M⁺+H)

¹H NMR: consistent with the structure.

EXAMPLE 30

1-(2-methylphenyl)-4-[spiro(bicyclo[2.2.1]heptane-7,1'-cyclopropan-2-(2-hydroxyethyl)amino)carbonyl-3-yl)carbonyl]piperazine

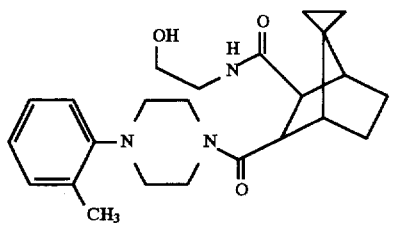

To a solution of 1-(2-methylphenyl)-4-[spiro(bicyclo[2.2.1]heptane-7,1'-cyclopropan-2-carboxyl-3-yl)carbonyl] piperazine (90 mg, 0.24 mmol) in methylene chloride (5 mL) was added dimethylformamide (1 drop), followed by oxallyl chloride (0.032 mL, 0.36 mmol). After 2 h, the mixture was concentrated, redissolved in methylene chloride (3 mL), then ethanolamine (0.5 mL) was added. After 18 h, the mixture was diluted with methylene chloride (50 mL), then washed with saturated aqueous sodium bicarbonate and brine (50 mL each), then dried over sodium sulfate and concentrated. The title compound was purified by flash chromatography (100% ethyl acetate as eluant).

m.p.: 173°–174° C.

Analysis: $(C_{24}H_{33}N_3O_3)$ calc. C, 70.03; H, 8.10; N, 10.21 found C, 69.67; H, 8.01; N, 9.99

HPLC: (method A) R_f=10.22 min.

FABMS: m/z=412 (M⁺+H)

¹H NMR: consistent with the structure.

EXAMPLE 31

1-(2-methylphenyl)-4-[spiro(bicyclo[2.2.1]heptane-7,1'-cyclopropan- 2-hydroxymethyl-3-yl)carbonyl] piperazine

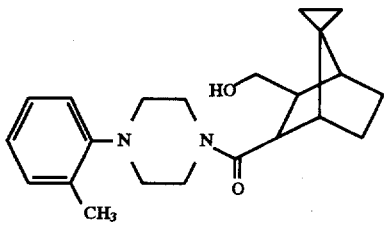

To a solution of 1-(2-methylphenyl)-4-[spiro(bicyclo [2.2.1]heptane-7,1'-cyclopropan-2-carboxyl-3-yl)carbonyl] piperazine (50 mg, 0.14 mmol) in tetrahydrofuran (2 mL) at 0° C. was added dropwise a solution of borane in tetrahydrofuran (1M, 0.03 mL, 0.30 mmol). After 1 h, 1M HCl was added (5 drops), and stirring was continued at room temperature. After 1 h, aqueous sodium carbonate was added until pH>7, then the mixture was washed with ethyl acetate (2×50 mL). The ethyl acetate extracts were washed with brine, then dried over sodium sulfate and concentrated. The title compound was purified by flash chromatography (a graedient from 40% to 50% ethyl acetate in hexanes as eluant) to afford 30 mg of white solid.

m.p.: 141°–143° C.

Analysis: $(C_{22}H_{30}N_2O_2)+0.5$ water calc. C, 72.68; H, 8.61; N, 7.71 found C, 72.97; H, 8.44; N, 7.67

HPLC: (method A) $R_t$=11.39 min.

FABMS: m/z=355 (M$^+$+H)

$^1$H NMR: consistent with the structure.

EXAMPLE 32

1-(2-methylphenyl)-4-[spiro(bicyclo[2.2.1] heptane-7,1'-cyclopropan-2-pivalyloxymethyl-3-yl)carbonyl] piperazine

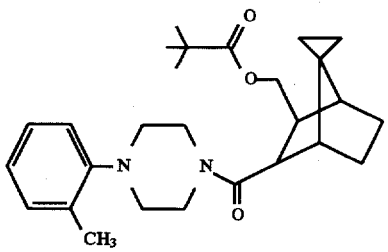

To a solution of 1-(2-methylphenyl)-4-[spiro(bicyclo [2.2.1]heptane-7,1'-cyclopropan-2-hydroxymethyl-3-yl) carbonyl]piperazine (65 mg, 0.18 mmol) in pyridine (2 mL) was added N,N-dimethylaminopyridine (17 mg, 0.14 mmol) followed by trimethylacetyl chloride (0.034 mL, 0.27 mmol). After 18 h, the mixture was diluted with ethyl acetate (50 mL), washed with 10% aqueous citric acid and brine (50 mL each), then dried over sodium sulfate and concentrated. The title compound was purified by flash chromatography (10% ethyl acetate in hexanes as eluant) to yield an amorphous foam.

Analysis: $(C_{27}H_{38}N_2O_3)+0.7$ water calc. C, 71.86; H, 8.80; N, 6.21 found C, 71.92; H, 8.56; N, 6.11

FABMS: m/z=439 (M$^+$+H)

$^1$H NMR: consistent with the structure.

EXAMPLE 33

1-(2-methylphenyl)-4-[spiro(bicyclo[2.2.1]hept-5-ene-7,1'-cyclopropan-2-butoxycarbonyl-3-yl) carbonyl]piperazine

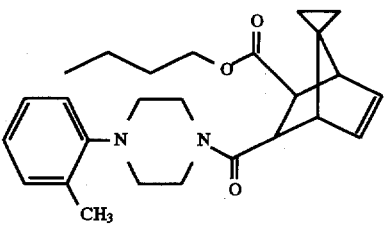

To a solution of 1-(2-methylphenyl)-4-[spiro(bicyclo [2.2.1]hept-5-ene-7,1'-cyclopropan-2-carboxyl-3-yl) carbonyl]piperazine (86 mg, 0.23 mmol) in methylene chloride (3 mL) was added dimethylformamide (1 drop) followed by oxallyl chloride (0.03 mL, 0.35 mmol). After 2 h, the mixture was concentrated, then redissolved in methylene chloride (0.5 mL) and added to a solution of butanol (3 mL) and triethylamine (0.32 mL, 2.3 mmol). After 18 h, the mixture was diluted with ethyl acetate (70 mL), washed with water and brine (70 mL each), dried over sodium sulfate and concentrated. Purification by flash chromatography (10% ethyl acetate in hexanes as eluant) to yielded 45 mg of the title compound as an oil.

Analysis: $(C_{26}H_{34}N_2O_3)+0.35$ ethyl acetate calc. C, 72.59; H, 8.18; N, 6.18 found C, 72.53; H, 8.10; N, 6.34

FABMS: m/z=423 (M$^+$+H)

$^1$H NMR: consistent with the structure.

EXAMPLE 34

1-(2-methylphenyl)-4-[spiro(bicyclo[2.2.1]hept-5-ene-7,1'-cyclopropan-2-(2pyridinemethyloxy) carbonyl-3yl)carbonyl]piperazine

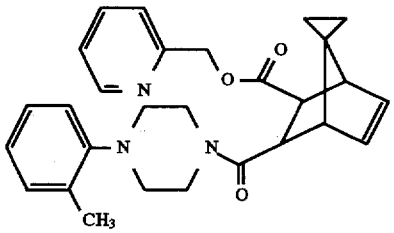

To a solution of 1-(2-methylphenyl)-4-[spiro(bicyclo [2.2.1]hept-5-ene-7,1'-cyclopropan-2-carboxyl-3-yl) carbonyl]piperazine (75 mg, 0.20 mmol) in methylene chloride (3 mL) was added dimethylformamide (1 drop) followed by oxallyl chloride (0.18 mL, 2 mmol). After 2 h, the mixture was concentrated, then redissolved in methylene chloride (2 mL). Triethylamine (0.28 mL, 2 mmol) was added, followed by 2-pyridyl carbinol (3 mL). After 18 h at room temperature, the mixture was partitioned between ethyl acetate and a saturated aqueous solution of sodium bicarbonate (75 mL each). The ethyl acetate layer was washed with water (2×70 mL), brine (50 mL), then dried over sodium sulfate and concentrated. Purification by flash chromatography (10% ethyl acetate in hexanes as eluant) afforded 58 mg of the title compound as an amorphous foam.

Analysis: (C$_{28}$H$_{31}$N$_3$O$_3$)+0.80 ethyl acetate calc. C, 70.97; H, 7.14; N, 7.96 found C, 70.95; H, 6.92; N, 8.12

HPLC: (method A) R$_t$=9.98 min.

FABMS: m/z=458 (M$^+$+H)

$^1$H NMR: consistent with the structure.

EXAMPLE 35

1-(2-methylphenyl)-4-[spiro(bicyclo[2.2.1]hept-5-ene-7,1'-cyclopropan-2-(2-piperidinemethyloxy) carbonyl-3-yl)carbonyl]piperazine

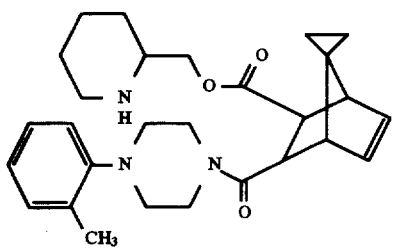

Part I: To a solution of 1-(2-methylphenyl)-4-[spiro (bicyclo[2.2.1]hept-5-ene-7,1'-cyclopropan-2-carboxyl-3-yl)carbonyl]piperazine (93 mg, 0.25 mmol) in methylene chloride (3 mL) was added dimethylformamide (1 drop) followed by oxallyl chloride (0.22 mL, 2.5 mmol). After 2 h, the mixture was concentrated, then redissolved in methylene chloride (0.5 mL). Triethylamine (0.34 mL, 2.5 mmol) was added, followed by N-boc 2-piperidinylmethanol (540 mg, 2.5 mmol). After 18 h at room temperature, the mixture was partitioned between ethyl acetate and a saturated aqueous solution of sodium bicarbonate (90 mL each). The ethyl acetate layer was washed with water (2×90 mL), brine (75 mL), then dried over sodium sulfate and concentrated. Purification by flash chromatography (a gradient from 10% to 20% ethyl acetate in hexanes as eluant) afforded 113 mg of the intermediate N-boc ester.

Part II: To a solution of the N-boc derivative prepared in part I (100 mg, 0.18 mmol) in methylene chloride (5 mL) at 0° C. was added trifluoroacetic acid (5 mL). After stirring at 0° C. for 30 min, the mixture was partitioned between methylene chloride and saturated aqueous sodium bicarbonate (100 mL each). The methylene chloride was washed with water and brine, then dried over sodium sulfate and concentrated. Purification by flash chromatography (5% isopropanol in chloroform as eluant) afforded 54 mg of the title compound as a solid.

m.p.: 144°–146° C.

Analysis: (C$_{28}$H$_{37}$N$_3$O$_3$)+1.0 water calc. C, 69.81; H, 8.18; N, 8.73 found C, 69.84; H, 7.90; N, 8.61

HPLC: (method A) R$_t$=10.30 min.

FABMS: m/z=464 (M$^+$+H)

$^1$H NMR: consistent with the structure.

EXAMPLE 36

1-(2-methylphenyl)-4-[(4,7,7-trimethyl-3-oxobicyclo [2.2.1]hept-2-yl)sulfonyl]-piperazine

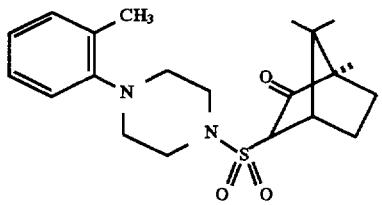

To a solution of o-tolylpiperazine (560 mg, 3.18 mmol) in methylene chloride (10 mL) at 0° C. was added (+) camphor-α-sulfonyl chloride (prepared by the mute of M. Frerejacque Comp. Rend. 1926, 187, p. 895, 810 mg, 3.18 mmol). Triethylamine was added until the pH was approximately 9. After 1 h, the mixture was diluted with methylene chloride (50 mL), then washed with water (2×50 mL) and brine, then dried over sodium sulfate and concentrated. Purification by flash chromatography (3:1 hexanes: ethyl acetate as eluant) afforded 860 mg of the title compound as a white amorphous foam.

TLC: Rf (3:1 hexanes:ethyl acetate)=0.56

Analysis: (C$_{21}$H$_{30}$N$_2$O$_3$S) calc. C, 64.58; N, 7.74; H, 7.17 found C, 64.88; N, 7.91; H, 7.01

FABMS: m/z=391 (M$^+$+H)

$^1$H NMR: consistent with structure.

EXAMPLE 37

1-((7,7-Dimethyl-2-oxo-bicyclo(2.2.1)heptan-1-yl) methanesulfonyl)-4-(2-methylphenyl )piperazine

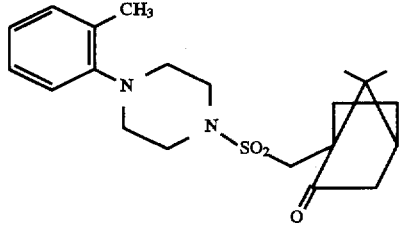

To a stirred, 0° C. solution of 1-(o-tolyl) piperazine hydrochloride (50.0 g; 235 mmol) and TEA (83 mL; 590 mmol) in chloroform (1000 mL) was added (+)-10-camphorsulfonyl chloride (65.5 g; 260 mmol). The solution was stirred at 0° C. for 1 h and then at ambient temperature for 3 h. The solution was extracted with 5% aqueous HCl (2×500 mL), water (500 mL), and saturated aqueous NaHCO$_3$ (2×500 mL). The organic phase was dried (MgSO$_4$), filtered, and the solvent was removed under reduced pressure. The resulting solid was recrystallized from methanol to give the title compound, mp 112°–114° C. (69 g; 75%).

Anal: (C$_{21}$H$_{30}$N$_2$O$_3$S) calc.: C, 64.57; H, 7.74; N, 7.17 found: C, 64.52; H, 7.68; N, 6.99

TLC: R$_f$0.49 (75:25 hexane/ethyl acetate)

HPLC (method A): retention time 10.33 min

FAB MS: m/z 391 (M$^+$+H)

$^1$H NMR (300 MHz, CDCl$_3$): δ7.2 (m, 2H), 7.0 (m, 2H), 3.45 (m, 4H), 3.40 (d, J=16 Hz, 1H), 3.0 (m, 4H), 2.57 (m,

1H), 2.40 (dr, Jd=14 Hz, Jt=3 Hz, 1H), 2.30 (s, 3H), 2.10 (m, 2H), 1.96 (d, J=14 Hz, 1H), 1.67 (m, 1H), 1.44 (m, 1H), 1.18 (s, 3H), 0.91 (s, 3H)

EXAMPLE 38

1-((7,7-Dimethyl-2-exo-hydroxy-2-endo-(1-cyano)ethyl-bicyclo(2.2.1)heptan-1-yl)methanesulfonyl)-4-(2-methylphenyl)piperazine

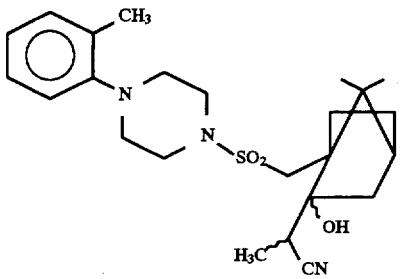

To a stirred, −78° C. solution of diisopropylamine (21.0 mL; 150 mmol) in THF (350 mL) was added n-butyllithium (60 mL of a 2.5M solution in hexane; 150 mmol). The solution was warmed to 0° C. for 15 min, then cooled to −78° C. A solution of propionitrile (10.1 mL; 141 mmol) in THF (75 mL) was added dropwise, and the resulting solution was stirred at −78° C. for 45 min. A −78° C. solution of 1-((7,7-dimethyl-2-oxo-bicyclo(2.2.1)heptan-1-yl)methanesulfonyl)-4-(2-methylphenyl)piperazine (50.0 g; 128 mmol) in THF (350 mL) was added via cannula, and the resulting solution was stirred at −78° C. for 5 min. A solution of 5:1 THF/water (100 mL) was added and the mixture was warmed to ambient temperature. The mixture was diluted with EtOAc (500 mL) and washed with 5% aqueous citric acid (2×500 mL), and brine (250 mL). The organic phase was dried (MgSO₄), filtered, and the solvents were removed under reduced pressure to give a foam. The major isomer by TLC was obtained by crystallization from ether, mp 163°–165° C.

Anal: ($C_{24}H_{35}N_3O_3S$) calc. C, 64.69; H, 7.92; N, 9.43 found C, 64.72; H, 7.99; N, 9.35

TLC: $R_f$ 0.31 (75:25 hexane/ethyl acetate)

HPLC (method A): retention time 10.20 min

FAB MS: m/z 446 (M⁺+H)

¹H NMR (300 MHz, CDCl₃): δ7.19 (m, 2H), 3.70 (d, J=15 Hz, 1H), 3.68 (s, 1H), 3.49 (m, 4H), 3.38 (d, J=15 Hz, H), 2.75 (q, J=7 Hz, 1H), 2.30 (s, 2H), 2.05 (m, 2H), 1.7–1.9 (m, 3H), 1.47 (d, J=7 Hz, 3H), 1.41 (d, J=12 Hz, 1H), 1.40 (s, 3H), 1.15 (s, 3H), 1.04 (m, 1H)

EXAMPLE 39

1-((7,7-Dimethyl-2-exo-hydroxy-2-endo-2-(1-amino)-propylbicyclo(2.2.1)heptan-1-yl)methanesulfonyl)-4-2-methylphenyl)piperazine

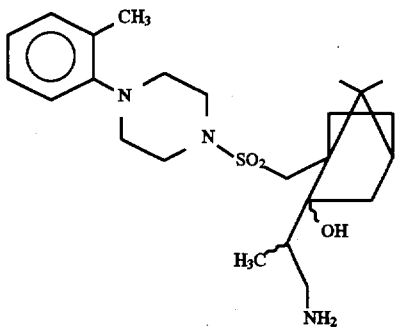

To a stirred, −78° C. solution of 1-((7,7- dimethyl-2-exo-hydroxy-2-endo-(1-cyano)ethyl-(2.2.1) bicycloheptan-1-yl) methanE-sulfonyl)-4-(2-methylphenyl)piperazine (25.0 g; 56.2 mmol) in THF (350 mL) was added dropwise a 1.0M solution of LAH in THF (170 mL; 170 mmol). The resulting solution was stirred at −78° C. for 1 h, and then warmed to 0° C. for 3 h. Ether (300 mL) was added, followed by the slow drop-wise addition of 5M NaOH solution (35 mL). The resulting suspension was warmed to ambient temperature and stirred for 1 h. EtOAc (250 mL) was added and stirring was continued for 30 min. The solids were removed by filtration through Celite and washed with EtOAc. The filtrate solvents were removed under reduced pressure to give a foam. The title compound was obtained by crystallization from methanol (17.2 g; 68%), mp 172°–174° C.

Anal: ($C_{24}H_{39}N_3O_3S$) calc. C, 64.11; H, 8.74; N, 9.35 found C, 64.09; H, 8.88; N, 9.31

TLC: $R_f$ 0.50 (95:5:0.5 CHCl₃/MeOH/NH₄OH)

HPLC (method A): retention time 9.80 min

FAB MS: m/z 450 (M⁺+H)

¹H NMR (300 MHz, CDCl₃): δ7.20 (m, 2H), 7.05 (m, 2H), 2.32 (s, 3H), 1.13 (d, J=6 Hz, 3H), 1.11 (s, 3H), 1.02 (s, 3H)

EXAMPLE 40

1-((7,7-Dimethyl-2-exo-hydroxy-2-endo-2-(1-(1-prolyl)-amino)propylbicyclo(2.2.1)heptan-1-yl)methanesulfonyl)-4-(2-methylphenyl)piperazine

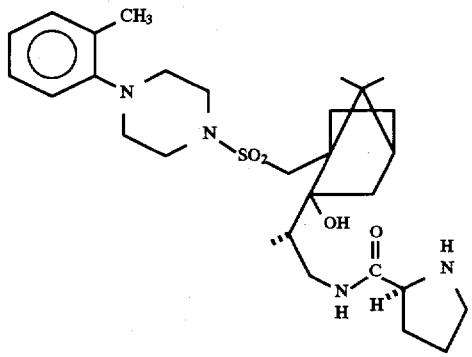

To a stirred solution of 1-((7,7-dimethyl-2-exo-hydroxy-2-endo-2-(1-amino) propyl-(2.2.1)bicycloheptan-1-yl)

methanesulfonyl)-4-(2-methylphenyl)piperazine (2.00 g; 4.45 mmol) in DMF (30 mL) was added N$^\alpha$-Fmoc-L-proline (1.58 g; 4.68 mmol), BOP (2.17 g; 4.90 mmol), and DIEA (1.71 mL; 9.80 mmol). After 16 h, diethylamine (6 mL) was added and the solution was stirred at ambient temperature for 3 h. The solvents were removed under reduced pressure and the residue was purified by preparative reverse phase HPLC using an acetonitrile-water gradient containing 0.1% TFA. The TFA salt of title compound was obtained as a lyophilized powder.

Anal: ($C_{29}H_{46}N_4O_4S$) calc. C, 52.48; H, 6.50; N, 7.56 found C, 52.46; H, 6.50; N, 7.69

1.7 TFA, 0.05 $H_2O$

TLC: $R_f$=0.45 (90:10:1 $CHCl_3$:MeOH:$NH_4OH$)

HPLC (method A): retention time 8.60 min

FAB MS: m/z 547 ($M^+$+H)

$^1$H NMR (400 MHz, $CDCl_3$): d 7.55 (br t, 1H), 7.18 (m, 2H), 7.03 (m, 2H), 2.31 (s, 3H), 1.14 (s, 3H), 1.02 (s, 3H), 0.99 (d, J=7 Hz, 3H)

EXAMPLE 41

1-((7,7-Dimethyl-2-exo-hydroxy-2-endo-2-(1-(1-N-(ethoxycarbonylpropyl)prolyl)amino)propyl -bicyclo (2.2.1)heptan-1-yl)methanesulfonyl)-4-(2-methylphenyl)piperazine

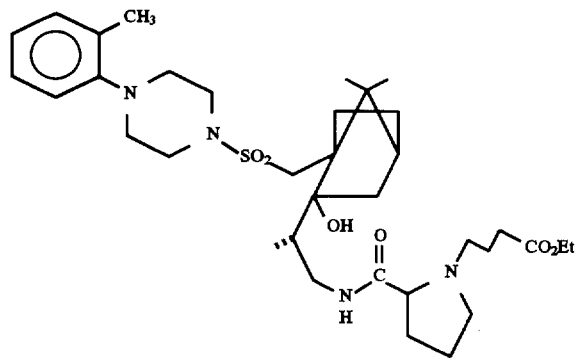

To a stirred solution of 1-((7,7-dimethyl-2-exo-hydroxy-2-endo-2-(1-(L-prolyl)amino) propyl-(2.2.1)bicycloheptan-1-yl)methane-sulfonyl)-4-(2-methylphenyl)piperazine (1.50 g; FW=679; 2.21 mmol) in DMF (15 mL) was added ethyl 4-bromobutyrate (538 mg; 2.76 mmol), and DIEA (1.15 mL; 6.63 mmol). After 72 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{35}H_{56}N_4O_6S$) calc. C, 51.99; H, 6.48; N, 6.17 found C, 52.01; H, 6.33; N, 6.17

2.1 TFA, 0.1 $H_2O$

TLC: $R_f$=0.40 (95:5 $CHCl_3$:MeOH)

HPLC (method A): retention time 10.23 min

FAB MS: m/z 661 ($M^+$+H)

$^1$H NMR (400 MHz, $CDCl_3$): d 8.55 (m, 1H), 7.20 (m, 2H), 7.08 (m, 2H), 2.35 (s, 3H), 1.25 (t, J=6 Hz, 3H), 1.14 (s, 3H), 1.03 (overlapping s and d, 6H)

EXAMPLE 42

1-((7,7-Dimethyl-2-exo-hydroxy-2-endo-2-(1-(1-N-(3-carboxypropyl)prolyl)amino)propyl-bicyclo (2.2.1)heptan-1-yl)methanesulfonyl)-4-(2-methylphenyl) piperazine

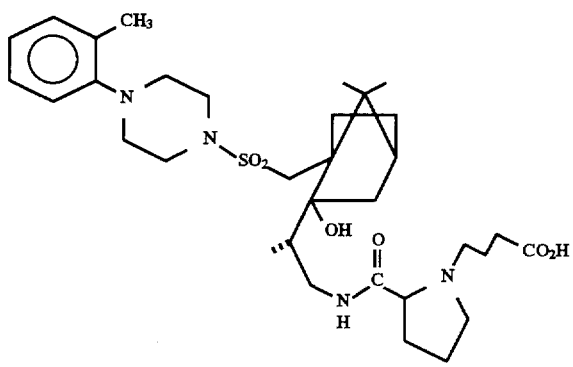

To a stirred solution of 1-((7,7-dimethyl-2-exo-hydroxy-2-endo-2-(1-(L-N-(ethoxycarbonylpropyl) prolyl)amino) propyl-(2.2.1)bicycloheptan-1-yl)methane- sulfonyl)-4-(2-methylphenyl)piperazine (1.00 g; FW=909; 1.10 mmol) in THF (15 mL) was added 1M NaOH solution (1.0 mL; 4.0 mmol) until a pH 10 solution persisted for 1 h. The solution was acidified to pH 7 by addition of citric acid and the solvents were removed under reduced pressure. The residue was dissolved in dichloromethane (75 mL) and washed with water (3×25 mL), dried ($MgSO_4$), filtered, and the solvent was removed under reduced pressure. The residue was lyophilized from dioxane-water to give the title compound as a white powder.

Anal: ($C_{33}H_{52}N_4O_6S$) calc. C, 59.78; H, 8.25; N, 6.94 found C, 59.86; H, 7.98; N, 6.92

0.1 Na citrate, 1.65 dioxane

TLC: $R_f$=0.35 (80:20:2 $CHCL_3$:MeOH:NH4OH)

HPLC (method A): retention time 9.24 min

FAB MS: m/z 633 ($M^+$+H)

$^1$H NMR (400 MHz, $CDCl_3$): d 7.55 (br s, 1H), 7.18 (m, 2H), 7.03 (m, 2H), 2.31 (s, 3H), 1.15 (s, 3H), 1.04 (s, 3H), 0.98 (d, J=6 Hz, 3H)

EXAMPLE 43

1-((7,7-Dimethyl-2-exo-hydroxy-2-endo-2-(1-(4(5)-imidazolylacetyl)amino)propyl-bicyclo(2.2.1)heptan-1-yl)methanesulfonyl)-4-(2-methylphenyl)piperazine

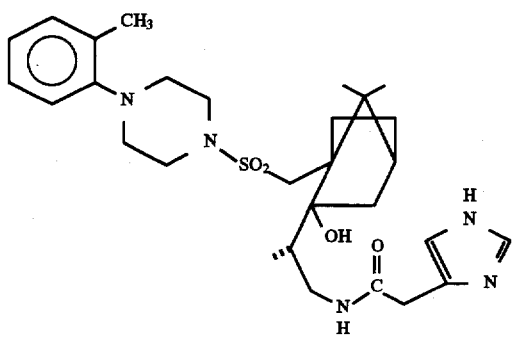

To a stirred solution of 1-((7,7-dimethyl-2-exo-hydroxy-2-endo-2-(1-amino)propyl-(2.2.1)bicyclo-heptan-1-yl)methanesulfonyl)-4-(2-methylphenyl)piper-azine (1.50 g; 3.34 mmol) in DMF (15 mL) was added 4(5)-imidazole acetic acid hydrochloride (679 mg; 4.18 mmol), BOP (1.85 g; 4.18 mmol), and DIEA (2.18 mL; 12.5 mmol). After 16 h, the solvent was removed under reduced pressure. The residue was dissolved in EtOAc (100 mL) and washed with saturated aqueous $NaHCO_3$ solution (2×50 mL) and water (2×50 mL). The organic phase was dried ($MgSO_4$), filtered, and the solvent was removed under reduced pressure. The residue was purified by pressurized silica gel column chromatography using 92:8:0.8 ($CHCl_3$:MeOH:$NH_4OH$) as eluant. The title compound crystallized from EtOAc, mp 159°–163° C.

Anal: ($C_{29}H_{43}N_5O_4S$) calc. C, 62.45; H, 7.77; N, 12.56 found C, 62.88; H, 7.68; N, 12.79

TLC: $R_f$ 0.4 (90:10:1 $CHCl_3$/MeOH/$NH_4OH$)

HPLC (method A): retention time 8.72 min

FAB MS: m/z 558 ($M^+$+H)

$^1$H NMR ($CDCl_3$): d 7.57 (s, 1H), 7.2 (m, 3H), 7.0 (m, 2H), 6.88 (s, 1H), 3.55 (m, 2H), 3.4 (m, 5H), 2.95 (m, 4H), 2.87 (d, J=15 Hz, 1H), 2.31 (s, 3H), 1.71 (t, J=4 Hz, 1H), 1.52 (d, J=13 Hz, 1H), 1.15 (s, 3H), 1.03 (s, 3H), 0.97 (d, J=6 Hz, 3H)

EXAMPLE 44

1-((7,7-Dimethyl-2-exo-hydroxy-2-endo-2-(1-(quinuclidin-3-yl-carbonyl)amino)propyl-bicyclo(2.2.1)heptan-1-yl)methanesulfonyl)-4-(2-methylphenyl)piperazine

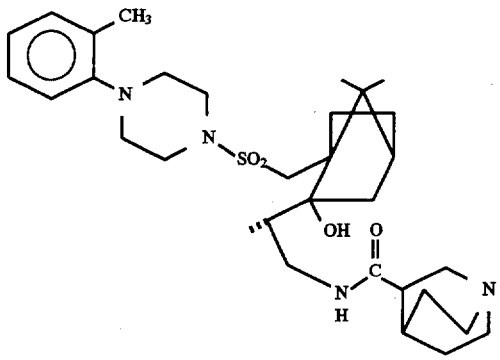

To a stirred solution of 1-((7,7-dimethyl-2-exo-hydroxy-2-endo-2-(1-amino)propyl-(2.2.1)bicycloheptan-1-yl)methanesulfonyl)-4-(2-methylphenyl)piperazine (2.00 g; 4.45 mmol) in DMF (50 mL) was added quinuclidine-3-carboxylic acid hydrochloride (938 mg; 4.90 mmol BOP (2.17 g; 4.90 mmol), and DIEA (2.56 mL; 14.7 mmol). After 16 h, the solvent was removed under reduced pressure. The residue was purified by preparative reverse phase HPLC using an acetonitrile-water gradient containing 1% acetic acid. The acetate salt of the title compound (1:1 mixture of diastereomers) was obtained as a lyophilized powder.

Anal: ($C_{32}H_{50}N_4O_4S$) calc. C, 60.39; H, 8.58; N, 8.39 found C, 60.41; H, 8.19; N, 8.58

0.8 $CH_3CO_2H$, 1.85 $H_2O$

TLC: $R_f$=0.65 (80:20:2 $CHCl_3$:MeOH:$NH_4OH$)

HPLC (method A): retention time 8.68 min

FAB MS: m/z 587 ($M^+$+H)

$^1$H NMR (300 MHz, $CDCl_3$): d 7.19 (m, 2H), 7.02 (m, 2H), 2.30 (s, 3H), 1.16 (s, 3H), 1.03 (overlapping s and d, 6H)

EXAMPLE 45

1-((7,7-Dimethyl-2-exo-hydroxy-2-endo-2-(1-(1-carboxymethylquinuclidin-3-yl-carbonyl)amino)propyl-bicyclo-(2.2.1)heptan-1-yl)methanesulfonyl)-4-(2-methylphenyl)piperazine

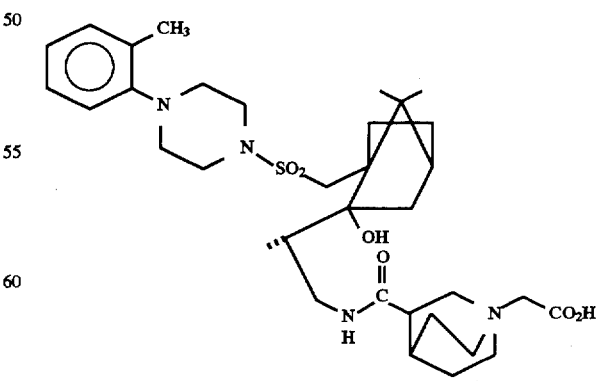

To a stirred solution of 1-((7,7-dimethyl-2-exo-hydroxy-2-endo-2-(1-(quinuclidin-3-yl-carbonyl)amino)-propyl-

47

(2.2.1)bicycloheptan-1-yl)methane-sulfonyl)-4-(2-methylphenyl)piperazine (1.50 g; FW=668; 2.25 mmol) in DMF (30 mL) was added iodo-acetic acid (543 mg; 2.92 mmol) and DIEA (0.43 mL; 2.48 mmol). After 16 h, TLC showed complete con-sumption of starting material. The solvent was removed under reduced pressure and the residue was purified by preparative reverse phase HPLC using an acetonitrile-water gradient containing 1% acetic acid. The title compound, as a 1:1 mixture of diastereomers, was obtained as a lyophilized powder.

Anal: ($C_{34}H_{52}N_4O_4S$) calc. C, 60.52; H, 8.18; N, 8.04 found C, 60.52; H, 7.98; N, 8.15

0.55 $CH_3CO_2H$, 0.95 $H_2O$

TLC: $R_f$-0.20 (80:10:2 $CHCl_3$:MeOH:$NH_4OH$)

HPLC (method A): retention time 8.73 min

FAB MS: m/z 647 ($M^+$+H)

$^1$H NMR (TFA salt; 400 MHz, $CDCl_3$): d 7.46 (br s, 1H), 7.19 (m, 2H), 7.02 (m, 2H), 2.30 (s, 3H), 1.13 (s, 3H), 1.02 (s, 3H), 0.98 (d, J=6 Hz, 3H)

EXAMPLE 46

1-((7,7-Dimethyl-2-exo-hydroxy-2-endo-2-(1-(2-methoxycarbonylethyl)-amino)propyl-bicyclo(2.2.1)heptan-1-yl)methanesulfonlyl)-2-methylphenyl)piperazine

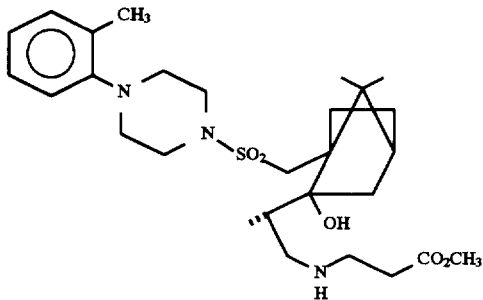

To a stirred solution of 1-((7,7-dimethyl-2-exo-hydroxy-2-endo-2-(1-amino)propyl-(2.2.1)bicycloheptan-1-yl)methanesulfonyl)-4-(2-methylphenyl)piperazine (100 mg; 0.22 mmol) in 1:1 DMF-MeOH (3 mL) was added methyl acrylate (0.020 mL; 0.22 mmol). After 16 h, the solvents were removed under reduced pressure and the residue was purified by preparative reverse phase HPLC using an acetonitrile-water gradient containing 0.1% TFA. The TFA salt of the title compound was obtained as a lyophilized powder.

Anal: ($C_{28}H_{45}N_3O_5S$) calc. C, 53.03; H, 6.88; N, 6.06 found C, 53.01; H, 6.90; N, 6.01

1.3 TFA, 0.5 $H_2O$

TLC: $R_f$=0.35 (95:5 ($CHCl_3$:MeOH)

HPLC (method A): retention time 9.04 min

FAB MS: m/z 536 ($M^+$+H)

$^1$H NMR (300 MHz, $CDCl_3$): d 7.20 (m, 2H), 7.03 (m, 2H), 3.72 (s, 3H), 2.32 (s, 3H), 1.19 (d, J=6 Hz, 3H), 1.15 (s, 3H), 0.98 (s, 3H)

EXAMPLE 47

1-((7,7-dimethyl-2-exo-hydroxy-2-endo-2-(1-bis-(2-methoxycarbonylethyl)amino)propyl-bicyclo(2.2.1)heptan-1-yl)methanesulfonyl)-4-(2-methylphenyl)piperazine

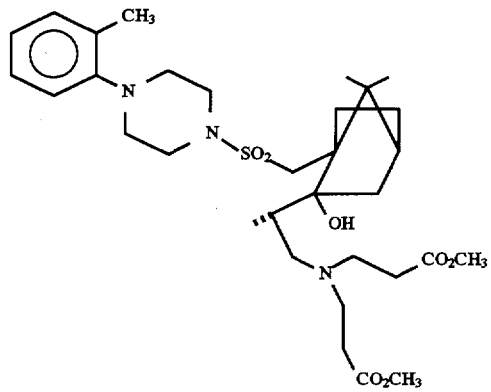

To a stirred solution of 1-((7,7-dimethyl-2-exo-hydroxy-2-endo-2-(1-amino)-propyl-(2.2.1)bicycloheptan-1-yl)methanesulfonyl)-4-(2-methylphenyl)piperazine (100 mg; 0.22 mmol) in 1:1 DMF-MeOH (3 mL) was added methyl acrylate (0.080 mL); 0.89 mmol). After 16 h, the solvents were removed under reduced pressure and the residue was purified by pressurized silica gel chromatography using 3:1 hexane-ethyl acetate as eluant. The title compound was obtained as a foam from hexane.

Anal: ($C_{32}H_{51}N_3O_7S$) Calc: C 61.81, H 8.27, N 6.76 Found: C 61.55, H 8.13, N 6.55

TPC: $R_f$=0.40 (1:3 EtOAc:hexanes)

HPLC (method A): rentention time 9.71 min

FAB MS: m/z 622 ($M^+$+H)

$^1$H NMR (300 MHz, $CDCl_3$): d 7.19 (m, 2H), 7.02(m, 2H), 3.66 (s, 6H), 2.31 (s, 3H), 1.13 (s, 3H), 1.00 (overlapping a and d, 6H)

EXAMPLE 48

1-((7,7-dimethyl-2-exo-hydroxy-2-endo-ethenyl-bicyclo(2.2.1)heptan-1-yl)methanesulfonyl)-4-2-methyl-phenyl)piperazine

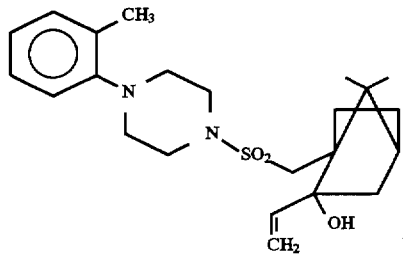

To a -78° C. stirred 1.0M solution of vinyl magnesium chloride in THF (25 mL; 25 mmol) was added a -78° C. solution of 1-((7,7-dimethyl-2-oxo-(2.2.1) bicycloheptan-1-yl)methanesulfonyl)-4-(2-methylphenyl)-piperazine (5.00 g; 12.8 mmol) in THF (100 mL) via cannula. The resulting solution was stirred under argoln overnight, allowing the cooling bath to warm to ambient temperature. The reaction was quenched by addition of 2% aqueous HCl (50 mL), and the mixture was partitioned between ethyl acetate and water. The organic phase was washed with aqueous NaHCO$_3$ and brine, dried over MgSO$_4$, and filtered. The solvents were removed under reduced pressure and the residue was purified by pressurized silica gel chromatography using 4:1 hexane-ethyl acetate as eluant. The title compound was obtained as a white foam from ether.

Anal: (C$_{23}$H$_{34}$N$_2$O$_3$S) 0.06 H$_2$O Calc: C 65.82, H 8.19, N 6.67 Found: C 65.99, H 8.42, N 6.63

TLC: R$_f$-0.36 (1:5 EtOAc:hexanes)

HPLC (method A): rentention time 11.41 min

FAB MS: m/z 419 (M$^+$+H)

$^1$H NMR (400 MHz, CDCl$_3$): d 7.20 (m, 2H), 7.02 (m, 2H), 6.48 (dd, 1H), 5.30 (d, 1H), 5.17 (d, 1H), 2.32 (s, 3H), 1.22 (s, 3H), 0.94 (s, 3H).

EXAMPLE 49

1-((7,7-dimethyl-2-(2-chloro)ethylidinebicyclo-(2.2.1)heptan-1-yl)methanesulfonyl)-4-(2-methyl-phenyl)piperazine

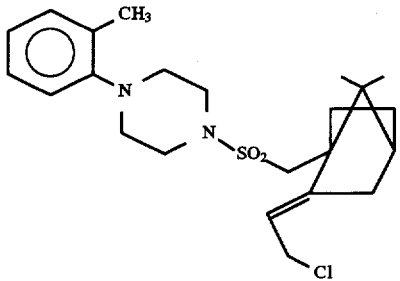

To a 0° C. stirred solution of 1-((7,7-dimethyl-2-exo-hydroxy-2-endo-ethenyl-(2.2.1)bicycloheptan-1-yl) methanesulfonyl)-4-(2-methylphenyl)piperazine (2.90 g; 6.94 mmol) in THF (100 mL) was added triethylamine (1.50 mL; 10.7 mmol) and DMF (0.58 mL;7.5 mmol). Thionyl chloride (0.66 mL; 9.1 mmol) was added dropwise, and the resulting solution was stirred for 18 h, allowing the cooling bath to warm ambient temperature. The solvents were removed under reduced pressure and the residue was dissolved in theyl acetate (150 mL) and washed with 5% aqueous HCl (75 mL), water (75 mL) and aqueous NaHCO$_3$ (100 mL). The organic phase was dried (MgSO$_4$). filtered, and the solvent was removed under reduced pressure. The residue was purified by pressurized silica gel column chromatography using 4:1 hexane-ethyl acetate as eluant. The title compound was obtained as a white foam.

Anal: (C$_{23}$H$_{33}$ClN$_2$O$_2$S) 0.6 H$_2$O Calc: C 65.82, H 8.19, N 6.67 Found: C 65.99, H 8.42, N 6.63

$^1$H NMR (400 MHz, CDCl$_3$): d 7.20 (m, 2H), 7.03 (m, 2H), 5.87 (m, 1H), 4.10 (ABX, 2H), 2.32 (s, 3H), 1.00 (s, 3H), 0.82 (s, 3H)

EXAMPLE 50

1-((7,7-dimethyl-2-(2-isobutylamino)ethylidine-bicyclo(2.2.1)heptan-1-yl)methanesulfonlyl)-4-(2-methylphenyl)piperazine

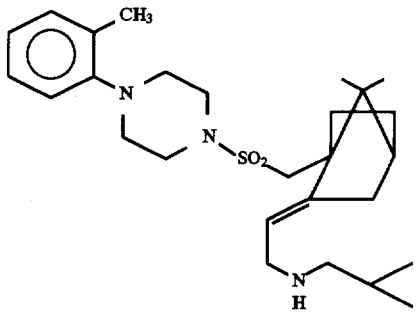

To a stirred solution of 1-((7,7-dimethyl-2-(2-chloro) ethylidine-(2.2.1)bicycloheptan-1-yl)methanesulfonyl)-4-(2-methylphenyl)piperazine (200 mg; 0.46 mmol) in MeOH (2 mL) was added isobutylamine (0.5 mL; 5 mmol). After being stirred for 18 h, the solvents were removed under reduced pressure and the residue was purified by preparative reverse phase HPLC using an acetonitrile-water gradient containing 0.1% TFA. The TFA salt of the title compound was obtained as a lyophilized powder.

Anal: (C$_{27}$H$_{41}$N$_3$O$_2$S) 2.0 H$_2$O; 1.0 TFA

TLC: R$_f$-0.30 (95:5:0.5 CHCl$_3$:MeOH:NH$_4$OH)

HPLC (method A): rentention time 9.78 min

FAB MS: m/z 474 (M$^+$+H)

$^1$H NMR (400 MHz, CD$_3$OD): d 7.20 (m, 3H), 7.03 (t, 1H), 5.78 (m, 1H), 2.35 (s, 3H), 1.13 (d, J=7 Hz, 6H), 1.12 (s, 3H), 0.88 (s, 3H)

EXAMPLE 51

1-((7,7-dimethyl-2-(2-azido)ethylidine-bicyclo-(2.2.1)heptan-1-yl)methanesulfonyl)-4-(2-methyl-phenyl)piperazine

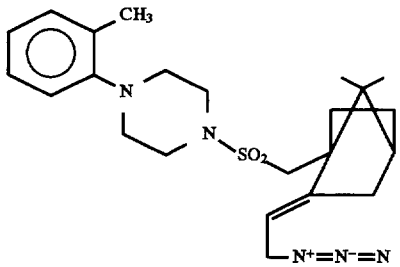

To a stirred solution of 1-((7,7-dimethyl-2-exo-hydroxy-2-(2-chloro)ethylidine-(2.2.1)bicyclo-heptan-1-yl) methanesulfonyl)-4-(2-methylphenyl)piperazine (3.58 g;8.19 mmol) in DMSO (50 mL) and THF (45 mL) was added a solution of sodium azide (5.3 g; 82 mmol) in water (20 mL). After 24 h, the solvents were removed under reduced pressure, the residue was suspended in dichloromethane (100 mL) and washed with water (3×50 mL). The organic phase was dried (MgSO$_4$), filtered, and the solvent was removed under reduced pressure to give a solid.

Anal: (C$_{23}$H$_{33}$N$_5$O$_2$S) Calc: C 62.27, H 7.50, N 15.79 Found: C 62.41, H 7.54, N 15.60

TLC: R$_f$0.75 (70:30 hexane-ethyl acetate)

HPLC (method A): rentention time 12.50 min

FAB MS: m/z 444 (M$^+$+H)

$^1$H NMR (300 MHz, CDCl$_3$): d 7.20 (m, 2H), 7.02 (m, 2H), 5.79 (m, 1H), 3.78 (ABX, 2H), 2.32 (s, 3H), 0.85 (s, 3H)

EXAMPLE 52

1-((7,7-dimethyl-2-(2-amino)ethylidine-bicyclo-(2.2.1)heptan-1-yl)methanesulfonyl)-4-(2-methyl-phenyl)piperazine

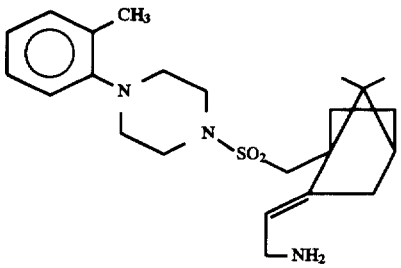

To a stirred solution of 1-((7,7-dimethyl-2-exo-hydroxy-2-(2-azido)ethylidine-(2.2.1)bicyclo-heptan-1-yl) methanesulfonyl)-4-(2-methylphenyl)piperazine (3.85 g; 8.69 mmol) in THF (150 mL) and water (3 mL) was added triphenylphosphine (2.50 g; 9.56 mmol). After 14 h, the solvents were removed under reduced pressure. The residue was dissolved in ethyl acetate (150 mL) and extracted with 5% aqueous HCl (3×75 mL). The combined acid extracts were washed with ethyl acetate (50 mL) and then made basic by adding solid sodium hydroxide to pH 12. The aqueous phase was extracted with chloroform (3×50 mL) and the combined organic phases were dried (MgSO$_4$), filtered, and the solvent was removed under reduced pressure. The residue was purified by pressurized silica gel column chromatography using a gradient elution of 99:1 to 85:15 chloroform-methanol. The title compound was obtained as a solid.

Anal: (C$_{23}$H$_{35}$N$_3$O$_2$S) 0.5 H$_2$O Calc: C 64.75; H 8.51; N 9.85; Found: C 64.59; H 7.51; N 9.71

TLC: R$_f$0.56 (95:5:0.5 CHCl$_3$-MeOH-NH$_4$OH)

HPLC (method A): retention time 10.38 min

FAB MS: m/z 418 (M$^+$+H)

$^1$H NMR (CDCl$_3$): $^1$H NMR (300 MHz, CDCl$_3$): 87.16 (m, 2H), 7.00 (m, 2H), 5.61 (m, 1H), 3.43 (m, 4H), 3.26 (d, J=6.6 Hz, 2H), 1.18 (d, J=14.1 Hz, 1H0, 1.97 (m, 4H), 2.92 (d, J=14.1 Hz, 1H), 2.35 (m, 1H), 2.31 (s, 3H), 1.7–1.8 (m, 3H), 1.70 (m, 1H), 1.25 (m, 1H), 0.99 (s, 3H), 0.81 (s, 3H).

EXAMPLE 53

1-((7,7-dimethyl-2-(2-(4(5)-imidazolylacetyl)amino) -ethylidine-bicyclo(2.2.1)heptan-1-yl)methane- sulfonyl)-4-(2-methylphenyl)piperazine

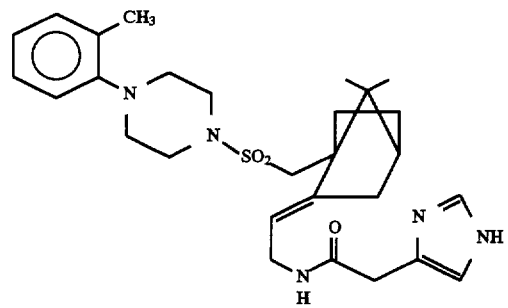

To a stirred solution of 1-((7,7-dimethyl-2-exo-hydroxy-2-(2-amino)ethylidine-(2.2.1)bicyclo-heptan-1-yl) methanesulfonyl)-4-(2-methylphenyl)piperazine (0.20 g; 0.48 mmol) in DMF (5 mL) was added BOP (265 mg; 0.60 mmol), 4-imidazoleacetic acid hydrochloride (115 mg; 0.72 mmol) and DIEA (0.38 mL; 2.2 mmol). After 14 h, the solvents were removed under reduced pressure, the residue was suspended in ethyl acetate (50 mL) and washed with aqueous NaHCO$_3$ (2×25 mL) and water (2×25 mL). The organic phase was dried (MgSO$_4$), filtered and the solvent was removed under reduced pressure. The residue was purified by preparative reverse phase HPCL using an acetonitrile-water gradient containing 0.1% TFA. The TFA salt of the title compound was obtained as a lyophilized powder.

Anal: (C$_{28}$H$_{39}$N$_5$O$_3$S); 0.5 H$_2$O; 2.0 TFA; Calc: C 50.38; H 5.55; N 9.18 Found: C 50.40; H 5.55; N 9.40

TLC: R$_f$0.42 (95:5:0.5 CHCl$_3$-MeOH-NH$_4$OH)

HPLC (method A): retention time 8.76 min.

FAB MS: m/z 526 (M$^+$+H)

$^1$H NMR (400 MHz, CDCl$_3$): d 8.40 (s, 1H), 7.58 (br m, 1H), 7.22 (m, 3H), 7.10 (m, 2H), 5.57 (br t, 1H), 2.37 (s, 3H), 0.97 (s, 3H), 0.76 (s, 3H)

EXAMPLE 54

1-((7,7-Dimethyl-2-spiro-epoxy-bicyclo(2.2.1) heptan-1-yl)methanesulfonyl)-4-(2-methylphenyl) piperazine

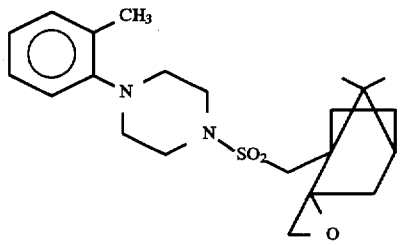

To a stirred 0° C. suspension of trimethyl-sulfoxonium iodide (6.78 g; 30.8 mmol) in THF (100 mL) was added n-butyllithium (11.1 mL of a 2.5M solution in hexane; 27.7 mmol). After 4 h at 0° C., a solution of 1-((7,7-dimethyl-2-oxo-(2.2.1)bicyclo-heptan-1-yl)methanesulfonyl)-4-(2-methylphenyl)piperazine (8.00 g; 20.5 mmol) in THF (50 mL). The resulting solution was stirred at 0° C. for 2 h, and then at ambient temperature for 18 h. The solvents were removed under reduced pressure, the residue was dissolved in ethyl acetate (150 mL) and washed with water (2×50 mL). The organic phase was dried (MgSO$_4$), filtered, and the solvent was removed under reduced pressure. The resulting solid was recrystallized from ether to give the title compound as white needles, mp 131°–133° C.

Anal: (C$_{22}$H$_{32}$N$_2$O$_2$S) calc. C, 65.31; H, 7.97; N, 6.92 found C, 65.09; H, 7.99; N, 6.86

0.5 H$_2$O

TLC: R$_f$0.62 (4:1 hexane-ethyl acetate)

HPLC (method A): retention time 11.50 min

FAB MS: m/z 405 (M$^+$+H)

$^1$H NMR (300 MHz, CDCl$_3$): d 7.20 (m, 2H), 7.02 (m, 2H), 3.20 (d, J=5.4 Hz, 1H), 2.70 (d, J=5.4 Hz, 1H), 2.30 (s, 3H), 1.00 (s, 3H), 0.99 (s, 3H)

EXAMPLE 55

1-((7,7-Dimethyl-2-exo-hydroxy-2-endo-isobutylamino-methylbicyclo(2.2.1)heptan-1-yl) methanesulfonyl)-4-(2-methylphenyl)piperazine

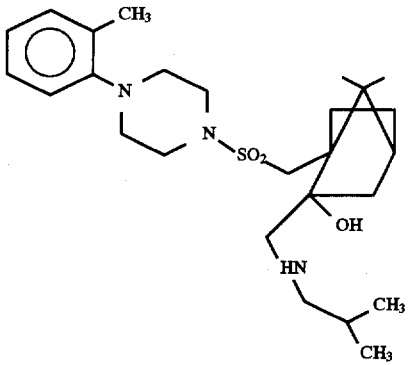

To a stirred solution of 1-((7,7-dimethyl-2-(spiroepoxy)-(2.2.1)bicycloheptan-1-yl)methanesulfonyl)-4-(2-methylphenyl)piperazine (200 mg; 0.495 mmol) in MeOH (3 mL) was added isobutylamine (0.5 mL; 5 mmol). After being stirred for 18 h, the solvents were removed under reduced pressure and the residue was purified by pressurized silica gel column chromatography using 98:2:0.2 chloroform-methanol-NH$_4$OH as eluant. The product was dissolved in methanol and to it was added several drops of 5% aqueous HCl. The solvents were removed under reduced pressure and the residue was triturated in ether to give the hydrochloride salt of the title compound as a white powder.

Anal: (C$_{26}$H$_{43}$N$_3$O$_3$S) calc. C, 57.00; H, 8.76; N, 7.67 found C, 57.03; H, 8.84; N, 7.61

1.0 HCl, 1.8 H$_2$O

TLC (free base): R$_f$0.20 (3:1 hexane-ethyl acetate)

HPLC (method A): retention time 9.54 min

FAB MS: m/z 478 (M$^+$+H)

$^1$H NMR (300 MHz, CDCl$_3$): d 7.20 (m, 2H), 7.02 (m, 2H), 2.30 (s, 3H), 1.10 (s, 3H), 0.95 (s, 3H), 0.90 (two doublets, 6H)

EXAMPLE 56

1-((7,7-Dimethyl-2-methoxycarbonyl-bicyclo(2.2.1) hept-2-en-1-yl)methanesulfonyl)-4-(2-methylphenyl) -piperazine

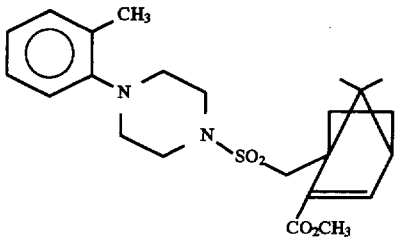

To a stirred, 0° C. solution of 1-((7,7-dimethyl-2-oxo-bicyclo(2.2.1)heptan-1-yl)methanesulfonyl)-4-(2-methylphenyl)piperazine (10.0 g; 25.6 mmol) in dichloromethane (500 mL) was added 2,6-di-t-butyl-4-methylpyridine (7.8 g; 38 mmol) and trifluoromethanesulfonic anhydride (5.4 mL; 32 mmol). The cooling bath was removed and the solution was stirred for 18 h. The mixture was filtered and the filtrate was washed with 5% aqueous HCl (2×100 mL), water (100 mL), and aqueous NaHCO$_3$ (2×100 mL). The organic phase was dried (MgSO$_4$), filtered and the solvent was removed under reduced pressure. The residue was purified by pressurized silica gel column chromatography using 9:1 hexane-ethyl acetate as eluant. The enol triflate product was obtained as a white foam and used as such in the next step. To a stirred solution of 1-((7,7-dimethyl-2-trifluoromethanesulfonyloxy-bicyclo(2.2.1)-hep-2-en-1-yl) methanesulfonyl)-4-(2-methylphenyl)-piperazine (10.5 g; 20.1 mmol) in 1:1 DMF-MeOH (150 mL) was added triethylamine (5.9 mL; 43 mmol), triphenyl-phosphine (317 mg; 1.21 mmol), and palladium(II)acetate (135 mg; 0.603 mmol). Carbon monoxide gas was bubbled through the solution for 15 min, and the reaction was kept under atmospheric pressure of CO for 18 h. The solvents were removed under reduced pressure and the residue was purified by pressurized silica gel column chromatography using 9:1 hexane-ethyl acetate as eluant. The title compound was obtained as a white foam from hexane.

Anal: (C$_{23}$H$_{32}$N$_2$O$_4$S) calc. C, 62.14; H, 7.50; N 6.30 found C, 61.65; H, 7.17; N, 6.12

0.67 H$_2$O

TLC: R$_f$=0.36 (1:5 EtOAc:hexanes)

HPLC (method A): retention time 11.34 min

FAB MS: m/z 433 (M$^+$+H)

$^1$H NMR (400 MHz, CDCl$_3$): d 7.20 (m, 2H), 7.03 (m, 2H), 6.88 (d, J=3 Hz, 1H), 3.72 (s, 3H), 2.33 (s, 3H), 1.09 (s, 3H), 1.01 (s, 3H)

EXAMPLE 57

1-((7,7-Dimethyl-2-carboxy-bicyclo(2.2.1)hept-2-en-1-yl)methanesulfonyl)-4-(2-methylphenyl)piperazine

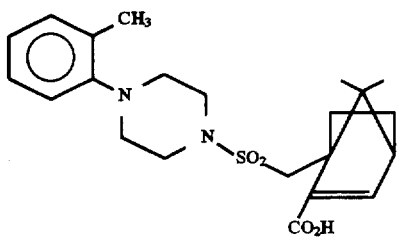

To a stirred solution of 1-((7,7-dimethyl-2-methoxycarbonyl-bicyclo(2.2.1)hept-2-en-1-yl)methanesulfonyl)-4-(2-methylphenyl)-piperazine (1.0 g; 2.3 mmol) in MeOH (10 mL) was added a solution of 4M aqueous KOH (2.0 mL; 8.0 mmol). After 18 h, the reaction was brought to pH 1 with 5% aqueous HCl, and the solvents were removed under reduced pressure. The residue was taken up in chloroform (50 mL) and washed with water (25 mL). The organic phase was dried (MgSO$_4$), filtered, and the solvent was removed under reduced pressure to give the hydrochloride salt of the title compound as a white foam.

Anal: ($C_{22}H_{30}N_2O_4S$) calc. C, 57.51; H, 6.91; N, 6.10 found C, 57.40; H, 6.87; N, 6.01

1.0 HCl, 0.25 H$_2$O

TPC: R$_f$=0.59 (92:8:0.1) CHCl$_3$:MeOH:HOAc)

HPLC (method A): retention time 9.77 min

FAB MS: m/z 419 (M$^+$+H)

$^1$H NMR (400 MHz, CD$_3$OD): d 7.30 (m, 3H), 7.20 (t, 1H), 6.89 (d, J=3 Hz, 1H), 2.43 (s, 3H), 1.11 (s, 3H), 1.00 (s, 3H)

EXAMPLE 58

1-((7,7-Dimethyl-2-(4-imidazolyl)ethylaminocarbonyl-bicyclo(2.2.1)hept-2-en-1-yl)methanesulfonyl)-4-(2-methylphenyl)piperazine

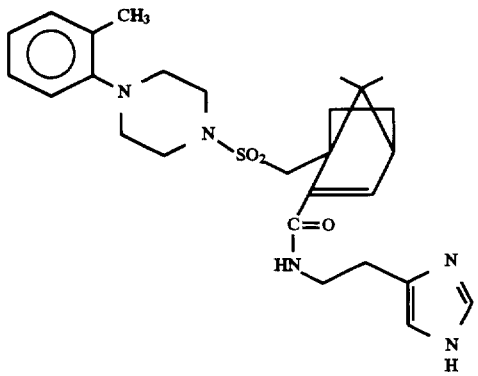

To a stirred solution of 1-((7,7-dimethyl-2-carboxybicyclo-(2.2.1)hept-2-en-1-yl)methanesulfonyl)-4-(2-methylphenyl)piperazine (100 mg; FW=460; 0.22 mmol) in DMF (5 mL) was added histamine (30 mg; 0.27 mmol), BOP (115 mg; 0.25 mmol) and DIEA (0.12 mL; 0.69 mmol). After 18 h, the solvent was removed under reduced pressure, the residue was purified by preparative reverse phase HPLC using an acetonitrile-water gradient containing 0.1% TFA. The TFA salt of the title compound was obtained as a lyophilized powder.

Anal: ($C_{27}H_{37}N_5O_3S$) calc. C, 49.35; H, 5.31; N, 9.22 found C, 49.25; H, 5.39; N, 9.20

2.1 TFA, 0.45 H$_2$O

HPLC (method A): retention time 8.16 min

FAB MS: m/z 512 (M$^+$+H)

$^1$H NMR (300 MHz, CD$_3$OD): d 8.80 (s, 1H), 7.40 (s, 1H), 7.18 (m, 2H), 7.05 (d, 1H), 6.99 (t, 1H), 6.41 (d, J=3 Hz, 1H), 2.31 (s, 3H), 1.08 (s, 3H), 0.98 (s, 3H)

EXAMPLE 59

1-((7,7-Dimethyl-2-endo-methoxycarbonyl-bicyclo-(2.2.1)heptan-1-yl)methanesulfonyl)-4-(2-methylphenyl)piperazine

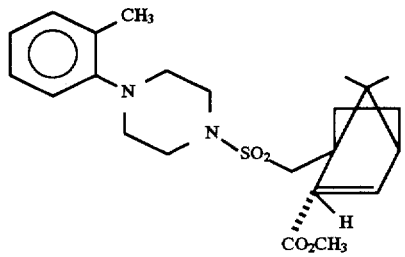

To a stirred, −78° C. solution of 1-((7,7-dimethyl-2-methoxy-carbonyl-bicyclo(2.2.1)hept-2-en-1-yl)methanesulfonyl)-4-(2-methyl-phenyl)piperazine (3.0 g; 6.9 mmol) in 2:1 THF-MeOH (50 mL) was added a solution of 0.1M samarium(II) iodide in THF (250.0 mL; 25.0 mmol). After 1 h, the reaction was warmed to ambient temperature and stirred for another 1 h. The solvents were removed under reduced pressure and the residue was partitioned between ethyl acetate (100 mL) and water (50 mL). The layers were separated and the organic phase was washed with water (50 mL), dried (MgSO$_4$), filtered, and evaporated to dryness under reduced pressure. By $^1$H NMR analysis, a 6:1 ratio of endo:exo products was obtained. The major, lower R$_f$ isomer (endo) was obtained in pure form by pressurized silica gel column chromatography using a gradient elution of 98:2 to 95:5 hexane-ethyl acetate, followed by crystallization from ethyl acetate. The title compound was obtained as white needles, mp 156°–158° C.

Anal: ($C_{23}H_{34}N_2O_4S$) found C, 63.31; H, 7.83; N, 6.43 calc. C, 63.56; H, 7.89; N, 6.45

TLC: R$_f$=0.44 (1:5 EtOAc:hexanes)

HPLC (method A): retention time 11.75 min

FAB MS: m/z 435 (M$^+$+H)

$^1$H NMR (400 MHz, CDCl$_3$): d 7.20 (m, 2H), 7.05 (m, 2H), 3.72 (s, 3H), 3.29 (ddd, 1H), 2.34 (s, 3H), 1.13 (s, 3H), 1.06 (s, 3H)

EXAMPLE 60

1-((7,7-Dimethyl-2-endo-carboxy-bicyclo(2.2.1)
heptan-1-yl)methanesulfonyl)-4-(2-methylphenyl)
piperazine

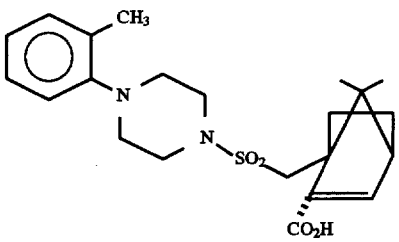

To a stirred solution of 1-((7,7-dimethyl-2-endo-methoxy-carbonyl-bicyclo(2.2.1)heptan-1-yl)methanesulfonyl)-4-(2-methylphenyl)piperazine (1.0 g; 2.3 mmol) in THF (10 mL) was added a solution of 4M aqueous NaOH (1.5 mL; 6.0 mmol). The reaction was heated to reflux for 72 h, cooled, and brought to pH 1 with 5% aqueous HCl. The solvents were removed under reduced pressure and the residue was partitioned between chloroform and water. The organic phase was separated and washed with water, dried (MgSO$_4$), filtered, and the solvent was removed under reduced pressure. The title compound was purified by preparative reverse phase HPLC using an acetonitrile-water gradient containing 0.1% TFA. The title compound was obtained as a lyophilized powder.

Anal: ($C_{22}H_{32}N_2O_4S$) calc. C, 51.92; H, 5.99; N, 4.94 found C, 51.92; H, 5.95; N, 5.17

1.25 TFA, 0.2 H$_2$O

TLC: R$_f$=0.22 (95:5:0.5 CHCl$_3$:MeOH:NH$_4$OH)

HPLC (method A): retention time 10.67 min

FAB MS: m/z 421 (M$^+$+H)

1H NMR (300 MHz, CD$_3$OD): d 7.18 (m, 2H), 7.05 (d, 1H), 6.98 (t, 1H), 2.30 (s, 3H), 1.18 (s, 3H), 1.10 (s, 3H)

EXAMPLE 61

1-((7,7-Dimethyl-2-endo-(4-imidazolyl)ethylamino-carbonyl-bicyclo-(2.2.1)heptan-1-yl)methanesulfonyl)-4-(2-methylphenyl)piperazine

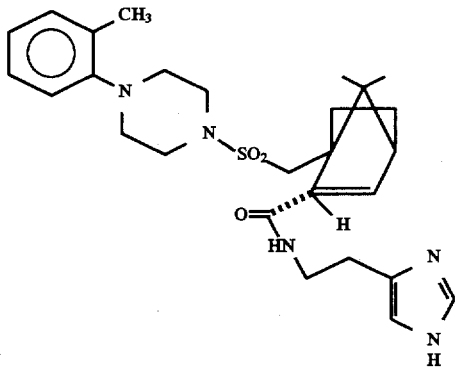

To a stirred solution of 1-((7,7-dimethyl-2-endo-carboxy-bicyclo(2.2.1)heptan-1-yl)methanesulfonyl)-4-(2-methylphenyl)piperazine (100 mg; 0.238 mmol) in DMF (5 mL) was histamine (35 mg; 0.32 mmol), BOP (142 mg; 0.321 mmol), and DIEA (0.13 mL; 0.75 mmol). After 18 h, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{27}H_{39}N_5O_3S$) calc. C, 46.66; H, 5.58; N, 8.58 found C, 46.63; H, 5.23; N, 8.97

2.35 TFA, 1.9 H$_2$O

HPLC (method A): retention time 8.99 min

FAB MS: m/z 514 (M$^+$+H)

1H NMR (300 MHz, CDCl$_3$): d 8.40 (s, 1H), 7.1–7.3 (m, 5H), 2.39 (s, 3H), 1.05 (s, 3H), 0.98 (s, 3H)

EXAMPLE 62

Two isomers of 1-((7,7-dimethyl-2-exo-hydroxy-2-endo-2-(1-(3-methoxycarbonyl)-2-pyrrolidinon-1-yl)propylbicyclo-(2.2.1)heptan-1-yl)methanesulfonyl)-4-(2-methylphenyl)piperazine

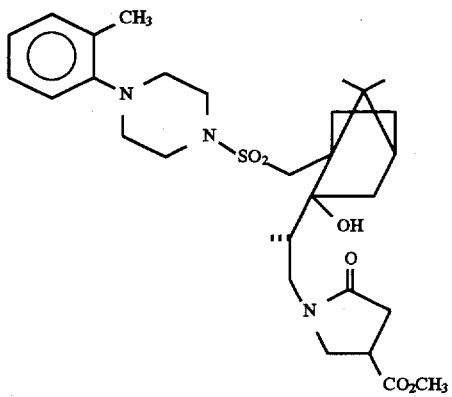

To a stirred solution of 1-((7,7-dimethyl-2-exo-hydroxy-2-endo-2-(1-amino)propyl-(2.2.1)bicyclo-heptan-1-yl)methanesulfonyl)-4-(2-methylphenyl)piperazine (250 mg; 0.557 mmol) in methanol (3 mL) was added dimethyl itaconate (200 mg; 1.27 mmol). The reaction was heated to reflux for 18 h. The solvent was removed under reduced pressure and the residue was purified by pressurized silica gel column chromatography using 35:65 hexane-ethyl acetate as eluant. The products were obtained as white foams.

Isomer 1:

Anal: ($C_{30}H_{45}N_3O_6S$) calc. C, 62.58; H, 7.88; N, 7.30 found C, 62.58; H, 8.03; N, 6.95

TLC: R$_f$0.34 (35:65 hexane-ethyl acetate)

HPLC (method A): retention time 10.23 min

FAB MS: m/z 576 (M$^+$+H)

$^1$H NMR (300 MHz, CDCl$_3$): d 7.18 (m, 2H), 7.01 (m, 2H), 3.76 (s, 3H), 2.32 (s, 3H), 1.15 (s, 3H), 1.03 (s, 3H), 0.95 (d, J=6 Hz, 3H)

Isomer 2:

Anal: ($C_{30}H_{45}N_3O_6S$) calc. C, 62.58; H, 7.88; N, 7.30 found C, 62.43; H, 8.07; N, 6.95

TLC: R$_f$0.23 (35:65 hexane-ethyl acetate)

HPLC (method A): retention time 10.24 min

FAB MS: m/z 576 (M$^+$+H)

$^1$H NMR (300 MHz, CDCl$_3$): d 7.20 (m, 2H), 7.03 (m, 2H), 3.74 (s, 3H), 2.32 (s, 3H), 1.15 (s, 3H), 1.03 (s, 3H), 0.95 (d, J=6 Hz, 3H)

EXAMPLE 63

1-((7,7-Dimethyl-2-exo-hydroxy-2-endo-2-(1-(4-pyridinyl)methylamino)-propyl-bicyclo(2.2.1)heptan-1-yl)methanesulfonyl)-4-(2-methylphenyl)-piperazine

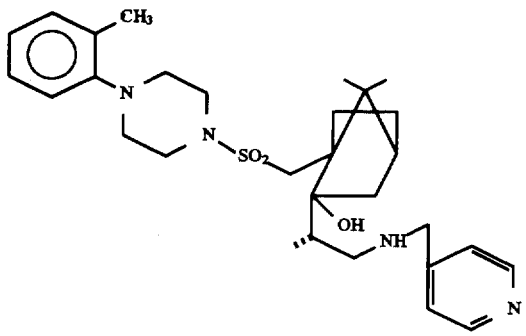

To a stirred solution of 1-((7,7-dimethyl-2-exo-hydroxy-2-endo-2-(1-amino)propyl-(2.2.1)bicycloheptan-1-yl)methanesulfonyl)-4-(2-methyl-phenyl)piperazine (50 mg; 0.11 mmol) in DMF (2 mL) was added 4-chloromethylpyridine hydrochloride (18 mg; 0.11 mmol) and potassium carbonate (50 mg; 0.36 mmol). The reaction was heated to 80° C. 18 h. The solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{30}H_{44}N_4O_3S$) calc. C, 52.07; H, 5.89; N, 7.06 found C, 52.06; H, 5.86; N, 7.20

2.2 TFA, 0.1 $H_2O$

TLC: $R_f$=0.36 (95:5:0.5 $CHCl_3$:MeOH:$NH_4OH$)

HPLC (method A): retention time 8.15 min

FAB MS: m/z 541 ($M^+$+H)

$^1$H NMR (300 MHz, $CDCl_3$): d 8.72 (br s, 2H), 7.85 (br s, 2H), 7.20 (m, 2H), 7.03 (m, 2H), 4.27 (AB quartet, 2H), 2.31 (s, 3H), 1.14 (s, 3H), 0.95 (overlapping s and d, 6H)

EXAMPLE 64

1-((7,7-Dimethyl-2-(3-acetamido-3,3'-di(ethoxycarbonyl))propylidine-bicyclo(2.2.1)heptan-1-yl)methanesulfonyl)-4-(2-methylphenyl)piperazine

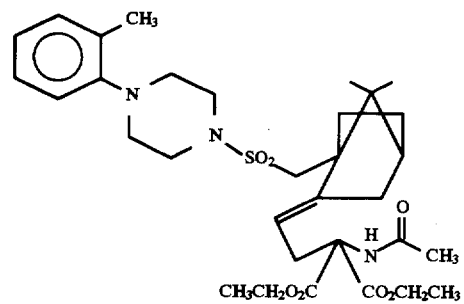

To a stirred solution of diethyl acetamidomalonate (0.69 g; 3.2 mmol) in DMF (20 mL) was added NaH (125 mg of a 60% dispersion in mineral oil; 3.13 mmol). After 30 min, 1-((7,7-dimethyl-2-(2-chloro)-ethylidine-(2.2.1)bicycloheptan-1-yl)methanesulfonyl)-4-(2-methylphenyl)-piperazine (0.35 g; 0.80 mmol) was added and the mixture was warmed to 50° C. for 3 h. The mixture was cooled and acetic acid (1.5 mL) was added. The solvents were removed under reduced pressure, the residue was dissolved in ethyl acetate (75 mL) and washed with water (3×25 mL). The organic phase was dried, filtered, and the solvent was removed under reduced pressure. The residue was purified by pressurized silica gel column chromatography using 2:1 hexane-ethyl acetate as eluant. The title compound was obtained as a white foam.

Anal: ($C_{32}H_{47}N_3O_7S$) calc. C, 62.32; H, 7.51; N, 6.81 found C, 61.96; H, 7.71; N, 6.55

TLC: $R_f$=0.36 (95:5:0.5 $CHCl_3$:MeOH:$NH_4OH$)

HPLC (method A): retention time 11.54 min

FAB MS: m/z 618 ($M^+$+H)

$^1$H NMR (400 MHz, $CDCl_3$): d 7.20 (m, 2H), 7.03 (m, 2H), 6.78 (s, 1H), 5.38 (br t, 1H), 4.22 (m, 4H), 2.32 (s, 3H), 2.00 (s, 3H), 1.27 (t, J=7 Hz, 3H), 1.24 (t, J=7 Hz, 3H), 0.97 (s, 3H), 0.78 (s, 3H)

EXAMPLE 65

1-((7,7-Dimethyl-2-(3-acetamido-3-carboxy)propylidine-bicyclo(2.2.1)heptan-1-1 methanesulfonyl)-4-2-methylphenyl)piperazine

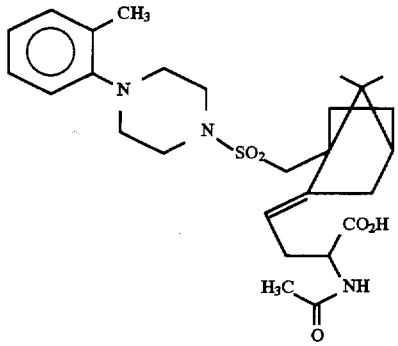

To a stirred solution of 1-((7,7-dimethyl-2-(3-acetamido-3,3'-di(ethoxycarbonyl))propylidine-(2.2.1)bicycloheptan-1-yl)methanesulfonyl)-4-(2-methylphenyl)-piperazine (0.10 g; 0.16 mmol) in ethanol (2 mL) was added a solution of 2M NaOH (0.30 mL; 0.60 mmol) and the mixture was heated to reflux for 6 h. The mixture was cooled and brought to pH 2 with 5% aqueous HCl. The mixture was heated to reflux for 1 h. The solvents were removed under reduced pressure and the residue was purified by preparative reverse phase HPLC using an acetonitrile-water gradient containing 0.1% TFA. The title compound, as a 1:1 mixture of diastereomers, was obtained as a lyophilized powder.

Anal: ($C_{27}H_{39}N_3O_5S$) calc. C, 54.37; H, 6.53; N, 6.56 found C. 54.26; H, 6.41; N, 6.59

1.0 TFA, 0.5 $H_2O$

TLC: $R_f$=0.39 (92:8:0.1 $CHCl_3$:MeOH:HOAc)

HPLC (method A): retention time 9.62 min

FAB MS: m/z 518 ($M^+$+H)

$^1$H NMR (400 MHz, $CDCl_3$): d 7.25 (m, 4H), 7.13 (m, 4H), 6.52 (d, 1H), 6.40 (d, 1H), 5.45 (m, 1H), 5.40 (m, 1H), 4.67 (m, 2H), 2.40 (s, 6H), 20.5 (s, 3H), 2.04 (s, 3H), 1.01 (s, 3H), 0.98 (s, 3H), 0.88 (s, 3H), 0.79 (s, 3H)

EXAMPLE 66

1-((7,7-Dimethyl-2-oxo-bicyclo(2.2.1)heptan-1-yl)methanesulfonyl)-4-(2-methylphenyl)-3-piperazinone

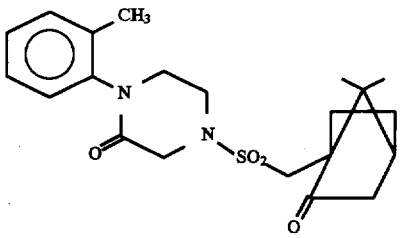

To a stirred solution of 1-t-butyloxycarbonyl-4-(2-methylphenyl)-3-piperazinone (0.25 g; 0.86 mmol) in dichloromethane (3 mL) was added TFA (1 mL). After 1 hour the solvents were removed under reduced pressure and the residue was taken up into chloroform and evaporated several times to remove excess TFA. The residue was dissolved in chloroform (5 mL) and added to the stirred solution was 10-camphorsulfonyl chloride (376 mg; 1.50 mmol) and triethylamine (0.38 mL; 2.7 mmol). After 12 hours, the mixture was diluted with chloroform (25 mL) and extracted with 5% aqueous HCl (25 mL), water (25 mL), and aqueous NaHCO$_3$ (25 mL). The organic phase was dried (MgSO$_4$), filtered, and the solvent was removed under reduced pressure. The residue was purified by pressurized silica gel column chromatography using 2:1 hexane-ethyl acetate as eluant. The title compound was obtained as a white foam from ether-hexane.

Anal: (C$_{21}$H$_{28}$N$_2$O$_4$S) Calc. C, 62.35; H, 6.98; N, 6.93 Found C, 61.78; H, 6.98; N, 6.82

TLC: R$_f$0.30 (1:1 hexane-ethyl acetate)

HPLC (method A): retention time 8.15 min

FAB MS: m/z 405 (M$^+$+H)

EXAMPLE 67

1-((7,7-Dimethyl-2-oxo-bicyclo(2.2.1)heptan-1-yl)-methanesulfonyl)-4-(2-methylphenyl)-2-methyl-3-piperazinone

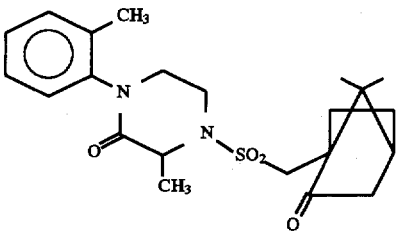

To a stirred 78° C. solution of LDA (2.0 mmol) in THF (15 mL) was added a −78° C. solution of 1-t-butyloxycarbonyl-4-(2-methylphenyl)-3-piperazinone (0.50 g; 1.7 mmol) in THF (5 mL). The resulting solution was stirred for 1 hour, when iodomethane (0.125 mL; 2.0 mmol) was added. The reaction mixture was stirred at −78° C. for 30 minutes, and then the cooling bath was removed and the mixture was stirred at ambient temperature for 3 hours. Water (10 mL) and ethyl acetate (50 mL) were added. The organic layer was separated and washed with water (25 mL) and brine (25 mL). The organic phase was dried (MgSO$_4$), filtered, and the solvent was removed under reduced pressure. The residue was purified by pressurized silica gel column chromatography using 85:15 hexane-ethyl acetate as eluant. The methylated product had an Rf=0.47 (70:30 hexane-ethyl acetate) and an HPLC retention time of 8.32 min (Method A). The product (0.40 g; 1.3 mmol) was dissolved in chloroform (3 mL) and TFA (1 mL) was added. After 2 hours, the mixture was diluted with chloroform (50 mL) and extracted with aqueous NaHCO$_3$ (3×25 mL). The organic phase was dried (MgSO$_4$), filtered, and the solvent was removed under reduced pressure to give an oil (HPLC retention time 2.95 min, Method A). The residue was dissolved in chloroform (20 mL) and to the stirred solution was added 10-camphorsulfonyl chloride (0.41 g; 1.6 mmol) and triethylamine (0.28 mL; 2.0 mmol). After 12 hours, the mixture was diluted with chloroform (25 mL) and extracted with 5% aqueous HCl (25 mL), water (25 mL), and aqueous NaHCO$_3$ (2×25 mL). The organic phase was dried (MgSO$_4$), filtered, and the solvent was removed under reduced pressure. The residue was purified by pressurized silica gel column chromatography using 2:1 hexane-ethyl acetate as eluant. The title compound, as a 1:1 mixture of diastereomers, was obtained as a white solid from hexane-ether.

Anal: (C$_{22}$H$_{30}$N$_2$O$_4$S) Calc. C, 63.13; H, 7.23; N, 6.69 Found C, 63.46; H, 7.09; N, 6.74

TLC: R$_f$0.27 (60:40 hexane-ethyl acetate)

HPLC (method A): retention time 8.52 min

FAB MS: m/z 419 (M$^+$+H)

$^1$H NMR (300 MHz, CDCl$_3$): d 7.1–7.3 (m, 8H), 4.62 (overlapping quartets, 2H), 2.21 (s, 3H), 2.20 (s, 3H), 1.68 (overlapping doublets, 6H), 1.13 (s, 3H), 1.11 (s, 3H), 0.91 (s, 3H), 0.89 (s, 3H)

EXAMPLE 68

1-((7,7-Dimethyl-2-exo-hydroxy-bicyclo(2.2.1)heptan-1-yl)methanesulfonyl)-4-(2-methylphenyl)-2-methyl-piperazine

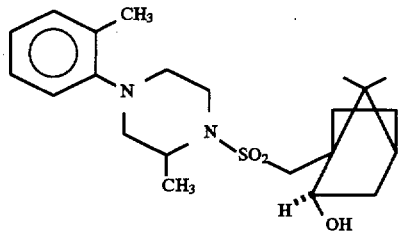

To a stirred, 0° C. solution of 1-((7,7-dimethyl-2-oxo-bicyclo(2.2.1)heptan-1-yl)methanesulfonyl)-4-(2-methylphenyl)-2-methyl-3-piperazinone (0.15 g; 0.36 mmol) in THF (5 mL) was added a 1.0M solution of LAH in THF (1.1 mL; 1.1 mmol). The resulting solution was warmed to ambient temperature and stirred for 3 hours. The reaction was quenched by adding aqueous NaOH to give a white precipitate. The mixture was diluted with ethyl acetate and the solids were removed by filtration through Celite. The filtrate solvents were removed under reduced pressure and the residue was purified by pressurized silica gel column chromatography using 9:1 hexane-ethyl acetate as eluant to give 1-((7,7-dimethyl-2-exo-hydroxy-bicyclo(2.2.1)heptan-1-yl)methanesulfonyl)-4-(2-methylphenyl)-2-methyl-2,3-dehydro-piperazine (FAB MS: m/z 405 (M$^+$+H); olefinic proton at 5.8 ppm in the ¹H NMR spectrum). This product (75 mg; 0.19 mmol) was dissolved in triethylsilane (2 mL) and to the stirred solution was added TFA (0.030 mL; 0.38 mmol). After 18 hours, the solvents were removed under reduced pressure and the residue was dissolved in ethyl acetate (20 mL) and washed with aqueous NaHCO₃ (2×10 mL). The organic phase was dried (MgSO₄), filtered, and the solvent was removed under reduced pressure. The residue was purified by preparative reverse phase HPLC using an acetonitrile-water gradient containing 0.1% TFA. The title compound, as a 1:1 mixture of diastereomers, was obtained as a lyophilized powder.

HPLC (method A): retention time 14.33 min

FAB MS: m/z 407 (M⁺+H)

¹H NMR (400 MHz, CDCl₃): d 7.20 (m, 4H), 7.06 (m, 4H), 4.20 (m, 2H), 2.36 (s, 6H), 1.55 (overlapping doublets, 6H), 1.09 (s, 6H), 0.86 (s, 6H)

EXAMPLE 69

1-((7,7-Dimethyl-2-oximino-bicyclo(2.2.1)heptan-1-yl)methanesulfonyl)-4-(2-methylphenyl)-piperazine

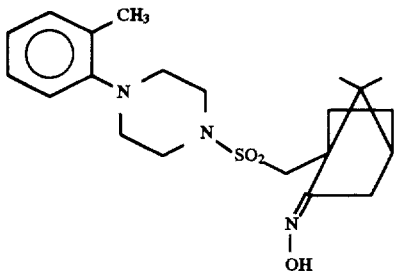

To a stirred solution of 1-((7,7-dimethyl-2-oxo-bicyclo(2.2.1)-heptan-1-yl)methanesulfonyl)-4-(2-methylphenyl)piperazine (65.0 g; 166 mmol) in pyridine (250 mL) was added hydroxylamine hydrochloride (35.0 g; 0.504 mol). The solution was heated to 70° C. for 18 h. The solvent was removed under reduced pressure, the residue was taken up in chloroform (500 mL) and washed with aqueous NaHCO3 (2×200 mL), water (100 mL), and 5% aqueous HCl (2×200 mL). The organic phase was dried (MgSO₄), filtered, and the solvent was removed under reduced pressure. The title compound crystallized from ethyl acetate, giving off-white needles (57 g; 84%), mp 174°–175° C.

Anal: (C₂₁H₃₁N₃O₃S) Calc. C, 62.19; H, 7.71; N, 10.36 Found C, 62.29; H, 7.63; N, 10.15

TLC: R/0.40 (75:25 hexane-ethyl acetate)

HPLC (method A): retention time 9.98 min

FAB MS: m/z 406 (M⁺+H)

¹H NMR (300 MHz, CDCl₃): d 7.90 (br s, 1H), 7.18 (m, 2H), 7.02 (m, 2H), 3.47 (m, 4H), 4.43 (d, J=14.4 Hz, 1H), 3.00 (m, 4H), 2.92 (d, J=14.4 Hz, 1H), 2.4–2.6 (m, 2H), 2.31 (s, 3H), 2.09 (d, J=16.9 Hz, 1H), 1.95 (m, 2H), 1.80 (m, 1H), 1.32 (m, 1H), 1.08 (s, 3H), 0.87 (s, 3H)

EXAMPLE 70

1-((7,7-Dimethyl-2-endo-amino-bicyclo(2.2.1)heptan-1-yl)methanesulfonyl)-4-(2-methylphenyl)-piperazine

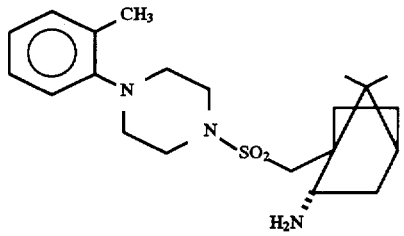

To a stirred solution of 1-((7,7-dimethyl-2-oximino-bicyclo(2.2.1)heptan-1-yl)methanesulfonyl)-4-(2-methylphenyl)piperazine (35.0 g; 86 mmol) in 2-methoxyethanol (500 mL) containing Raney Nickel alloy (105.0 g) was added sodium hydroxide solution (17.2 g; 430 mmol dissolved in 75 mL) dropwise over 30 min. During the addition heat and gas was evolved. The mixture was stirred at ambient temperature for 16 h, at which time TLC indicated complete consumption of starting oxime and a ca. 4:1 mixture of endo (lower Rf) and exo (higher Rf) amine products. The mixture was filtered through Celite and the filtercake was washed with methanol and ethyl acetate. The solvents were removed under reduced pressure and the resulting solid was dispersed in water and filtered. The dried solid was purified by pressurized silica gel column chromatography, using a 93:3 to 94:6 A:B gradient elution (A=chloroform, B=5% NH₄OH/MeOH). The title compound was obtained as a white foam (24 g; 70%).

FAB MS: m/z 392 (M⁺+H)

EXAMPLE 71

1-((7,7-Dimethyl-2-endo-(2S-(tert-butyloxycarbonyl-amino)-4-(methylsulfonyl)-butyramido)-bicyclo(2.2.1)-heptan-1-yl)methanesulfonyl)-4-(2-methylphenyl)-piperazine

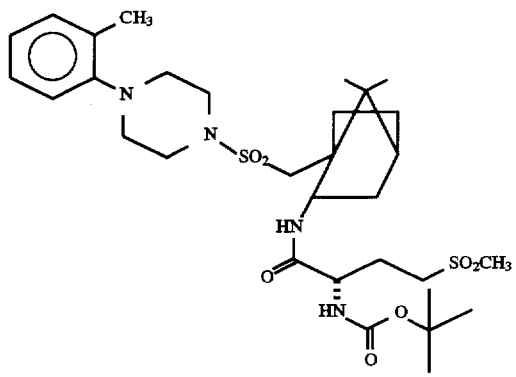

To a stirred solution of 1-((7,7-dimethyl-2-endo-amino-bicyclo(2.2.1)heptan-1-yl)methanesulfonyl)-4-(2-methylphenyl)piperazine (2.0 g; 5.1 mmol) in DMF (20 mL) was added Boc-L-methionine sulfone (1.5 g; 5.3 mmol), BOP reagent (2.5 g; 5.6 mmol), followed by DIEA (1.85 mL; 10.6 mmol). After being stirred at ambinet temperature for 1 h, more DIEA (ca. 0.1 mL) was added to obtain a pH 8 solution. The solution was stirred for another 1 h, when the solvent was removed under reduced pressure. The residue was dissolved in EtOAc (150 mL) and washed with 5% aqueous HCL (2×50 mL), water (2×50 mL), and aqueous NaHCO$_3$ (2×75 mL). The organic phase was dried (MgSO$_4$), filtered, and the solvent was removed under reduced pressure. The residue was purified by pressurized silica gel column chromatography, using 4:1 EtOAc-hexanes as eluant. The title compound was obtained as a solid from methanol (2.8 g; 85%).

Anal: (C$_{31}$H$_{50}$N$_4$O$_7$S$_2$) Calc. C, 55.78; H, 7.76; N, 8.39 0.7.H$_2$O Found C, 55.57; H, 7.70; N, 8.36

TLC: R$_f$0.73 (95:5 CHCl$_3$:MeOH)

HPLC (method A): retention time 11.02 min

FAB MS: m/z 655 (M$^+$+H)

$^1$H NMR (300 MHz, CDCl$_3$): d 7.19 (m, 2H), 7.04 (m, 2H), 5.38 (br d, 1H), 4.32 (q, J=7.4 Hz, 1H), 4.22 (m, 1H), 2.94 (s, 3H), 2.32 (s, 3H), 1.45 (s, 9H), 1.00 (s, 3H), 0.98 (s, 3H)

EXAMPLE 72

1-((7,7-Dimethyl-2-endo-(2S-amino-4-(methylsulfonyl)-butyramido)bicyclo(2.2.1)heptan-1-yl)methanesulfonyl)-4-(2-methylphenyl)piperazine

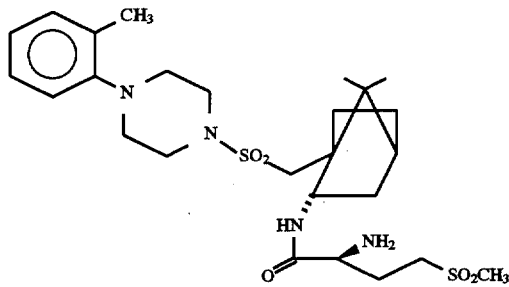

To a stirred solution of 1-((7,7-dimethyl-2-endo-(2S-tert-butyloxycarbonylamino-4-(methylsulfonyl)-butyramido)-bicyclo(2.2.1)heptan-1-yl)methane sulfonyl)-4-(2-methylphenyl)piperazine (2.5 g; 3.8 mmol) in dichloromethane (15 mL) was added TFA (5 mL). After 1 h, the solvents were removed under reduced pressure. The residue was dissolved in chloroform (100 mL) and washed with aqueous NaHCO$_3$ (2×75 mL). The organic phase was dried (MgSO$_4$), filtered, and the solvent was removed under reduced pressure. The residue was purified by pressurized silica gel column chromatography using 95:5:0.5 CHCl$_3$:MeOH:NH$_4$OH as eluant. The title was obtained as a white foam from EtOAc (1.9 g; 90%).

Anal: (C$_{26}$H$_{42}$N$_4$O$_5$S$_2$) Calc. C, 56.14; H, 7.75; N, 9.29 0.55 EtOAc Found C, 55.94; H, 7.74; N, 9.31

TLC: R$_f$0.17 (95:5:0.5 CHCl$_3$:MeOH:NH$_4$OH)

HPLC (method A): retention time 8.50 min

FAB MS: m/z 455 (M$^+$+H)

$^1$H NMR (300 MHz, CDCl$_3$): d 7.67 (d, J=8.4 Hz, 1H), 7.20 (m, 2H), 7.02 (m,2H), 4.43 (m, 1H), 2.94 (s, 3H), 2.31 (s, 3H), 1.03 (s, 3H), 0.97 (s, 3H)

EXAMPLE 73

1-((7,7-Dimethyl-2-endo-(2S-(imidazol-4-ylacetyl-amino)-4-(methylsulfonyl)butyramido)-bicyclo(2.2.1)-heptan-1-yl)methanesulfonyl)-4-(2-methylphenyl)-piperazine

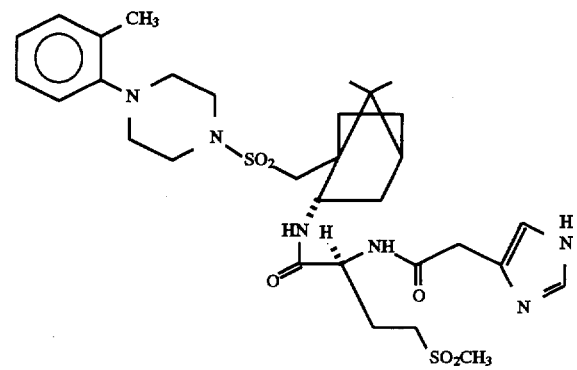

To a stirred solution of 1-((7,7-dimethyl-2-endo-(2S-amino-4-(methylsulfonyl)butyramido)-bicyclo(2.2.1) heptan-1-yl)methanesulfonyl)-4-(2-methylphenyl) piperazine (250 mg; 0.45 mmol) in DMF (5 mL) was added 4-imidazole acetic acid hydrochloride (110 mg; 0.68 mmol), BOP (265 mg; 0.60 mmol), and DIEA (0.355 mL; 2.0 mmol). The solution was stirred at ambient temperature for 18 h. The solvent was removed under reduced pressure, and the residue was suspended in EtOAc (100 mL) and filtered through Celite to remove red polymer. The filtrate was washed with 5% aqueous HCl (50 mL), water (50 mL), and aqueous NaHCO$_3$ (2×50 mL). The organic phase was dried (MgSO$_4$), filtered, and the solvent was removed under reduced pressure. The residue was purified by pressurized silica gel column chromatography using 92:8:0.8 CHCl$_3$:MeOH:NH$_4$OH as eluant. The title compound was obtained as a solid from EtOAc (230 mg; 78%).

Anal: (C$_{31}$H$_{46}$N$_6$O$_6$S$_2$) Calc. C, 53.74; H, 7.32; N, 11.26 0.6 EtOAc, 1.7H$_2$O Found C, 53.74; H, 7.00; N, 11.25

TLC: R$_f$0.22 (90:10:0.5 CHCl$_3$:MeOH:NH$_4$OH)

HPLC (method A): retention time 8.49 min

FAB MS: m/z 663 (M$^+$+H)

$^1$H NMR (300 MHz, CDCl$_3$): d 7.73 (overlapping singlet and broad singlet, 2H), 7.38 (br d, 1H), 7.18 (m, 2H), 7.02 (m, 2H), 6.96 (s, 1H), 4.68 (br q, J=ca. 5 Hz, 1H), 4.27 (m, 1H), 3.62 (br s, 2H), 2.92 (s, 3H), 2.30 (s, 3H), 1.00 (s, 3H), 0.98 (s, 3H)

EXAMPLE 74

1-((7,7-Dimethyl-2-endo-(2S-(dimethylamino)-4-(methylsulfonyl)butyramido)-bicyclo(2.2.1)heptan-1-yl)methanesulfonyl)-4-(2-methylphenyl)piperazine

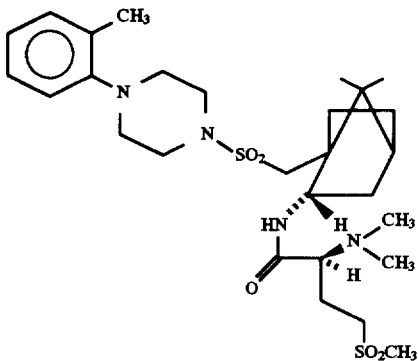

To a stirred solution of 1-((7,7-dimethyl-2-endo-(2S-amino-4-(methylsulfonyl)butyramido)-bicyclo-(2.2.1)-heptan-1-yl)methanesulfonyl)-4-(2-methylphenyl)-piperazine (250 mg; 0.45 mmol) in 1:1 HOAc:MeOH (10 mL) was added 37% aqueous formaldehyde (2 mL) and NaBH$_3$CN (60 mg; 0.95 mmol). The solution was stirred at ambient temperature for 4 h. Aqueous NaHCO$_3$ (2 mL) was added and the solvents were removed under reduced pressure. The residue was suspended in EtOAc (75 mL) and washed with water (2×50 mL). The organic phase was dried (MgSO$_4$), filtered, and the solvent was removed under reduced pressure. The title compound was obtained as a white foam from EtOAc (190 mg; 72%).

Anal: (C$_{28}$H$_{46}$N$_4$O$_5$S$_2$) Calc. C, 57.56; H, 8.01; N, 9.20 0.3 EtOAc. Found C, 57.41; H, 7.98; N, 9.20

TLC: R$_f$0.26 (95:5:0.5 CHCl$_3$:MeOH:NH$_4$OH)

HPLC (method A): retention time 9.10 min

FAB MS: m/z 583 (M$^+$+H)

$^1$H NMR (400 MHz, CDCl$_3$): d 7.62 (Br s, 1H), 7.18 (m, 2H), 7.02 (M, 2H), 4.37 (m, 1H), 2.92 (s, 3H), 2.36 (s, 6H), 2.30 (s, 3H), 1.02 (s, 3H), 0.98 (s, 3H)

EXAMPLE 75

1-((7,7-Dimethyl-2-endo-benzyloxycarbonylamino-bicyclo(2.2.1)heptan-1-yl)methanesulfonyl)-4-(2-methyl-phenyl)-piperazine

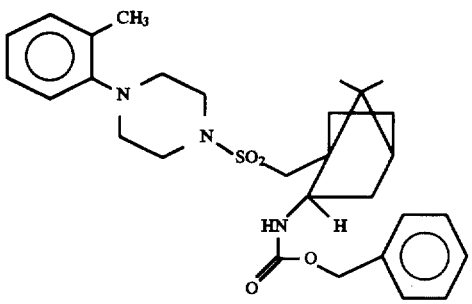

To a 0° C. stirred solution of 1-((7,7-dimethyl-2-endo-amino-bicyclo(2.2.1)heptan-1-yl)methanesulfonyl)-4-(2-methylphenyl)piperazine (1.20 g; 3.07 mmol) in CHCl$_3$ (100 mL) was added DIEA (0.80 mL; 4.6 mmol) and benzyl chloroformate (0.58 g; 3.4 mmol). The solution was stirred at 0° C. for 1 h and then at ambient temperature for 4 h. The reaction mixture was washed with 5% aqueous HCl (2×50 mL) and aqueous NaHCO$_3$ (100 mL). The organic phase was dried (MgSO$_4$), filtered, and the solvent was removed under reduced pressure. The residue was purified by pressurized silica gel column chromatography using 1:4 EtOAc-hexanes as eluant. The title compound was obtained as a white foam. (1.45 g; 90%).

Anal: (C$_{29}$H$_{39}$N$_3$O$_4$S) Calc. C, 65.75; H, 7.53; N, 7.77 0.15 EtOAc, 0.1 H$_2$O Found C, 65.90; H, 7.49; N, 7.80

TLC: R$_f$0.38 (1:3 EtOAc:hexanes)

HPLC (method A): retention time 12.18 min

FAB MS: m/z 526 (M$^+$+H)

EXAMPLE 76

1-((7,7-Dimethyl-2-endo-methyl(benzyloxycarbonyl)amino-bicyclo(2.2.1)-heptan-1-yl)methanesulfonyl)4-(2-methylphenyl)piperazine

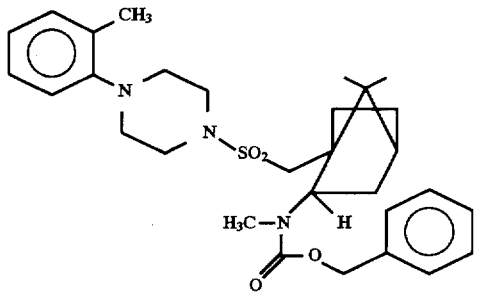

To a 0° C. stirred solution of 1-((7,7-dimethyl-2-endo-benzyloxycarbonylamino-bicyclo(2.2.1)-heptan-1-yl)methanesulfonyl)-4-(2-methylphenyl)-piperazine (1.46 g; 2.78 mmol) in DMF (20 mL) was added iodomethane (0.435 mL; 7.00 mmol) and sodium hydride (0.139 mg of a 60% dispersion in mineral oil; 3.48 mmol). The solution was stirred at 0° C. for 1 h and then at ambient temperature for 18 h. The reaction mixture was treated with HOAc (1 mL) and the solvents were removed under reduced pressure. The residue was dissolved in EtOAc (100 mL) and washed with aqueous NaHCO$_3$ (2×50 mL). The organic phase was dried (MgSO$_4$), filtered, and the solvent was removed under reduced pressure. The residue was purified by pressurized silica gel column chromatography using 1:5 EtOAc-hexanes as eluant. The title compound was obtained as a white foam. (1.40 g; 93%).

Anal: (C$_{30}$H$_{41}$N$_3$O$_4$S) Calc. C, 66.03; H, 7.70; N, 7.70 0.33 H$_2$O Found C, 66.03; H, 7.63; N, 7.68

TLC: R$_f$0.44 (1:4 EtOAc:hexanes)

HPLC (method A): retention time 12.86 min

FAB MS: m/z 540 (M$^+$+H)

$^1$H NMR (300 MHz, CDCl$_3$): d 7.25–7.45 (m, 5H), 7.20 (m, 2H), 7.02 (m, 2H), 5.11 (AB quartet, 2H), 4.83 (m, 1H), 3.03 (s, 3H), 2.32 (s, 3H), 1.04 (s, 3H), 0.96 (s, 3H)

EXAMPLE 77

1-((7,7-dimethyl-2-endo-methyl(2S-amino-4-(methylsulfonyl)butanoyl)amino-bicyclo(2.2.1)heptan-1-yl)methanesulfonyl)-4-(2-methylphenyl)-piperazine To a stirred, argon purged solution of 1-((7,7-dimethyl-2-endo-methyl(benzyloxycarbonyl)amino-bicyclo(2.2.1)

heptan-1-yl)methane-sulfonyl)-4-(2-methylphenyl) piperazine (1.1 g; 2.0 mmol) in 96:4 MeOH-HCO$_2$H (25 mL) was added palladium black (0.4 g). The reaction mixture was stirred for 16 h at ambient temperature. The catalyst was removed by filtration through Celite, and the filtrate solvents were removed under reduced pressure. The residue was purified by pressurized silica gel column chromatography using 95:5:0.5 CHCl$_3$:MeOH:NH$_4$OH as eluant. The product, 1-((7,7-dimethyl-2-endo-methyl-amino-bicyclo(2.2.1)heptan-1-yl)methanesulfonyl)-4-(2-methylphenyl)piperazine, was obtained as a white foam. (0.79 g; 95%). To a stirred solution of 1-((7,7-dimethyl-2-endo-methylamino-bicyclo(2.2.1)-heptan-1-yl) methanesulfonyl)-4-(2-methylphenyl)-piperazine (0.700 g; 1.73 mmol) in CHCl$_3$ (60 mL) was added the acid fluoride of Na-Fmoc-L-methionine sulfone (1.23 g; 3.03 mmol) and DIEA (0.52 mL; 3.0 mmol). The mixture was stirred at ambient temperature for 24 h, and then extracted with 5% aqueous HCl (30 mL), water (30 mL), and aqueous NaHCO$_3$ (2×30 mL). The organic phase was dried (MgSO$_4$), filtered, and the solvent was removed under reduced pressure. The residue was dissolved in DMF (10 mL), and to the solution was added diethylamine (2 mL). The mixture was stirred at ambient temperature for 6 h. The solvents were removed under reduced pressure and the residue was purified by pressurized silica gel column chromatography using 95:5:0.5 CHCl$_3$:MeOH:NH$_4$OH as eluant. The title compound was obtained as a foam from CHCl$_3$-ether (0.71 g; 61%).

Anal: (C$_{27}$H$_{44}$N$_4$O$_5$S$_2$) Calc. C, 56.26; H, 7.80; N, 9.40 0.1 CHCl$_3$, 0.2 ether Found C, 56.21; H, 7.79; N, 9.22

TLC: R$_f$0.10 (95:5:0.5 CHCl$_3$:MeOH:NH$_4$OH)

HPLC (method A): retention time 9.01 min

FAB MS: m/z 569 (M$^+$+H)

$^1$H NMR (300 MHz, CDCl$_3$): d 7.18 (m, 2H), 7.03 (m, 2H), 5.20 (ddd, 1H), 3.95 (dd, J=, 9.3, 4.1 Hz, 1H), 3.18 (s, 3H), 2.91 (s, 3H), 2.30 (s, 3H), 1.06 (s, 3H), 0.96 (s, 3H)

EXAMPLE 78

1-((7,7-Dimethyl-2-endo-methyl(2S-dimethylamino-4-(methylsulfonyl)butanoyl)amino-bicyclo(2.2.1) heptan-1-yl)methanesulfonyl)-4-(2-methylphenyl)-piperazine To a stirred solution of 1-((7,7-dimethyl-2-endo-methyl (2S-amino-4-(methylsulfonyl)butanoyl)amino-bicyclo (2.2.1)heptan-1-yl)methanesulfonyl)-4-(2-methylphenyl) piperazine (150 mg; 0.264 mmol) in 1:1 HOAc:MeOH (6 mL) was added 37% aqueous formaldehyde (1 mL) and NaBH$_3$CN (30 mg; 0.47 mmol). The solution was stirred at ambient temperature for 4 h. Aqueous NaHCO$_3$ (1 mL) was added and the solvents were removed under reduced pressure. The residue was suspended in EtOAc (50 mL) and washed with water (2×25 mL). The organic phase was dried (MgSO$_4$), filtered, and the solvent was removed under reduced pressure. The residue was purified by preparative reverse phase HPLC using a water-acetonitrile gradient containing 0.1% TFA. The TFA salt of the title compound was obtained as a lyophilized powder.

Anal: (C$_{29}$H$_{48}$N$_4$O$_5$S$_2$) Calc. C, 44.88; H, 5.94; N, 6.16 2.5 TFA, 1.5 H$_2$O Found C, 44.80; H, 5.94; N, 6.18

TLC: R$_f$0.45 (95:5:0.5 CHCl$_3$:MeOH:NH$_4$OH)

HPLC (method A): retention time 9.04 min

FAB MS: m/z 597 (M$^+$+H)

$^1$H NMR (400 MHz, CDCl$_3$): d 7.2–7.3 (m, 4H), 5.15 (m, 1H), 4.79 (br t, 1H), 3.21 (s, 3H), 2.98 (s, 3H), 2.95 (s, 6H), 2.43 (s, 3H), 1.07 (s, 3H), 0.97 (s, 3H)

EXAMPLE 79

1-((7,7-Dimethyl-2-endo-(4-imidazolyl)acetyl) amino-bicyclo(2.2.1)heptan-1-yl)methanesulfonyl)-4-(2-methyl-phenyl)piperazine To a stirred solution of 1-((7,7-dimethyl-2-endo-amino-bicyclo(2.2.1)heptan-1-yl)methanesulfonyl)-4-(2-methylphenyl)piperazine (1.50 g; 3.84 mmol) in DMF (30 mL) was added 4-imidazole acetic acid hydrochloride (0.938 g; 5.76 mmol), BOP (2.13 g; 4.80 mmol), and DIEA (2.61 mL; 15.0 mmol). The reaction mixture was stirred for 24 h at ambient temperature, and the solvent was removed under reduced pressure. The residue was suspended in EtOAc (100 mL) and filtered through Celite to remove red polymer. The filtrate was washed with aqueous NaHCO$_3$ (2×50 mL) and water (2×50 mL). The organic phase was dried (MgSO$_4$), filtered, and the solvent was removed under reduced pressure. The residue was purified by pressurized silica gel column chromatography using 92:8:0.8 CHCl$_3$:MeOH:NH$_4$OH as eluant. The title compound was obtained as white foam.

FAB MS: m/z 500 (M$^+$+H)

1H NMR (CDCl$_3$):

EXAMPLE 80

1-((7,7-Dimethyl-2-endo-(2-(4-imidazolyl) propanoyl)-amino -bicyclo(2.2.1)heptan-1-yl) methanesulfonyl)-4-(2-methylphenyl)piperazine To a stirred solution of 1-((7,7-dimethyl-2-endo-amino-bicyclo(2.2.1)heptan-1-yl)methanesulfonyl)-4-(2-methylphenyl)piperazine (1.1 g; 2.8 mmol) in DMF (25 mL) was added 2-(1-benzyloxymethyl-5-imidazolyl)propionic acid hydrochloride (0.920 g; 3.10 mmol), BOP (1.35 g; 3.05 mmol), and DIEA (1.50 mL; 8.61 mmol). The reaction mixture was stirred for 1 h at ambient temperature, and more DIEA (ca. 0.2 mL) was added to bring the mixture to pH 8. After another 1 h, the solvent was removed under reduced pressure. The residue was dissolved in CHCl$_3$ (150 mL) and washed with aqueous NaHCO$_3$ (2×50 mL) and water (2×50 mL). The organic phase was dried (MgSO$_4$), filtered, and the solvent was removed under reduced pressure to give a solid. Recrystallization from EtOAc gave crystals (0.51 g) which, by $^1$H NMR analysis, proved to be a 90:10 mixture of isomers (product A). The filtrate was purified by pressurized silica gel column chromatography using 95:5 CHCl$_3$:MeOH as eluant, giving a white foam (1.0 g). $^1$H NMR indicated this material to be a 1:2 mixture of isomers (product B). Products A and B were individually deblocked by hydrogenation for 24 h at ambient temperature in 3:1 MeOH:HOAc using 25 weight % palladium black under 1 atmosphere of hydrogen. The catalyst was removed by filtration through Celite and the solvents were removed under reduced pressure. Catalyst was removed by filtration through Celite, and the filtrate solvents were removed under reduced pressure. The residue derived from product A was purified by preparative reverse phase HPLC using a water-acetonitrile gradient containing 0.1% TFA. The TFA salt of the title compound (90:10 mixture by $^1$H NMR) was obtained as a lyophilized powder. Product B was purified by pressurized silica gel column chromatography using 95:5:0.5 CHCl$_3$:MeOH:NH$_4$OH as eluant. The title compound was obtained as white foam from CHCl$_3$-ether (1:2 mixture by $^1$H NMR). The two isomers had identical chromatographic behavior.

Anal: (C$_{27}$H$_{37}$N$_5$O$_3$S) Calc. C, 60.36; H, 7.49; N, 12.46 0.25 CHCl$_3$, 0.25 ether Found C, 60.49; H, 7.26; N, 12.48

TLC: R/0.30 (93:7:0.7 CHCl₃:MeOH:NH₄OH)

HPLC (method A): retention time 8.79 min

FAB MS: m/z 514 (M⁺+H)

¹H NMR (400 MHz, CDCl₃): d 7.75 (br s, 1H), 7.20 (m, 2H), 7.0 (m, 3H), 4.40 (m, 1H), 2.30, 2.29 (two singlets, ca. 2:1 ratio, 3H), 1.57, 1.53 (two doublets, J=7 Hz, ca. 2:1 ratio, 3H), 1.00 (s, 3H), 0.96 (s, 3H)

Anal: (C₂₇H₃₇N₅O₃S) Calc. C, 48.91; H, 5.36; N, 9.03 2.3 TFA Found C, 48.99; H, 5.21; N, 9.03

TLC: Rf0.30 (93:7:0.7 CHCl₃:MeOH:NH₄OH)

HPLC (method A): retention time 8.79 min

FAB MS: m/z 514 (M⁺+H)

¹H NMR (400 MHz, CDCl₃): d 8.43 (s, 1H), 7.70 (d, 1H), 7.25 (m, 2H), 7.20 (s, 1H), 7.15 (m, 2H), 4.40 (m, 1H), 4.03 (q, J=7 Hhz, 1H), 2.38 (s, 3H), 1.57 (d, J=7 Hz, 3H), 1.00 (s, 3H), 0.95 (s, 3H)

EXAMPLE 81

1-((7,7-Dimethyl-2-exo-hydroxy-2-endo-2-(1-(1—N-(methoxycarbonylethyl)prolyl)amino)propylbicyclo-(2.2.1)heptan-1-yl)methanesulfonyl)-4-(2-methyl-phenyl)piperazine

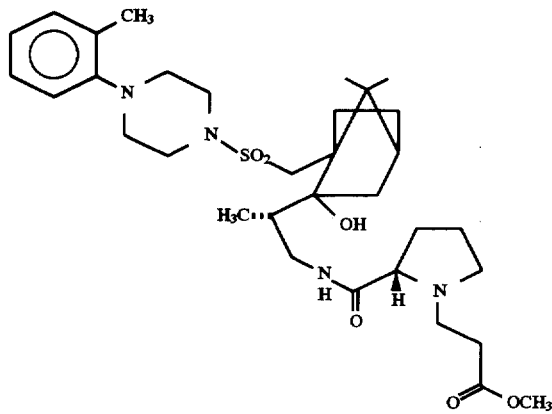

To a stirred solution of 1-((7,7-dimethyl-2-exo-hydroxy-2-endo-2-(1-(L-prolyl)amino)propyl-(2.2.1)bicycloheptan-1-yl)methanesulfonyl)-4-(2-methylphenyl)piperazine (1.50 g; 2.74 mmol) in methanol (15 mL) was added methyl acrylate (0.310 mL; 3.43 mmol). After 72 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: (C₃₃H₅₂N₄O₆S) Calc. C, 53.10; H, 6.59; N, 6.82 1.65 TFA Found C, 53.09; H, 6.58; N, 6.88

TLC: R/0.55 (95:5 CHCl₃:MeOH)

HPLC (method A): retention time 9.45 min

FAB MS: m/z 633 (M⁺+H)

¹H NMR (400 MHz, CDCl₃): d 7.18 (m, 2H), 7.03 (m, 2H), 4.55 (m, 1H), 3.72 (s, 3H), 2.32 (s, 3H), 1.15 (s, 3H), 1.04 (s, 3H), 1.01 (d, J=6 Hz, 3H)

EXAMPLE 82

1-((7,7-Dimethyl-2-exo-hydroxy-2-endo-2-(1-(1-N-(carboxyethyl)prolyl)amino)propyl-bicyclo(2.2.1)-heptan-1-yl)methanesulfonyl)-4-(2-methylphenyl)piperazine

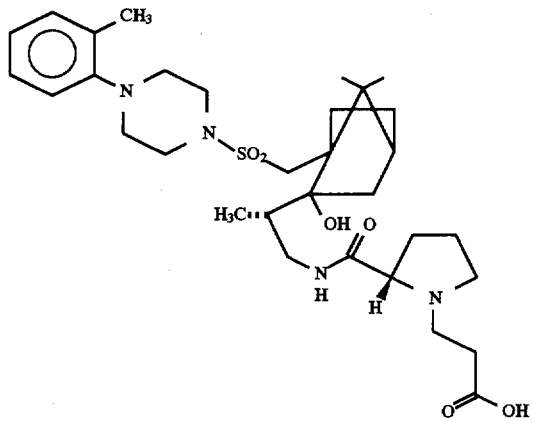

To a stirred solution of 1-((7,7-dimethyl-2-exo-hydroxy-2-endo-2-(1-(L-N-(methoxycarbonylethyl)-prolyl)amino)propyl-(2.2.1)bicyclo-heptan-1-yl)methanesulfonyl)-4-(2-methylphenyl)piperazine (1.00 g; FW=821; 1.22 mmol) in THF (15 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.

Anal: (C₃₂H₅₀N₄O₆S) Calc. C, 51.88; H, 6.34; N, 6.80 1.8 TFA Found C, 51.87; H, 6.28; N, 6.82

TLC: R/0.40 (80:20:2 CHCl₃:MeOH:NH₄OH)

HPLC (method A): retention time 8.88 min

FAB MS: m/z 619 (M⁺+H)

¹H NMR (400 MHz, CDCl₃): d 8.50 (br s, 1H), 7.20 (m, 2H), 7.05 (m, 2H), 2.33 (s, 3H), 1.12 (s, 3H), 1.03 (s, 3H), 0.99 (d, J=6 Hz, 3H)

EXAMPLE 83

1-((7,7-Dimethyl-2-exo-hydroxy-2-endo-2-(1-(3-piperidinylcarbonyl)amino)propyl-bicyclo(2.2.1)heptan-1-yl)methanesulfonyl)-4-(2-methylphenyl)piperazine

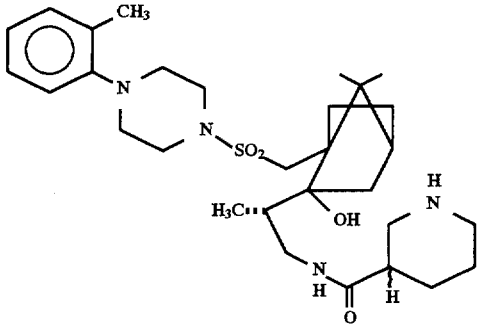

To a stirred solution of 1-((7,7-dimethyl-2-exo-hydroxy-2-endo-2-(1-amino)propyl-(2.2.1)bicycloheptan-1-yl)

methanesulfonyl)-4-(2-methylphenyl)piperazine (2.50 g; 5.57 mmol) in DMF (35 mL) was added N-Fmoc-piperidine-3-carboxylic acid (2.15 g; 6.13 mmol), BOP (2.75 g; 6.20 mmol), and DIEA (2.16 mL; 12.4 mmol). After 16 h, diethylamine (6 mL) was added and the solution was stirred at ambient temperature for 4 h. The solvents were removed under reduced pressure and the residue was dissolved in EtOAc (150 mL) and washed with aqueous NaHCO$_3$ (2×75 mL) and water (2×75 mL). The organic phase was dried (MgSO$_4$), filtered, and the solvent was removed under reduced pressure. The residue was purified by pressurized silica gel column chromatography, using 93:7:0.7 CHCl$_3$:MeOH:NH$_4$OH as eluant. The title compound (1:1 mixture of diastereomers) was obtained as a white foam.

Anal: (C$_{30}$H$_{48}$N$_4$O$_4$S) Calc. C, 56.37; H, 7.49; N, 8.54 0.8 CHCl$_3$ Found C, 56.49; H, 7.44; N, 8.50

TLC: R$_f$0.40 (90:10:1 CHCl$_3$:MeOH:NH$_4$OH)

HPLC (method A): retention time 8.67 min

FAB MS: m/z 561 (M$^+$+H)

$^1$H NMR (300 MHz, CDCl$_3$): d 7.50 (br s, 1H), 7.20 (m, 2H), 7.02 (m, 2H), 2.30 (s, 3H), 1.17 (s, 3H), 1.00–1.04 (overlapping singlet and doublet, 6H)

EXAMPLE 84

1-((7,7-Dimethyl-2-exo-hydroxy-2-endo-2-(1-(3-(1-methoxycarbonylethyl)piperidinylcarbonyl)-amino) propyl-bicyclo(2.2.1)heptan-1-yl)methanesulfonyl)-4-(2-methylphenyl)piperazine

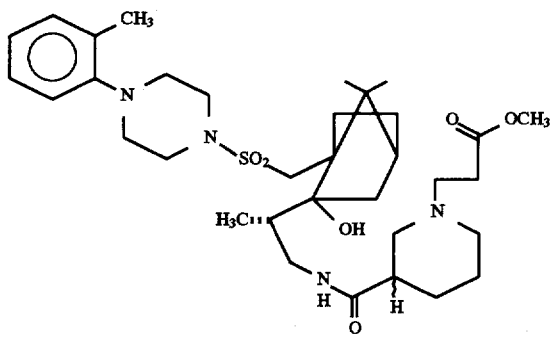

To a stirred solution of 1-((7,7-dimethyl-2-exo-hydroxy-2-endo-2-(1-(3-piperidinylcarbonyl)-amino)propyl-(2.2.1) bicycloheptan-1-yl)methansulfonyl)-4-(2-methylphenyl) piperazine (0.50 g; 0.89 mmol) in methanol (10 mL) was added methyl acrylate (0,120 mL; 1.34 mmol). After 72 h at ambient temperature, the solvent was removed under reduced pressure and the residue was purified by preparative reverse phase HPLC using an acetonitrile-water gradient containing 0.1% TFA. The TFA salt of title compound (1:1 mixture of diastereomers) was obtained as a lyophilized powder.

Anal: (C$_{34}$H$_{54}$N$_4$O$_6$S) Calc. C, 55.40; H, 7.06; N, 7.08 1.25 TFA, 0.1 H$_2$O Found C, 55.39; H, 7.05; N, 7.03

TLC: R$_f$0.35 (95:5 CHCl$_3$:MeOH)

HPLC (method A): retention time 10.71 min

FAB MS: m/z 647 (M$^+$+H)

1H NMR (400 MHz, CDCl$_3$): d 7.20 (m, 2H), 7.02 (m, 2H), 3,72, 3,69 (two singlets, 3H), 2.32, 2.31 (two singlets, 3H), 1.16, 1.15 (two singlets, 3H), 0.98–1.04 (two coincident singlets and two overlapping doublets, 6H)

EXAMPLE 85

1-((7,7-Dimethyl-2-exo-hydroxy-2-endo-2-(1-(3-(1-carboxyethyl)piperidinylcarbonyl)amino)-propylbicyclo(2.2.1)heptan-1-yl)methanesulfonyl)-4-(2-methylphenyl)piperazine

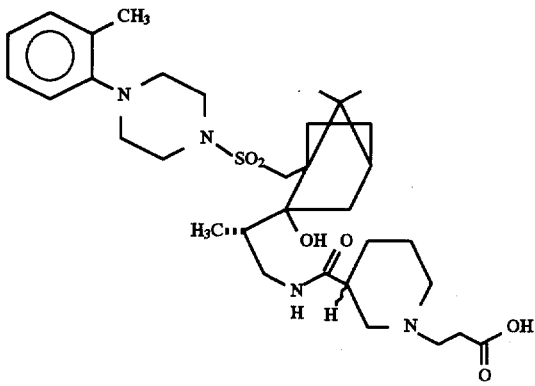

To a stirred solution of 1-((7,7-dimethyl-2-exo-hydroxy-2-endo-2-(1-(3-(1-methoxycarbonyl)piperidinylcarbonyl) amino)propyl( 2.2.1)-bicycloheptan-1-yl)methanesulfonyl)-4-(2-methylphenyl)piperazine (0.30 g; 0.46 mmol) in THF (10 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound (1:1 mixture of diastereomers) was obtained as a lyophilized powder.

Anal: (C$_{33}$H$_{52}$N$_4$O$_6$S) Calc. C, 51.59; H, 6.44; N, 6.54 1.9 TFA, 0.4 H$_2$O Found C, 51.60; H, 6.44; N, 6.83

TLC: R$_f$0.15 (80:20:2 CHCl$_3$:MeOH:NH$_4$OH)

HPLC (method A): retention time 10.27 min

FAB MS: m/z 633 (M$^+$+H)

$^1$H NMR (400 MHz, CDCl$_3$): d 7.20 (m, 2H), 7.05 (m, 2H), 2.39, 2.32 (two singlets, 3H), 1.12, 1.11 (two singlets, 3H), 0.95–1.03 (two coincident singlets and two overlapping doublets, 6H)

EXAMPLE 86

1-((7,7-Dimethyl-2-exo-hydroxy-2-endo-2-(1-(3-(1-ethoxycarbonylmethyl)piperidinylcar-bonyl)amino) propyl-bicyclo(2.2.1)heptan-1-yl)methanesulfonyl)-4-(2-methylphenyl)piperazine

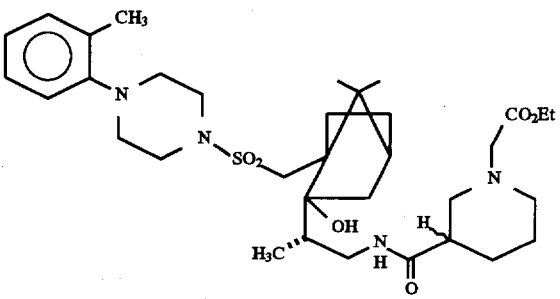

To a stirred solution of 1-((7,7-dimethyl-2-exo-hydroxy-2-endo-2-(1-(3-piperidinylcarbonyl)amino)-propyl-(2.2.1) bicycloheptan-1-yl)methanesulfonyl)-4-(2-methyl-phenyl) piperazine (0.50 g; 0.89 mmol) in DMF (5 mL) was added ethyl bromoacetate (0.110 mL; 0.99 mmol) and DIEA (0.172 mL; 0.99 mmol). After 24 h at ambient temperature, the solvent was removed under reduced pressure and the residue was dissolved in EtOAc (50 mL) and washed with 5% aqueous citric acid (25 mL), water (25 mL), and aqueous $NaHCO_3$ (25 mL). The organic phase was dried (MgSO4), filtered, and the solvents were removed under reduced pressure. The residue was purified by pressurized silica gel column chromatography, using 1:1 EtOAc:$CHCl_3$ as eluant. The title compound (1:1 mixture of diastereomers) was obtained as a white foam.

Anal: ($C_{34}H_{54}N_4O_6S$) Calc. C, 58.66; H, 7.77; N, 7.93 0.5 $CHCl_3$ Found C, 58.87; H, 7.83; N, 7.88

TLC: $R_f$0.28 (1:1 $CHCl_3$:EtOAc)

HPLC (method A): retention time 9.76 min

FAB MS: m/z 647 ($M^+$+H)

$^1$H NMR (300 MHz, $CDCl_3$): d 8.2 (very br s, 1H), 7.18 (m, 2H), 7.03 (m, 2H), 4.20 (two very closely spaced quartets, 2H), 2.30, 2.31 (two singlets, 3H), 1.28 (t, J=7 Hz, 3H), 1.07, 1.08 (two singlets, 3H), 1.03–1.08 (two coincident singlets and two overlapping doublets, 6H)

pressure. The residue was suspended in $CH_2Cl_2$ and filtered. The filtrate was evaporated under reduced pressure several times from $CH_2Cl_2$ to give the title compound (1:1 mixture of diastereomers) as a white foam.

Anal: ($C_{32}H_{50}N_4O_6S$) Calc. C, 58.27; H, 7.62; N, 7.99 1.0 NaOAc Found C, 58.47; H, 7.71; N, 7.90

TLC: $R_f$0.55 (85:15 $CHCl_3$:MeOH)

HPLC (method A): retention time 8.77 min

FAB MS: m/z 619 ($M^+$+H)

$^1$H NMR (300 MHz, $CD_3OD$): d 7.15 (m, 2H), 7.05 (d, J=7.3 Hz, 1H), 6.96 (t, J=7.3 Hz, 1H), 2.31 (s, 3H), 1.17 (s, 3H), 1.03 (s, 3H), 0.98 (d, J=6 Hz, 3H)

EXAMPLE 88

1-((7,7-Dimethyl-2-exo-hydroxy-2-endo-2-(1-(1-N -(ethoxycarboxymethyl)-prolyl)amino)propyl-bicyclo-(2.2.1)heptan-1-yl)methanesulfonyl)-4-(2-methylphenyl)piperazine

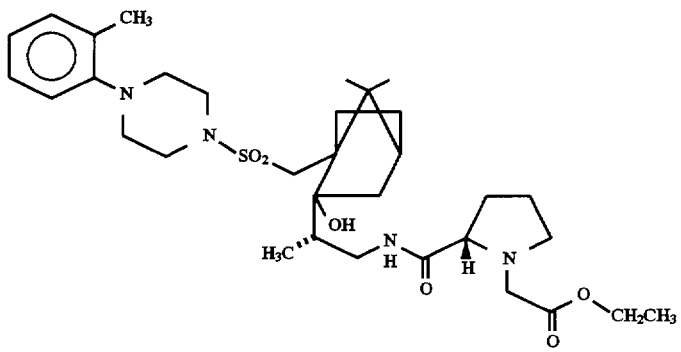

EXAMPLE 87

1-((7,7-Dimethyl-2-exo-hydroxy-2-endo-2-(1-(3-(1-carboxymethyl)piperidinylcarbonyl)amino)-propylbicyclo(2.2.1)heptan-1-yl)methanesulfonyl)-4-(2-methylphenyl)piperazine

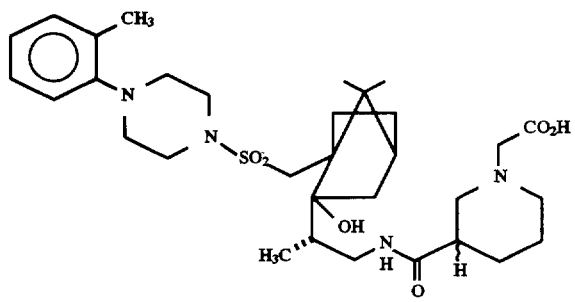

To a stirred solution of 1-((7,7-dimethyl-2-exo-hydroxy-2-endo-2-(1-(3-(1-methoxycarbonyl)-piperidinylcarbonyl)amino)propyl-(2.2.1)bicycloheptan-1-yl)methanesulfonyl)-4-(2-methylphenyl)piperazine (0.360 g; 0.555 mmol) in THF (5 mL) was added 1M NaOH until a pH 10 solution persisted for 1 h. The solution was made acidic by the addition of HOAc (1 mL) and evaporated under reduced To a stirred solution of 1-((7,7-dimethyl-2-exo-hydroxy-2-endo-2-(1-(L-prolyl)amino)propyl(2.2.1)-bicycloheptan-1-yl)methanesulfonyl)-4-(2-methylphenyl)-piperazine (0.20 g; 0.37 mmol) in DMF (5 mL) was added ethyl bromoacetate (0.045 mL; 0.40 mmol) and DIEA (0.071 mL; 0.41 mmol). After 24 h at ambient temperature, the solvent was removed under reduced pressure and the residue was purified by preparative reverse phase HPLC using an acetonitrile-water gradient containing 0.1% TFA. The TFA salt of title compound was obtained as a lyophilized powder.

Anal: ($C_{33}H_{52}N_4O_6S$) Calc. C, 54.25; H, 6.79; N, 7.07 1.4 TFA Found C, 54.25; H, 6.78; N, 7.02

TLC: $R_f$0.50 (1:1 EtOAc:$CHCl_3$)

HPLC (method A): retention time 9.68 min

FAB MS: m/z 633 ($M^+$+H)

$^1$H NMR (400 MHz, $CD_3OD$): d 7.17 (m, 2H), 7.06 (d, J=6 Hz, 1H), 6.98 (t, J=6 Hz, 1H), 4.25 (m, 3H), 4.08 (d, J=15 Hz, 1H), 2.32 (s, 3H), 1.27 (t, J=7 Hz, 3H), 1.18 (s, 3H), 1.03 (s, 3H), 1.01 (d, J=6 Hz, 3H)

EXAMPLE 89

1-((7,7-Dimethyl-2-exo-hydroxy-2-endo-2-(1-(1-N-(carboxymethyl)prolyl)amino)propyl-bicyclo(2.2.1)-heptan-1-yl)methanesulfonyl)-4-(2-methanesulfonyl) piperazine

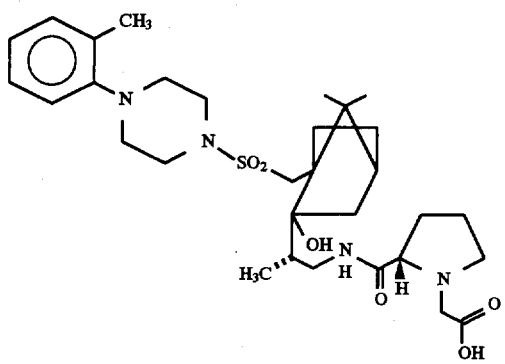

To a stirred solution of 1-((7,7-dimethyl-2-exo-hydroxy-2-endo-2-(1-(L-(N-ethoxycarbonylmethyl)- prolyl)amino)propyl(2.2.1)bicycloheptan-1-yl)methane-sulfonyl)-4-(2-methylphenyl)piperazine (0.20 g; 0.32 mmol) in THF (5 mL) was added 1M NaOH until a pH 10 solution persisted for 1 h. The solvent was removed under reduced pressure and the residue was purified by preparative reverse phase HPLC using an aceto-nitrile-water gradient containing 0.1% TFA. The TFA salt of title compound was obtained as a lyophilized powder.

Anal: ($C_{31}H_{48}N_4O_6S$) Calc. C, 52.64; H, 6.43; N, 7.22 1.5 TFA Found C, 52.49; H, 6.51; N, 7.22

TLC: $R_f$ 0.40 (80:20:2 $CHCl_3$:MeOH:$NH_4OH$)

HPLC (method A): retention time 8.79 min

FAB MS: m/z 605 ($M^+$+H)

$^1$H NMR (400 MHz, $CD_3OD$): d 7.17 (m, 2H), 7.07 (d J=5 Hz, 1H), 6.99 (t, J=5 Hz, 1H), 4.30 (dd, J=4, 5 Hz, 1H), 4.21 (d, J=14 Hz, 1H), 4.04 (d, J=14 Hz, 1H), 2.32 (s, 3H), 1.18 (s, 3H), 1.03 (s, 3H), 1.01 (d, J=7 Hz, 3H)

EXAMPLE 90

1-((7,7-Dimethyl-2-exo-hydroxy-2-endo-2-(1-(4-piperidinylcarbonyl)amino)propyl-bicyclo(2.2.1) heptan-1-yl)methanesulfonyl)-4-(2-methanesulfonyl) piperazine

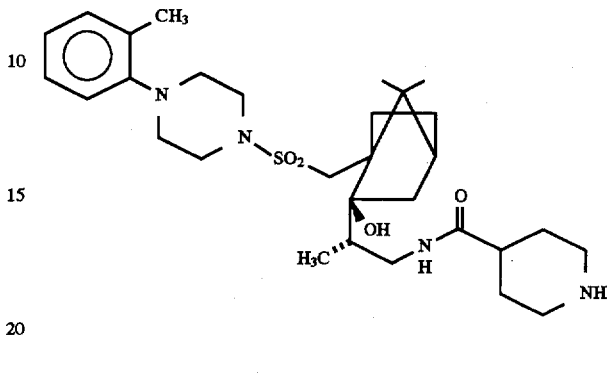

To a stirred solution of 1-((7,7-dimethyl-2-exo-hydroxy-2-endo-2-(1-amino)propyl-(2.2.1)bicycloheptan-1-yl) methanesulfonyl)-4-(2-methylphenyl)piperazine (1.50 g; 3.34 mmol) in DMF (20 mL) was added N-Fmoc-piperidine-4-carboxylic acid (1.29 g; 3.67 mmol), BOP (1.64 g; 3.70 mmol), and DIEA (1.28 mL; 7.34 mmol). After 16 h, diethylamine (5 mL) was added and the solution was stirred at ambient temperature for 4 h. The solvents were removed under reduced pressure and the residue was purified by preparative reverse phase HPLC using an acetonitrile-water gradient containing 0.1% TFA. The TFA salt of title compound was obtained as a lyophilized powder.

Anal: ($C_{30}H_{48}N_4O_4S$) Calc. C, 51.93; H, 6.43; N, 7.15 1.95 TFA, 0.05 $H_2O$ Found C, 51.93; H, 6.36; N, 7.28

TLC: $R_f$ 0.15 (90:10:1 $CHCl_3$:MeOH:$NH_4OH$)

HPLC (method A): retention time 8.33 min

FAB MS: m/z 561 ($M^+$+H)

$^1$H NMR (400 MHz, $CDCl_3$): d 7.20 (m, 3H), 7.08 (m, 2H), 2.33 (s, 3H), 1.14 (s, 3H), 1.02 (s, 3H), 1.00 (d, J=6 Hz, 3H)

EXAMPLE 91

1-((7,7-Dimethyl-2-exo-hydroxy-2-endo-2-(1-(4-(1-methoxycarbonylethyl)-piperidinylcarbonyl)-amino) propylbicyclo(2.2.1)heptan-1-yl)methane-sulfonyl)-4-(2-methylphenyl)piperazine

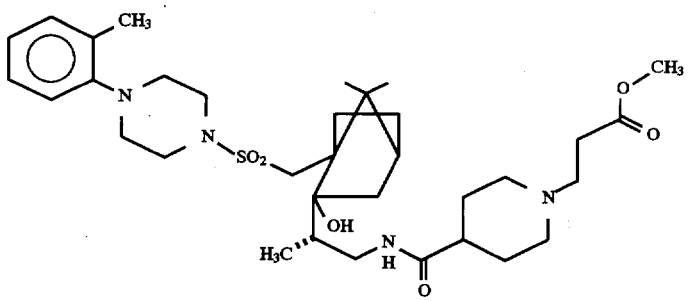

To a stirred solution of 1-((7,7-dimethyl-2-exo-hydroxy-2-endo-2-(1-(4-piperidinylcarbonyl)amino)-propyl-(2.2.1) bicycloheptan-1-yl)methane-sulfonyl)-4-(2-methylphenyl) piperazine (0.30 g; 0.53 mmol) in methanol (5 mL) was added methyl acrylate (0.072 mL; 0.80 mmol). After 48 h at ambient temperature, the solvent was removed under reduced pressure and the residue was purified by preparative reverse phase HPLC using an acetonitrile- water gradient containing 0.1% TFA. The TFA salt of title compound was obtained as a lyophilized powder.

Anal: ($C_{34}H_{54}N_4O_6S$) Calc. C, 53.04; H, 6.65; N, 6.60 1.75 TFA, 0.15 $H_2O$ Found C, 53.05; H, 6.62; N, 6.69

TLC: $R_f$ 0.25 (95:5 $CHCl_3$:MeOH)

HPLC (method A): retention time 9.02 min

FAB MS: m/z 647 ($M^+$+H)

$^1$H NMR (400 MHz, $CDCl_3$): d 7.45 (br t, 1H), 7.21 (m, 2H), 7.09 (m, 2H), 3.72 (s, 3H), 2.33 (s, 3H), 1.15 (s, 3H), 1.00–1.02 (overlapping s and d, 6H)

EXAMPLE 92

1-((7,7-Dimethyl-2-exo-hydroxy-2-endo-2-(1-(4-(1-carboxyethyl)piperidinylcarbonyl)amino)propyl-bicyclo-(2.2.1)heptan-1-yl)methanesulfonyl)-4-(2-methylphenyl)piperazine

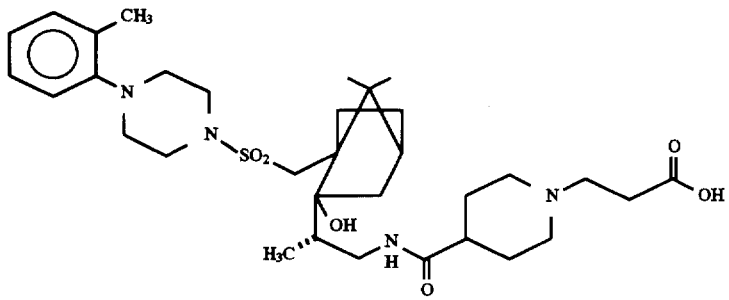

To a stirred solution of 1-((7,7-dimethyl-2-exo-hydroxy-2-endo-2-(1-(3-(1-methoxycarbonyl)pipe-ridinylcarbonyl) amino)propyl-(2.2.1)bicycloheptan-1-yl)methanesulfonyl)-4-(2-methylphenyl)piperazine (0.15 g; 0.23 mmol) in THF (5 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.

Anal: ($C_{33}H_{52}N_4O_6S$) Calc. C, 53.09; H, 6.65; N, 6.84 1.6 TFA, 0.2 $H_2O$ Found C, 53.08; H, 6.66; N, 6.85

TLC: $R_f$ 0.10 (80:20:2 $CHCl_3$:MeOH:$NH_4OH$)

HPLC (method A): retention time 8.72 min

FAB MS: m/z 633 ($M^+$+H)

1H NMR (400 MHz, $CDCl_3$): d 7.38 (br s, 1H), 7.18 (m, 2H), 7.03 (m, 2H), 2.29 (s, 3H), 1.13 (s, 3H), 0.98–1.01 (overlapping s and d, 6H)

EXAMPLE 93

1-((7,7-Dimethyl-2-exo-hydroxy-2-endo-2-(1-(3-(1-ethoxycarbonylmethyl)piperidinylcar-bonyl)amino) propyl-bicyclo(2.2.1)heptan-1-yl)methanesulfonyl)-4-(2-methylphenyl)piperazine

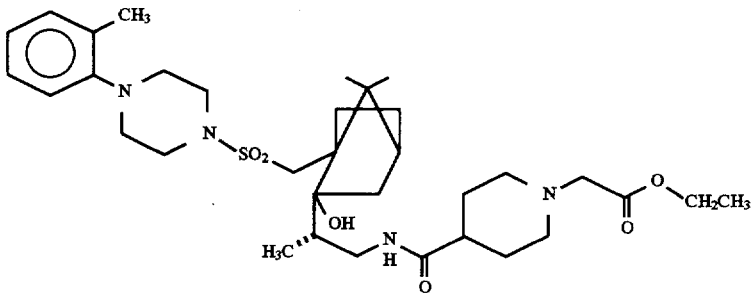

To a stirred solution of 1-((7,7-dimethyl-2-exo-hydroxy-2-endo-2-(1-(3-piperidinylcarbonyl)amino)-propyl-(2.2.1) bicycloheptan-1-yl)methanesulfonyl)-4-(2-methylphenyl) piperazine (0.20 g; 0.36 mmol) in DMF (5 mL) was added ethyl bromoacetate (0.044 mL; 0.40 mmol) and DIEA (0.070 mL; 0.40 mmol). After 24 h at ambient temperature, the solution was evaporated under reduced pressure and the residue was purified by preparative reverse phase HPLC using an acetonitrile-water gradient containing 0.1% TFA.

The TFA salt of title compound was obtained as a lyophilized powder.

Anal: ($C_{34}H_{54}N_4O_6S$) Calc. C, 52.81; H, 6.67; N, 6.57 1.75 TFA, 0.35 $H_2O$ Found C, 52.80; H, 6.64; N, 6.69

TLC: $R_f$ 0.35 (95:5 $CHCl_3$:MeOH)

HPLC (method A): retention time 9.26 min

FAB MS: m/z 647 ($M^+$+H)

$^1$H NMR (400 MHz, $CDCl_3$): d 7.19 (m, 2H), 7.04 (m, 2H), 4.26 (q, J=7 Hz, 2H), 3.85 (s, 2H), 2.32 (s, 3H), 1.29 (t, J=7 Hz, 3H), 1.14 (s, 3H), 1.02–1.05 (overlapping s and d, 6H)

EXAMPLE 94

1-((7,7-Dimethyl-2-exo-hydroxy-2-endo-2-(1-(4-(1-carboxymethyl)piperidinylcarbonyl)amino)propyl-bicyclo(2.2.1)heptan-1-yl)methanesulfonyl)-4-(2-methylphenyl)piperazine

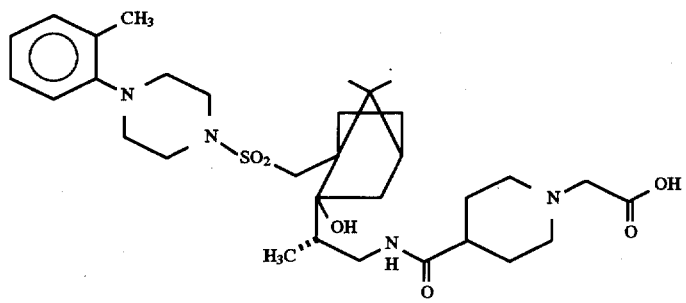

To a stirred solution of 1-((7,7-dimethyl-2-exo-hydroxy-2-endo-2-(1-(3-(1-methoxycarbonylmethyl)piperidinylcarbonyl)amino)propyl-(2.2.1)bicycloheptan-1-yl)methanesulfonyl)-4-(2-methylphenyl)piperazine (0.15 g; 0.23 mmol) in THF (5 mL) was added 1M NaOH until a pH 10 solution persisted for 1 h. The solution was evaporated under reduced pressure and the residue was purified by preparative reverse phase HPLC using an acetonitrile-water gradient containing 0.1% TFA. The TFA salt of title compound was obtained as a lyophilized powder.

Anal: ($C_{32}H_{50}N_4O_6S$) Calc. C, 53.23; H, 6.82; N, 7.18 1.3 TFA, 0.75 $H_2O$ Found C, 53.20; H, 6.81; N, 7.18

TLC: $R_f$ 0.15 (80:20:2 $CHCl_3$:MeOH:$NH_4OH$)

HPLC (method A): retention time 8.59 min

FAB MS: m/z 619 ($M^+$+H)

$^1$H NMR (400 MHz, $CDCl_3$): d 7.35 (br s, 1H), 7.17 (m, 2H), 7.02 (m, 2H), 3.90 (s, 2H), 2.30 (s, 2H), 1.13 (s, 3H), 1.01 (s, 3H), 0.97 (d, J=6 Hz, 3H)

EXAMPLE 95

1-((7,7-Dimethyl-2-endo-(2S-diethylamino-4-(methylsulfonyl)butyramido)-bicyclo(2.2.1)heptan-1-yl)methanesulfonyl)-4-(2-methylphenyl)piperazine

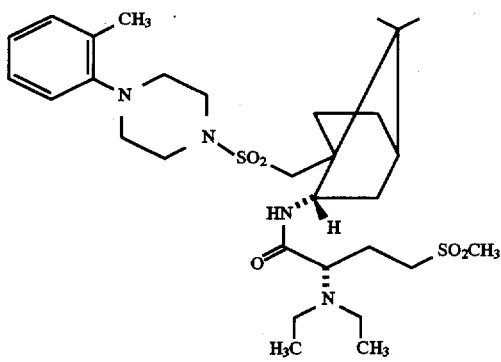

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)-piperazine (100 mg; 0.18 mmol) in methanol containing 1% acetic acid (2 mL) was added acetaldehyde (0.033 mL; 0.6 mmol) and sodium cyanoborohydride (10 mg; 0.18 mmol). After 2 h, the reaction was quenched with sodium bicarbonate solution (0.5 mL) and the solvent was removed under reduced pressure. The residue was taken up in ethyl acetate (25 mL) and washed with saturated aqueous sodium bicarbonate (2×25 mL), brine (2×25 mL), dried over magnesium sulfate, and filtered. The solvent was removed under reduced pressure. The residue was purified by silica gel flash column chromatography eluting with 95:5:0.5 CHCl₃: CH₃OH:NH₄OH. The title compound was obtained as a white foam by evaporation under reduced pressure from ether-chloroform in 85% yield.

Analysis: $C_{30}H_{50}N_4O_5S_2$, 0.7 CHCl₃, 0.2 $(CH_3CH_2)_2O$ calc. C 53.65 H 7.51 N 8.01 found 53.64 7.50 8.13

TLC: $R_f$=0.38 (95:5:0.5 CHCl₃:MeOH:NH₄OH)

HPLC (method A): retention time=9.66 min, purity=95%

FAB MS: m/z=611 (M +H⁺)

EXAMPLE 96

1-((7,7-Dimethyl-2-endo-(2S-ethoxycarbonylmethyl-amino-4-(methylsulfonyl) butyramido)-bicyclo(2.2.1)-heptan-1-yl) methanesulfonyl)-4-(2-methylphenyl)piperazine

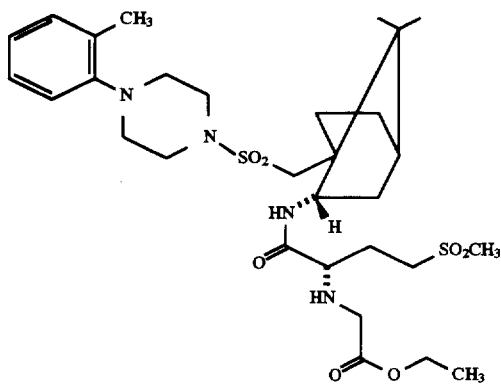

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)-piperazine (200 mg; 0.36 mmol) in DMF (3 mL) was added DIEA (0.070 mL; 0.40 mmol) and ethyl bromoacetate (0.044 mL; 0.40 mmol). After 24 h, the solvent was removed under reduced pressure. The residue was taken up in ethyl acetate (50 mL) and washed with 5 wt % aqueous citric acid (2×25 mL) and saturated sodium bicarbonate solution (2×25 mL). The organic phase was dried (MgSO₄), filtered, and the solvent was removed under reduced pressure. The residue was purified by silica gel flash column chromatography eluting with 95:5 CHCl₃:CH₃OH. The title compound was obtained as a white foam by evaporation under reduced pressure from EtOAc-hexane in 75% yield.

Analysis: $C_{30}H_{48}N_4O_7S_2$, 0.4 EtOAc, 0.05 hexane calc. C 56.30 H 7.69 N 8.23 found C 56.22 H 7.70 N 8.25

TLC: $R_f$=0.35 (95:5 CHCl₃:MeOH)

HPLC (method A): retention time=9.67 min, purity= 99+%

FAB MS: m/z=641 (M+H⁺)

EXAMPLE 97

1-((7,7-Dimethyl-2-endo-(2S-carboxymethylamino-4-(methylsulfonyl)butyramido)-bicyclo(2.2.1) heptan-1-yl)methanesulfonyl)-4-(2-methylphenyl) piperazine

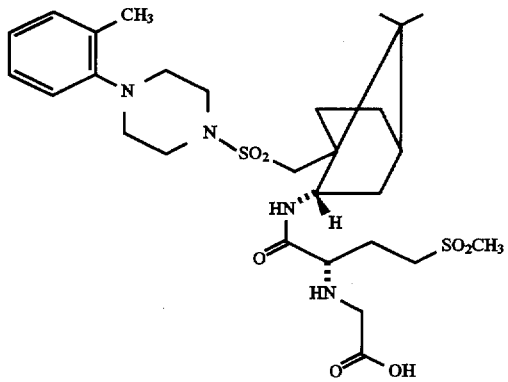

To a stirred solution of 1-((7,7-dimethyl-2-endo-(2S-ethoxycarbonyl-methylamino-4-(methyl -sulfonyl) butyramido)bicyclo(2.2.1)heptan-1-yl)methanesulfonyl)-4-(2-methylphenyl)piperazine (50 mg; 0.08 mmol) in ethanol, was added 1N aqueous sodium hydroxide to obtain a pH 13 reaction solution. After 24 h, the reaction was acidified to pH 2 with 5% aqueous HCl and the solvent was removed under reduced pressure. The residue was taken up in methylene chloride (25 mL), washed with brine (25 mL), dried over magnesium sulfate, and filtered. The solvent was removed under reduced pressure. The residue was triturated in ether and filtered to give the title compound as a white solid in 75% yield.

Analysis: $C_{28}H_{44}N_4O_7S_2$, 0.5 NaCl calc. C 52.38 H 6.91 N 8.73 found C 52.43 H 6.55 N 8.80

TLC: $R_f$=0.2 (90:10:0.2:0.2 CHCl₃:MeOH:H₂O:HOAc)

HPLC (method A): retention time=8.91 min, purity=99%

FAB MS: m/z=613 (M+H⁺)

EXAMPLE 98

1-((7,7-Dimethyl-2-endo-(2S-amino-4-(methylsulfonyl)-butyramido)bicyclo(2.2.1)heptan-1-yl)methanesulfonyl)-4-(2-methyl-5-fluorophenyl) piperazine

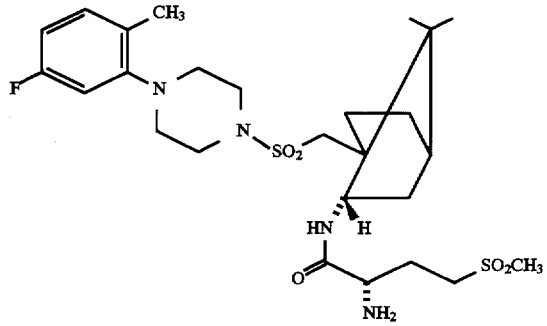

The title compound was prepared from 1-((7,7-dimethyl-2-endo-amino-bicyclo(2.2.1)heptan-1-yl)methane-sulfonyl) -4-(2-methyl-5-fluoro-phenyl)piperazine and Boc-L-methionine sulfone using the procedures set forth in Examples 71 and 72. The crude product was purified by preparative reverse phase HPLC using an acetonitrile-water gradient containing 0.1% trifluoroacetic acid. The trifluoroacetate salt of the title compound was obtained by lyophilization to give a white powder in 85% yield.

Analysis: $C_{26}H_{41}FN_4O_5S_2$, $0.3H_2O$, $1.7\ CF_3COOH$ calc. C 45.74 H 5.65 N 7.26 found C 45.74 H 5.65 N 7.50

TLC: $R_f$=0.18 (95:5:0.5 $CHCl_3$:MeOH:$NH_4OH$)

HPLC (method A): retention time=8.86 min, purity=99%

FAB MS: m/z=573 (M+H$^+$)

EXAMPLE 99

1-((7,7-Dimethyl-2-endo-(2S-dimethylamino-4-(methyl-sulfonyl)butyramido)-bicyclo(2.2.1)heptan-1-yl)methanesulfonyl)-4-(2-methyl-5-fluorophenyl)piperazine

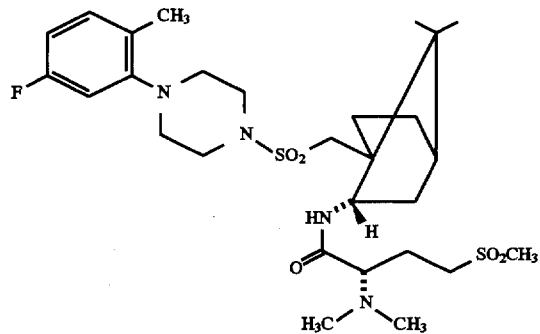

The title compound was prepared from 1-((7,7-dimethyl-2-endo-)2S-amino-4-(methylsulfonyl)-butyramido)-bicyclo(2.2.1)heptan-1-yl)methanesulfonyl)-4-(2-methyl-5-fluorophenyl)piperazine using the procedure set forth in Example 74. The crude product was purified by preparative reverse phase HPLC using an acetonitrile-water gradient containing 0.1% trifluoroacetic acid. The trifluoroacetate salt of the title compound was obtained by lyophilization to give a white powder in 90% yield.

Analysis: $C_{28}H_{45}FN_4O_5S_2$, $0.05\ H_2O$, $1.65\ CF_3COOH$ calc. C 47.59 H 5.97 N 7.09 found C 47.56 H 5.91 N 7.15

TLC: $R_f$=0.39 (95:5:0.5 $CHCl_3$:MeOH:$NH_4OH$)

HPLC (method A): retention time=9.82 min, purity=99%

FAB MS: m/z=601 (M+H$^+$)

EXAMPLE 100

1-((7,7-Dimethyl-2-endo-(2S-(1-piperidinyl)-4-(methylsulfonyl)butyramido)-bicyclo(2.2.1)heptan-1-yl)methanesulfonyl)-4-(2-methylphenyl)piperazine

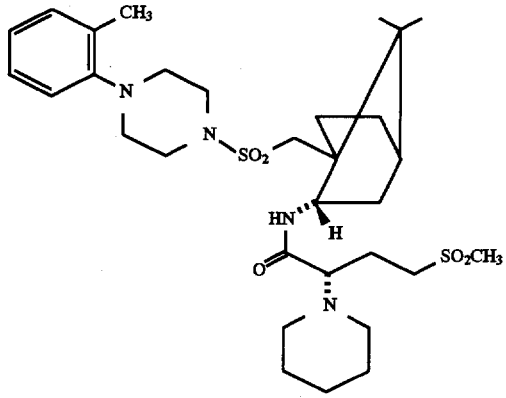

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methyl-phenyl)piperazine (100 mg; 0.18 mmol) in methanol containing 1% by volume of acetic acid in methanol (5 mL) was added glutaraldehyde (25 wt % in water; 0.005 mL; 0.22 mmol) and sodium cyanoboro-hydride (30 mg; 0.54 mmol). After 3 h, the reaction was quenched with aqueous sodium bicarbonate solution (0.5 mL) and the solvent was removed under reduced pressure. The residue was taken up in ethyl acetate (25 mL) and washed with saturated aqueous sodium bicarbonate (2×25 mL), brine (2×25 mL), dried over magnesium sulfate, and filtered. The solvent was removed under reduced pressure. The title compound was obtained as a white foam in 90% yield.

Analysis: $C_{31}H_{50}N_4O_5S_2$, $0.85\ H_2O$, calc. C 58.33 H 8.17 N 8.78 found C 58.31 H 7.77 N 8.67

TLC: $R_f$=0.45 (95:5:0.5 $CHCl_3$:MeOH:$NH_4OH$)

HPLC (method A): retention time=8.72 min, purity=99+%

FAB MS: m/z=623 (M+H$^+$)

EXAMPLE 101

1-((7,7-Dimethyl-2-endo-(2S-(2-hydroxyethyl)amino-4-(methylsulfonyl)-butyramido)-bicyclo(2.2.1)heptan-1-yl)methanesulfonyl)-4-(2-methylphenyl)piperazine

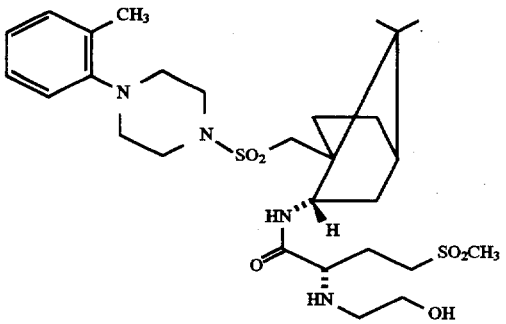

A stirred solution of 1-((7,7-dimethyl-2-endo-(2S-amino-4-(methylsulfonyl)butyramido)-bicyclo(2.2.1)-heptan-1-yl)

methanesulfonyl)-4-(2-methylphenyl)-piperazine (310 mg, 0.56 mmol) in ethanol (10 mL) was cooled to 0° C. Ethylene oxide was bubbled through the solution, the reaction vessel was sealed, and the reaction mixture was warmed to 70° C. After 48 h, the solvent was removed under reduced pressure. The residue was purified by silica gel flash column chromatography using a gradient elution of 97:3 to 93:7 CHCl$_3$:MeOH to separate the faster running bis-alkylated product from the mono-alkylation product. The title compound was obtained as a white foam by evaporation under reduced pressure from CHCl$_3$-MeOH in 60% yield.

Analysis: C$_{28}$H$_{46}$N$_4$O$_6$S$_2$, 0.4 CHCl$_3$, 0.15 MeOH, calc. C 52.64 H 7.27 N 8.60 found C 52.67 H 7.27 N 8.37

TLC: R$_f$=0.15 (93:7 CHCl$_3$:MeOH)

HPLC (method A): retention time=8.72 min, purity=99%

FAB MS: m/z=599 (M+H$^+$)

EXAMPLE 102

1-((7,7-Dimethyl-2-endo-(2S-(4-morpholinyl)-4-(methylsulfonyl)butyramido)-bicyclo(2.2.1)heptan-1-yl)methanesulfonyl)-4-(2-methylphenyl)piperazine

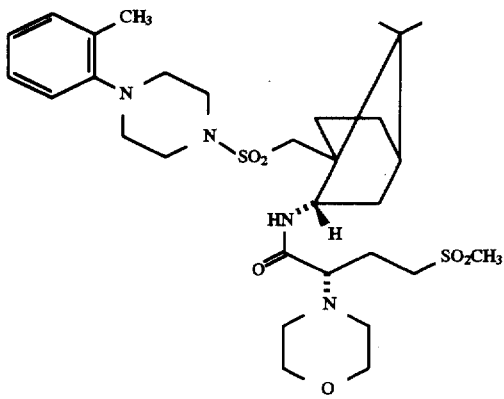

To a solution of 1-((7,7-dimethyl-2-endo-(2S-amino-4-(methylsulfonyl)butyramido)-bicyclo(2.2.1)heptan-1-yl) methanesulfonyl)-4-(2-methylphenyl)piperazine (100 mg, 0.18 mmol) in DMF (3 mL) was added bis(2-chloroethyl)-ether (0.029 mL; 0.25 mmol), sodium iodide (75 mg; 0.5 mmol), and sodium carbonate (80 mg; 0.75 mmol). The mixture was flushed with argon and heated at 130° C. for 6 h. The solvent was removed under reduced pressure. The residue was suspended in ethyl acetate (50 mL) and washed with water (2×25 mL), saturated aqueous sodium bicarbonate (2×25 mL), brine (25 mL), dried over magnesium sulfate, and filtered. The solvent was removed under reduced pressure and the residue was purified by preparative reverse phase HPLC using an acetonitrile-water gradient containing 0.1% trifluoroacetic acid. The trifluoroacetate salt of the title compound was obtained by lyophilization to give a white powder in 25% yield.

Analysis: C$_{30}$H$_{48}$N$_4$O$_6$S$_2$, 3.0 CF$_3$CO$_2$H, 0.5 H$_2$O calc. C 44.31 H 5.37 N 5.74 found C 44.20 H 5.04 N 6.10

TLC: R$_f$=0.63 (95:5:0.5 CHCl$_3$:MeOH:NH$_4$OH)

HPLC (method A): retention time=9.08 min, purity=100%

FAB MS: m/z=625 (M+H$^+$)

EXAMPLE 103

1-((7,7-Dimethyl-2-endo-(2S-cyanomethylamino-4-(methylsulfonyl)butyramido)-bicyclo(2.2.1)heptan-1-yl)methanesulfonyl)-4-(2-methylphenyl)piperazine

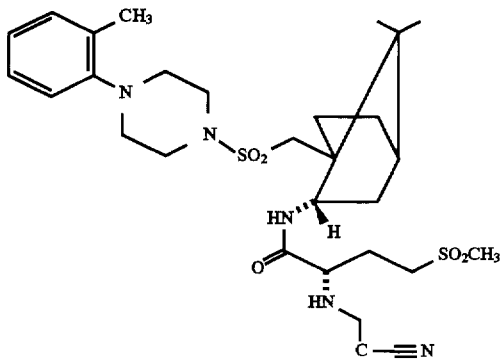

To a solution of 1-((7,7-dimethyl-2-endo-(2S-amino-4-(methylsulfonyl)butyramido)-bicyclo(2.2.1)heptan-1-yl) methanesulfonyl)-4-(2-methylphenyl)piperazine (100 mg, 0.18 mmol) in chloroform (5 mL) was added DIEA (0.037 mL; 0.21 mmol) followed by iodoacetonitrile (0.015 mL; 0.21 mmol). After 24 h, the reaction was diluted with chloroform (50 mL) and washed with water (25 mL), saturated aqueous sodium bicarbonate (2×25 mL), brine (25 mL), dried over magnesium sulfate, and filtered. The solvent was removed under reduced pressure and the residue was purified by flash silica gel column chromatography using 97:3 dichloromethane:methanol as eluant. The title compound was obtained as a white foam in 70% yield.

Analysis: C$_{28}$H$_{43}$N$_5$O$_5$S$_2$, 0.5 H$_2$O calc. C 55.79 H 7.36 N 11.67 found C 56.15 H 7.42 N 11.32

TLC: R$_f$=0.45 (95:5:0.5 CHCl$_3$:MeOH:NH$_4$OH)

HPLC (method A): retention time=9.78 min, purity=100%

FAB MS: m/z=594 (M+H$^+$)

EXAMPLE 104

1-((7,7-Dimethyl-2-endo-(2S-(4-tetra-hydropyranyl) amino-4-(methylsulfonyl)-butyramido)-bicyclo (2.2.1)heptan-1-yl)methanesulfonyl)-4-(2-methylphenyl)piperazine

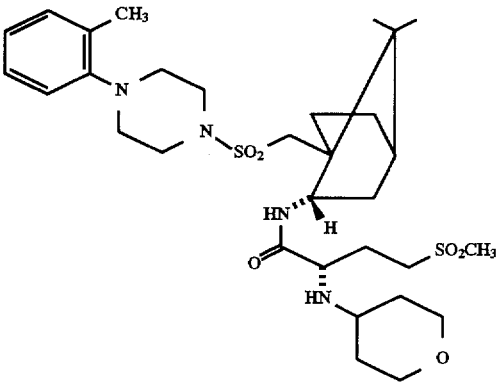

To a stirred solution of 1-((7,7-dimethyl-2-endo-(2S-amino-4-(methylsulfonyl)butyramido)-bicyclo(2.2.1)- heptan-1-yl)methanesulfonyl)-4-(2-methylphenyl)-piperazine (200 mg; 0.36 mmol) in methanol containing 1% by volume of acetic acid (4 mL) was added 4–5 molecular sieves (3 Å), tetrahydropyran-4-one (0.037 mL, 0.37 mmol) and sodium cyanoborohydride (20 mg; 0.36 mmol). After 2 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The title compound was obtained in 90% yield as a white foam.

Analysis: $C_{31}H_{50}N_4O_6S_2$, 0.45 EtOAc, calc. C 58.05 H 7.96 N 8.26 found C 57.81 H 7.71 N 8.28

TLC: $R_f$=0.27 (95:5:0.5 $CHCl_3$:MeOH:$NH_4OH$)

HPLC (method A): retention time=8.29 min, purity=99%

FAB MS: m/z=639 (M+H$^+$)

EXAMPLE 105

1-((7,7-Dimethyl-2-endo-(2S-(2-aminoethyl)amino-4-(methylsulfonyl)butyramido)-bicyclo(2.2.1)heptan-1-yl)methanesulfonyl)-4-(2-methylphenyl)piperazine

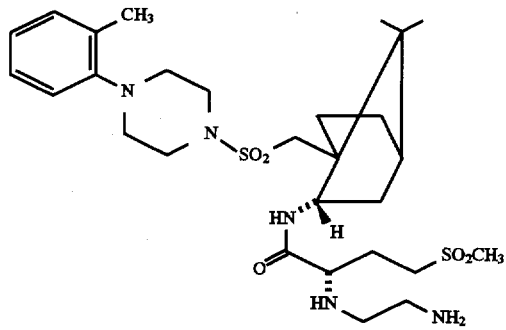

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (200 mg; 0.36 mmol) in methanol containing 1% by volume of acetic acid (4 mL) was added 4–5 molecular sieves (3 Å), N-Boc-glycinal (62 mg, 0.39 mmol) and sodium cyanoboro-hydride (20 mg; 0.36 mmol). After 2 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The residue was purified by silica gel flash column chromatography using 95:5 chloroform:methanol as eluant to give 1-((7,7-dimethyl-2-endo-(2S-(2-(tert-butyloxycarbonylamino)ethyl)amino-4-(methylsulfonyl)butyramido)-bicyclo(2.2.1)heptan-1-yl)methanesulfonyl)-4-(2-methylphenyl)piperazine in 80% yield. This compound was dissolved in methylene chloride (7 mL) and to the solution was added trifluoroacetic acid (7 mL). After 30 min the solvent was removed under reduced pressure. The residue was taken up in methylene chloride (70 mL) and washed with saturated aqueous sodium bicarbonate (3×100 mL), brine (2×50 mL), dried over magnesium sulfate, and filtered. The solvent was removed under reduced pressure. The title compound was lyophilized from dioxane-water to give a white powder in 90% yield.

Analysis: $C_{28}H_{47}N_5O_5S_2$, 0.5 $C_4H_8O_2$, 1.5 $H_2O$ calc. C 53.87 H 8.14 N 10.47 found C 54.04 H 8.96 N 10.44

TLC: $R_f$=0.08 (90:10:0.5 $CHCl_3$:MeOH:$NH_4OH$)

HPLC (method A): retention time=9.30 min, purity=99%

FAB MS: m/z=598 (M+H$^+$)

EXAMPLE 106

1-((7,7-Dimethyl-2-endo-(2R-amino-4-(methylsulfonyl)-butyramido)-bicyclo(2.2.1)heptan-1-yl)methanesulfonyl)-4-(2-methylphenyl)piperazine

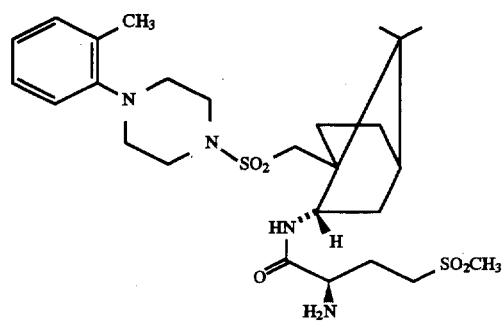

1-((7,7-Dimethyl-2-endo-(2R-(tert-butyloxycarbonyl)amino-4-(methylthio)butyramido)-bicyclo(2.2.1)-heptan-1-yl)methanesulfonyl)-4-(2-methylphenyl)-piperazine was prepared from Boc-D-methionine and 1-((7,7-dimethyl-2-endo-amino-bicyclo(2.2.1)heptan-1-yl)methanesulfonyl)-4-(2-methylphenyl)piperazine using the procedure set forth in Example 35. 1-((7,7-Dimethyl-2-endo-(2R-(tert-butyloxycarbonyl)amino-4-(methylthio)butyramido)-bicyclo(2.2.1)heptan-1-yl)methanesulfonyl)-4-(2-methylphenyl)piperazine (200 mg; 0.32 mmol) was dissolved in 3:1 MeOH:water (25 mL) and to the solution was added sodium acetate (200 mg; 2.6 mmol) and Oxone® (0.80 g; 1.3 mmol). After 24 h, the solvents were removed under reduced pressure and the residue was purified by silica gel flash column chromatography using 90:10:1 $CHCl_3$:MeOH:$NH_4OH$ as eluant to give 1-((7,7-dimethyl-2-endo-(2R-(tert-butyloxycarbonyl)amino-4-(methylsulfonyl)butyramido)-bicyclo(2.2.1)heptan-1-yl)methanesulfonyl)-4-(2-methylphenyl)piperazine-4-N-oxide as a foam from chloroform in 70% yield. This product was dissolved in THF (3 mL) and treated with triphenylphosphine (79 mg; 0.35 mmol). After 24 h the solvent was removed under reduced pressure and the residue was purified by silica gel flash column chromatography using 1:1 EtOAc:hexane as eluant to give 1-((7,7-dimethyl-2-endo-(2R-(tert-butyloxycarbonyl)-amino-4-(methylsulfonyl)butyramido)-bicyclo(2.2.1)heptan-1-yl)methanesulfonyl)-4-(2-methylphenyl)piperazine as a white foam in 90% yield. This product was dissolved in dichloromethane (5 mL) and treated with TFA (4 mL). After 1 h, the solvents were removed under reduced pressure and the residue was dissolved in EtOAc (50 mL), washed with saturated aqueous sodium bicarbonate (4×25 mL), brine (25 mL), dried (MgSO$_4$), filtered, and the solvents were removed under reduced pressure. The residue was purified by silica gel flash column chromatography using a gradient elution of 98:2:0.2 to 95:5:0.5 $CHCl_3$:MeOH:$NH_4OH$. The title compound was obtained as a white foam by evaporation under reduced pressure from ether in 90% yield.

Analysis: $C_{26}H_{42}N_5O_5S_2$, 0.9 $H_2O$, 0.3 ether calc. C 55.07 H 7.95 1N 9.44 found C 55.08 H 7.57 N 9.17

TLC: R$_f$=0.33 (94:6:0.5 CHCl$_3$:MeOH:NH$_4$OH)
HPLC (method A): retention time=8.85 min, purity=99%
FAB MS: m/z=555 (M+H$^+$)

EXAMPLE 107

1-((7,7-Dimethyl-2-endo-(4-(methylsulfonyl)butyramido)-bicyclo(2.2.1)-heptan-1-yl)methanesulfonyl)-4-(2-methylphenyl)piperazine

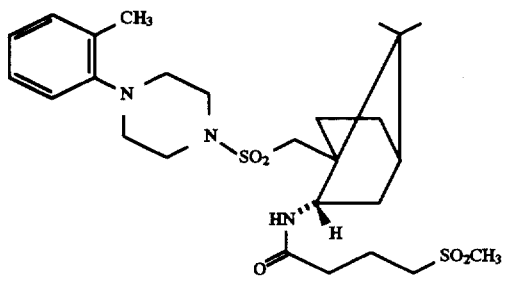

To a stirred solution of 4-(methylsulfonyl)-butyric acid (370 mg; 2.23 mmol), in DMF (25 mL) was added BOP (986 mg; 2.23 mmol), 1-((7,7-dimethyl-2-endo-amino-bicyclo(-2.2.1)heptan-1-yl)methanesulfonyl)-4-(2-methylphenyl)piperazine (960 mg; 2.45 mmol), and DIEA (7.84 mL; 4.5 mmol). After 16 h, the solvent was removed under reduced pressure and the residue was dissolved in EtOAc (100 mL). The organic solution was washed with 5 wt % aqueous citric acid (2×50 mL), saturated aqueous sodium bicarbonate (3×50 mL), and brine. The organic phase was dried (MgSO$_4$), filtered, and the solvent was removed under reduced pressure. The residue was purified by flash silica gel column chromatography using 1:1 ethyl acetate:hexane as eluant. The title compound was obtained as a white foam in 90% yield.

Analysis: C$_{26}$H$_{41}$N$_3$O$_5$S$_2$, 0.25 C$_2$H$_5$CO$_2$CH$_3$, 0.25 H$_2$O calc. C 57.26 H 7.74 N 7.42 found C 57.26 H 7.54 N 7.32

TLC: R$_f$=0.18 (1:1 EtOAc:Hexane)

HPLC (method A): retention time=10.62 min, purity=99.7%

FAB MS: m/z=548 (M+H$^+$)

EXAMPLE 108

1-((7,7-Dimethyl-2-endo-(2S-bis(hydroxyethyl)amino-4-(methylsulfonyl)-butyramido)-bicyclo(2.2.1)heptan-1-yl)methanesulfonyl)-4-(2-methylphenyl)piperazine

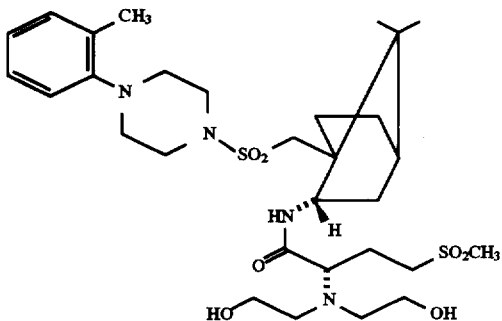

A stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)-piperazine (310 mg, 0.56 mmol) in ethanol (10 mL) was cooled to 0° C. Ethylene oxide was bubbled through the solution, the reaction vessel was sealed, and the reaction mixture was warmed to 70° C. After 48 h, the reaction was cooled to 0° C. and ethylene oxide was bubbled through the solution. The reaction vessel was sealed and heated at 70° C. for 48 h. The solvent was removed under reduced pressure. The residue was purified by preparative reverse phase HPLC using an acetonitrile-water gradient containing 0.1% trifluoroacetic acid. The trifluoroacetate salt of the title compound was obtained by lyophilization to give a white powder in 55% yield.

Analysis: C$_{30}$H$_{50}$N$_4$O$_7$S$_2$, 2.2 CF$_3$CO$_2$H, 0.35 H$_2$O calc. C 45.90 H 5.92 N 6.23 found C 45.90 H 5.89 N 6.33

TLC: R$_f$=0.62 (90:10:0.5 CHCl$_3$:MeOH:NH$_4$OH)

HPLC (method A): retention time=8.93 min, purity=98+%

FAB MS: m/z=643 (M+H$^+$)

EXAMPLE 109

1-((7,7-Dimethyl-2-endo-(2S-(4-tetrahydrothiopyranyl)-amino-4-(methylsulfonyl)butyramido)-bicyclo-(2.2.1)heptan-1-yl)methanesulfonyl)-4-(2-methylphenyl)piperazine

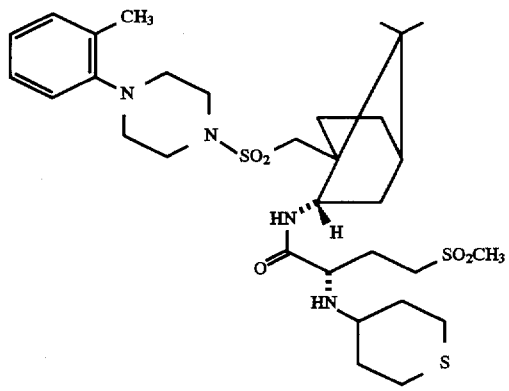

The title compound was prepared from 4-tetrahydrothiopyranone and 1-((7,7-dimethyl-2-endo-(2S-amino-4-(methylsulfonyl)butyramido)-bicyclo-(2.2.1)heptan-1-yl)methanesulfonyl)-4-(2-methylphenyl)piperazine using the procedure set forth in Example 104. The crude product was purified by silica gel flash chromatography eluting with 97:3:0.3 CHCl$_3$:CH$_3$OH:NH$_4$OH. The title compound was obtained as a white foam by evaporation under reduced pressure from chloroform in 95% yield.

Analysis: C$_{31}$H$_{50}$N$_4$O$_5$S$_3$, 0.75 CHCl$_3$ calc. C 51.22 H 6.87 N 7.53 found 51.29 6.83 7.27

TLC: R$_f$=0.44 (95:5:0.5 CHCl$_3$:MeOH:NH$_4$OH)

HPLC (method A): retention time=9.91 min, purity=99%

FAB MS: m/z=655 (M+H$^+$)

EXAMPLE 110

1-((7,7-Dimethyl-2-endo-(2S-(1,1-dioxo-4-tetrahydrothiopyranyl)amino-4-(methylsulfonyl)butyramido)-bicyclo-(2.2.1)heptan-1-yl)methanesulfonyl)-4-(2-methylphenyl)piperazine

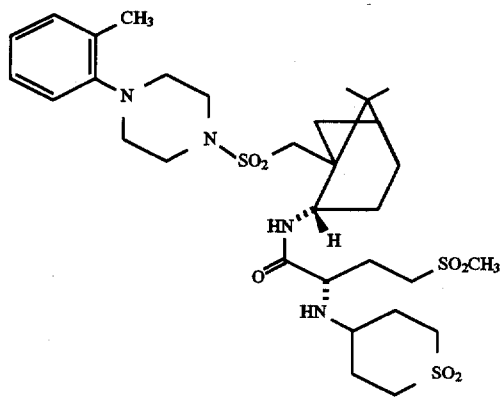

To a stirred solution of 1-((7,7-dimethyl-2-endo-(2S-(4-tetrahydrothiopyranyl)amino-4-(methylsulfonyl)-butyramido)-bicyclo(2.2.1)heptan-1-yl)methanesulfonyl)-4-(2-methylphenyl)piperazine (90 mg, 0.12 mmol) in 1:9 $H_2O$:acetone (3 mL) was added 4-methylmorpholine-N-oxide (43 mg, 0.36 mmol) and $OsO_4$ (0.013 mL of 2.4 wt % solution). After 17 h the reaction was quenched with saturated aqueous $NaHSO_3$ (0.05 mL), and the solvent was removed under reduced pressure. The residue was taken up in methylene chloride (25 mL) and washed with 1N $NaHSO_3$ (3×25 mL), brine (2×25mL), dried over magnesium sulfate, and filtered. The solvent was removed under reduced pressure. The residue was purified by preparative reverse phase HPLC using an acetonitrile-water gradient containing 0.1% trifluoroacetic acid. The trifluoroacetate salt of the title compound was obtained by lyophilization to give a white powder in 80% yield.

Analysis: $C_{31}H_{50}N_4O_7S_3$, 2.05 $CF_3CO2H$, 0.35 $H_2O$ calc.C 45.47 H 5.74 N 6.04 found 45.47 5.72 5.89

TLC: $R_f$=0.33 (95:5:0.5 $CHCl_3$:MeOH:$NH_4OH$)

HPLC (method A): retention time=9.02 min, purity=99%

FAB MS: m/z=687 (M+H$^+$)

EXAMPLE 111

1-((7,7-Dimethyl-2-endo-(2S-acetamido-4-(methylsulfonyl)butyramido)-bicyclo(2.2.1)heptan-1-yl)methane-sulfonyl)-4-(2-methylphenyl)piperazine

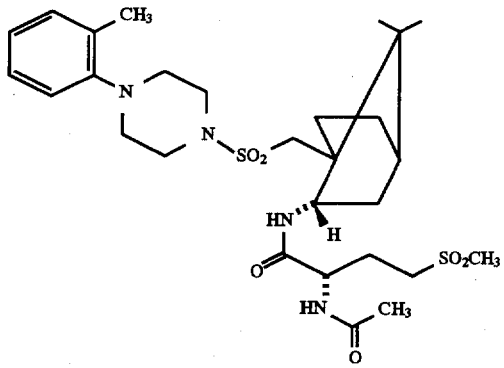

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (160 mg, 0.29 mmol) in chloroform (5 mL) was added acetic anhydride (1 mL), and diisopropylethylamine (0.03 mL). After 2 h the solvent was removed under reduced pressure. The residue was dissolved in chloroform (25 mL) and washed with 5% aqueous HCl (2×10 mL), water (10 mL), saturated aqueous sodium bicarbonate (2×10 mL), brine (10 mL), dried over magnesium sulfate, and filtered. The solvent was removed under reduced pressure to give the title compound as a foam in 90% yield.

Analysis: $C_{28}H_{44}N_4O_6S_2$, 0.5 $CHCl_3$, calc.C 55.89 H 7.37 N 9.30 found 55.90 7.36 9.22

TLC: $R_f$=0.21 (95:5:0.5 $CHCl_3$:MeOH:$NH_4OH$)

HPLC (method A): retention time=9.01 min, purity=99%

FAB MS: m/z=597 (M+H$^+$)

EXAMPLE 112

1-((7,7-Dimethyl-2-endo-(2S-(2-cyanoethyl)amino-4-(methylsulfonyl)butyramido)-bicyclo(2.2.1) heptan-1-yl)methanesulfonyl)-4-(2-methylphenyl) piperazine

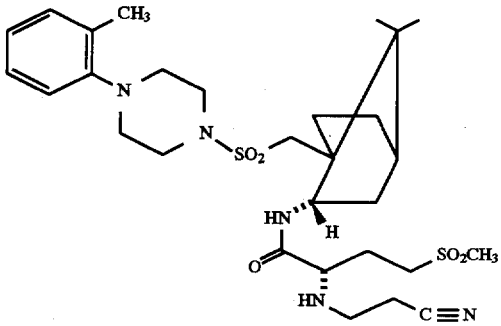

To a stirred solution of 1-((7,7-dimethyl-2-endo-(2S-amino-4-(methylsulfonyl)butyramido)-bicyclo(2.2.1)- heptan-1-yl)methanesulfonyl)-4-(2-methylphenyl) piperazine (200 mg, 0.36 mmol) in MeOH was added acrylonitrile (0.026 mL, 0.40 mmol). After 16 h, an additional amount of acrylonitrile (0.010 mL, 0.15 mmol) was added. After 24 h the solvent was removed under reduced pressure. The residue was purified by silica gel flash column chromatography using 1:3 EtOAc:hexanes as eluant. The solvent was removed under reduced pressure and the residue was triturated in EtOAc and hexanes. The solid was dried in vacuo for 16 h to give the title compound as a white powder in 55% yield.

Analysis: $C_{29}H_{45}N_5O_5S_2$, 0.32 EtOAc calc .C 57.18 H 7.54 N 11.01 found 56.86 7.74 11.01

TLC: $R_f$=0.2 (1:4 EtOAc:hexanes)

HPLC (method A): retention time=8.99 min, purity=99%

FAB MS: m/z=608 (M+H$^+$)

EXAMPLE 113

1-((7,7-Dimethyl-2-endo-(2S-(2-hydroxy-2,2-dimethyl-ethyl)amino-4-(methylsulfonyl)butyramido)-bicyclo(2.2.1)-heptan-1-yl)methanesulfonyl)-4-(2-methylphenyl)piperazine

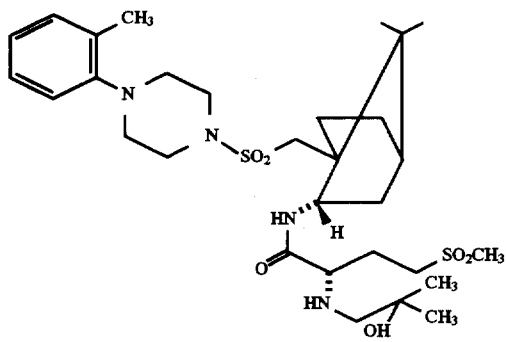

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added isobutylene oxide (0.026 mL, 0.36 mmol) and the reaction was sealed and heated on a steam bath. After 16 h, an additional amount of isobutylene oxide (0.026 mL, 0.36 mmol) was added and heating was continued. After 24 h, an additional amount of isobutylene oxide (0.026 mL, 0.36 mmol) was added and heating was continued. After 24 h the solvent was removed under reduced pressure and the residue was purified by preparative reverse phase HPLC using an acetonitrile-water gradient containing 1% trifluoroacetic acid. The trifluoroacetate salt of the title compound was obtained by lyophilization to yield a white powder in 48% yield.

Analysis: $C_{30}H_{50}N_4O_6S_2$, 1.7 $CF_3CO_2H$, 0.4 $H_2O$ calc.C 48.45 H 6.39 N 6.77 found 48.46 6.37 6.78

TLC: $R_f$=0.3 (95:5:0.5 $CHCl_3$:MeOH:$NH_4OH$)

HPLC (method A): retention time=8.56 min, purity=97%

FAB MS: m/z=627 (M+H$^+$)

EXAMPLE 114

1-((7,7-Dimethyl-2-endo-(2S-(2R-hydroxypropyl) amino-4-(methylsulfonyl)-butyramido)-bicyclo (2.2.1)heptan-1-yl)methanesulfonyl)-4-(2-methylphenyl)piperazine

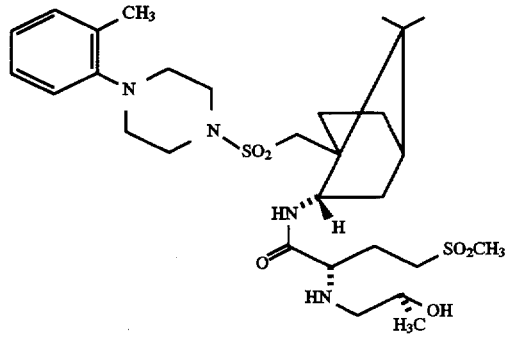

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added R-(+)-propylene oxide (0.025 mL, 0.36 mmol) and the reaction was sealed and heated on a steam bath. After 16 h, an additional amount of R-(+)-propylene oxide (0.010 mL, 0.15 mmol) was added and heating was continued. After 72 h the solvent was removed under reduced pressure and the residue was purified by preparative reverse phase HPLC using an acetonitrile-water gradient containing 1% trifluoroacetic acid. The faster running of two products was isolated and lyophilized to give the trifluoroacetate salt of the title compound as a white powder in 42% yield.

Analysis: $C_{29}H_{48}N_4O_6S_2$, 1.75 $CF_3CO_2H$, 0.5 $H_2O$ calc.C 47.52 H 6.23 N 6.82 found 47.50 6.22 6.90

TLC: $R_f$=0.2 (95:5:0.5 $CHCl_3$:MeOH:$NH_4OH$)

HPLC (method A): retention time=8.34 min, purity=99%

FAB MS: m/z=613 (M+H$^+$)

EXAMPLE 115

1-((7,7-Dimethyl-2-endo-(2S-bis(2R-hydroxypropyl) amino-4-(methylsulfonyl)butyramido)-bicyclo(2.2.1) heptan-1-yl)methanesulfonyl)-4-(2-methylphenyl) piperazine

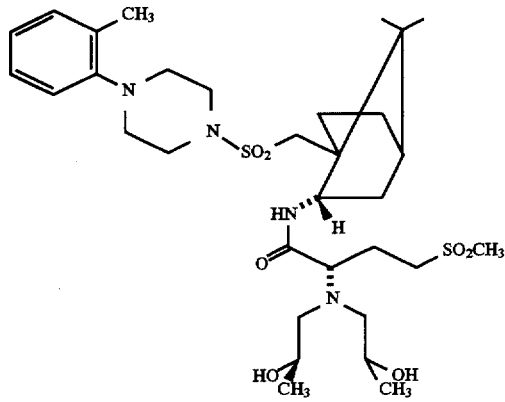

The slower running of two products isolated from the preparative HPLC purification of the crude product from Example 78 was lyophilized to give the trifluoroacetate salt of the title compound as a white powder in 2% yield.

Analysis: $C_{32}H_{54}N_4O_7S_2$, 1.9 $CF_3CO_2H$, 0.15 $H_2O$ calc.C 48.49 H 6.36 N 6.29 found 48.31 6.35 6.52

TLC: $R_f$=0.2 (95:5:0.5 $CHCl_3$:MeOH:$NH_4OH$)

HPLC (method A): retention time=8.74 min, purity=95%

FAB MS: m/z=671 (M+H$^+$)

EXAMPLE 116

1-((7,7-Dimethyl-2-endo-(2S-(2S-hydroxypropyl) amino-4-(methylsulfonyl)butyramido)-bicyclo(2.2.1) heptan-1-yl)methanesulfonyl)-4-(2-methylphenyl) piperazine

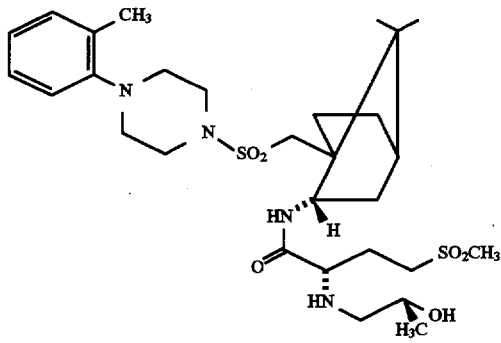

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added S-(−)-propylene oxide (0.025 mL, 0.36 mmol) and the reaction was sealed and heated on a steam bath. After 16 h, an additional amount of S-(−)-propylene oxide (0.010 mL, 0.15 mmol) was added and heating was continued. After 72 h the solvent was removed under reduced pressure. The residue was purified by preparative reverse phase HPLC using an acetonitrile-water gradient containing 1% trifluoroacetic acid. The faster running of two products was isolated and lyophilized to give the trifluoroacetate salt of the title compound as a white powder in 24% yield.

Analysis: $C_{29}H_{48}N_4O_6S_2$, 1.8 $CF_3CO_2H$, 0.3 $H_2O$ calc.C 47.54 H 6.17 N 6.80 found 47.55 6.16 6.90

TLC: $R_f$=0.2 (95:5:0.5 $CHCl_3$:MeOH:$NH_4OH$)

HPLC (method A): retention time=8.40 min, purity=99%

FAB MS: m/z=613 (M+H$^+$)

EXAMPLE 117

1-((7,7-Dimethyl-2-endo-(2S-bis(2S-hydroxypropyl) amino-4-(methylsulfonyl)butyramido)-bicyclo(2.2.1) heptan-1-yl)methanesulfonyl)-4-(2-methylphenyl) piperazine

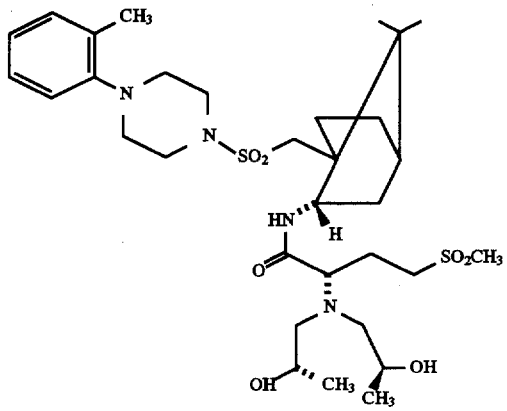

The slower running of two products isolated from the preparative HPLC purification of the crude product from Example 116 was lyophilized to give the trifluoroacetate salt of the title compound as a white powder in 5% yield.

Analysis: $C_{32}H_{54}N_4O_7S_2$, 1.9 $CF_3CO_2H$, 0.15 $H_2O$ calc.C 48.37 H 6.41 N 6.32 found 48.36 6.42 6.52

TLC: $R_f$=0.2 (95:5:0.5 $CHCl_3$:MeOH:$NH_4OH$)

HPLC (method A): retention time=8.78 min, purity=97%

FAB MS: m/z=671 (M+H$^+$)

EXAMPLE 118

1-((7,7-Dimethyl-2-endo-(2S-(2-propyl)amino-4-(methylsulfonyl)butyramido)-bicyclo(2.2.1)heptan-1-yl)methane-sulfonyl)-4-(2-methylphenyl) piperazine

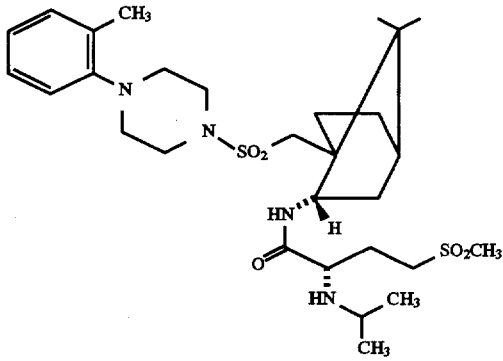

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg, 0.36 mmol) in EtOH (5 mL) was added acetone (0.026 mL, 0.40 mmol) and activated, crushed 3A sieves. After 5 h, $NaBH_3CN$ (11 mg, 0.36 mmol) was added. After 16 h an additional amount of $NaBH_3CN$ (5 mg, 0.15 mmol) was added. After 24 h one drop of water was added and the solvent was removed under reduced pressure. The residue was purified by preparative reverse phase HPLC using an acetonitrile-water gradient containing 1% trifluoroacetic acid. The trifluoroacetate salt of the title compound was obtained by lyophilization to give a white powder in 35% yield.

Analysis: $C_{29}H_{48}N_4O_5S_2$, 1.7 $CF_3CO_2H$, 0.8 $H_2O$ calc. C 48.33 H 6.42 N 6.96 found 48.33 6.42 7.14

TLC: $R_f$=0.6 (95:5:0.5 $CHCl_3$:MeOH:$NH_4OH$)

HPLC (method A): retention time=9.68 min, purity=99%

FAB MS: m/z=597 (M+H$^+$)

EXAMPLE 119

1-((7,7-Dimethyl-2-endo-(2S-(4-pyridyl)amino-4-(methylsulfonyl)butyramido)-bicyclo(2.2.1)heptan-1-yl)methanesulfonyl)-4-(2-methylphenyl)piperazine

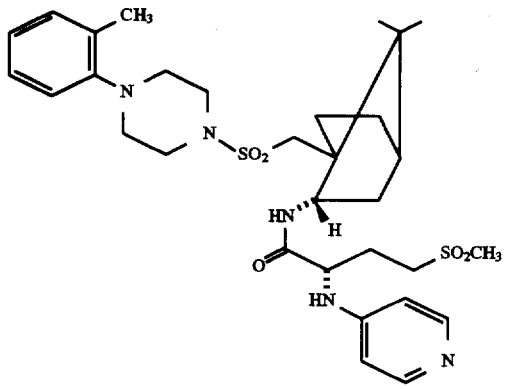

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (200 mg, 0.36 mmol) in DMF (10 mL) was added 4-bromo-pyridine (70 mg, 0.36 mmol) and the reaction was heated to 120° C. for 16 h. Much degradation occurred. The solvent was removed under reduced pressure. The residue was purified by preparative reverse phase HPLC using an acetonitrile-water gradient containing 1% trifluoroacetic acid. The trifluoro-acetate salt of the title compound was obtained by lyophilization to give a white powder in 2.5% yield.

Analysis: $C_{31}H_{45}N_4O_5S_2$, 2.05 $CF_3CO_2H$, 1.35 $H_2O$ calc. C 47.37 H 5.63 N 7.87 found 47.36 5.93 7.48

TLC: $R_f$=0.4 (95:5:0.5 $CHCl_3$:MeOH:$NH_4OH$)

HPLC (method A): retention time=9.23 min, purity=93%

FAB MS: m/z=632 (M+H$^+$)

EXAMPLE 120

1-((7,7-Dimethyl-2-endo-(2S-(2-fluoroethyl)amino-4-(methylsulfonyl)butyramido)-bicyclo(2.2.1)heptan-1-yl)methanesulfonyl)-4-(2-methylphenyl)piperazine

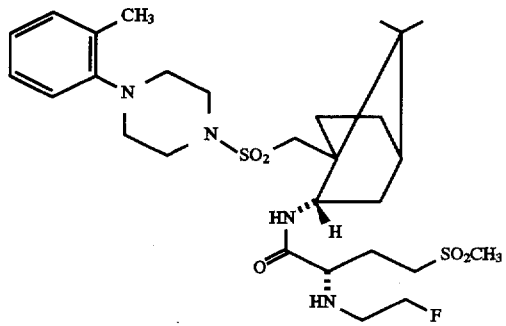

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (200 mg, 0.36 mmol) in DMF (5 mL) was added 1,2-bromo-fluoroethane (0.025 mL, 0.36 mmol) and the reaction was sealed and heated on a steam bath. After 16 h the solvent was removed under reduced pressure. The residue was purified by preparative reverse phase HPLC using an acetonitrile-water gradient containing 1% trifluoroacetic acid. The trifluoroacetate salt of the title compound was obtained by lyophilization to give a white powder in 18% yield.

Analysis: $C_{28}FH_{45}N_4O_5S_2$, 1.8 $CF_3CO_2H$ calc. C 47.08 H 5.85 N 6.95 found 47.09 5.86 7.04

TLC: $R_f$=0.4 (95:5 $CHCl_3$:MeOH)

HPLC (method A): retention time=8.50 min, purity=99%

FAB MS: m/z=601 (M+H$^+$)

EXAMPLE 121

1-((7,7-Dimethyl-2-endo-(2S-ethylamino-4-(methylsulfonyl)butyramido)-bicyclo(2.2.1)heptan-1-yl)methane-sulfonyl)-4-(2-methylphenyl)piperazine

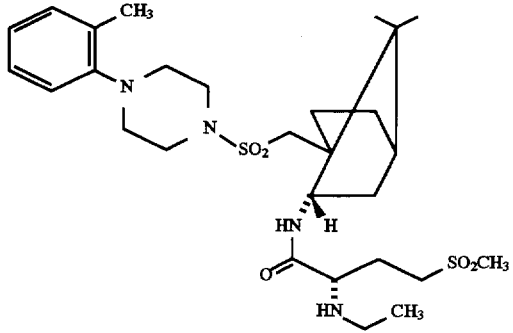

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl)piperazine (0.206 g; 0.371 mmol) in DMF (30 mL) was added iodoethane (0.015 mL; 0.19 mmol) followed by DIEA (0.097 mL, 0.56 mmol). The reaction was stirred at ambient temperature for 48 h. The solvent was removed under reduced pressure and the residue was dissolved in EtOAc (50 mL) and washed with saturated aqueous sodium bicarbonate (3×50 mL). The organic phase was dried (MgSO$_4$), filtered, and the solvent was removed under reduced pressure. The residue was purified by silica gel flash column chromatography, eluting with 98:2:0.2 CH$_2$Cl$_2$:MeOH:NH$_4$OH. The resulting oil was dissolved in CH$_3$CN and H$_2$O containing 0.1% TFA and lyophylized to give the trifluoroacetate salt of the title compound as a white powder in 40% yield.

Analysis: C$_{28}$H$_{46}$N$_4$O$_5$S$_2$ 0.15 H$_2$O, 0.85 TFA FW=682.451 calc. C 52.57 H 6.96 N 8.21 found C 52.30 H 6.92 N 8.19

TLC: R$_f$=0.46 (96:4:0.4 CH$_2$Cl$_2$:MeOH:NH$_4$OH)

HPLC (method A): retention time=8.43 min, 99% purity

FAB MS: m/z=583 (M+H$^+$)

EXAMPLE 122

1-((7,7-Dimethyl-2-endo-(2S-(tert-butyloxycarbonyl)-methylamino-4-(methylsulfonyl)butyramido)-bicyclo-(2.2.1)heptan-1-yl)methanesulfonyl)-4-(2-methylphenyl)-piperazine

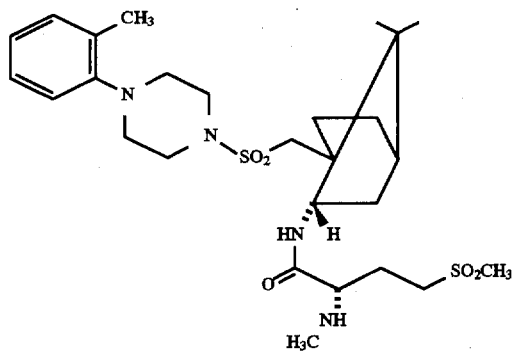

A solution of N-Boc-N-methyl-L-methionine sulfone (0.899 g; 3.04 mmol) and BOP (1.35 g, 3.00 mmol) in DMF (50 mL) was stirred for 10 min. A solution of 1-((7,7-dimethyl-2-endo-amino-bicyclo(2.2.1)heptan-1-yl)methane-sulfonyl)-4-(2-methylphenyl)piperazine (1.80 g; 2.77 mmol) in DMF (15 mL) was added dropwise to the reaction followed by DIEA (5.2 mL; 3.0 mmol) to bring the reaction mixture to pH 8 (as judged by spotting an aliquot on wetted E. Merck pH paper). After 16 h the DMF was removed under reduced pressure and the residue was dissolved in EtOAc (100 mL) and washed with 5 wt % aqueous citric acid (100mL) and saturated aqueous sodium bicarbonate (2×100 mL). The organic layer was dried (MgSO$_4$), filtered, and the solvent was removed under reduced pressure. The residue was purified by silica gel flash column chromatography eluting with 40:60 hexane:EtOAc. The title compound was obtained as a white foam in 90% yield.

Analysis: C$_{32}$H$_{52}$N$_4$O$_7$S$_2$ 0.25 EtOAc FW=690.95 calc. C 57.36 H 7.88 N 8.11 found C 57.68 H 7.84 N 8.13

TLC: R$_f$=0.27 (40:60 hexane:EtOAc)

HPLC (method A): retention time=11.21 min, 99+% purity

FAB MS: m/z=669 (M+H$^+$)

EXAMPLE 123

1-((7,7-Dimethyl-2-endo-(2S-methylamino-4-(methylsulfonyl)butyramido)-bicyclo(2.2.1)heptan-1-yl)methane-sulfonyl)-4-(2-methylphenyl)piperazine

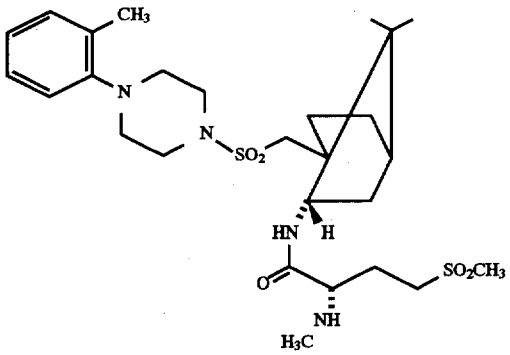

To a stirred solution of 1-((7,7-dimethyl-2-endo-(2S-(tert-butyloxycarbonyl)methylamino-4-(methylsulf-onyl)butyramido)-bicyclo(2.2.1)heptan-1-yl)methane-sulfonyl)-4-(2-methylphenyl)piperazine (1.0 g; 1.5 mmol) in DCM (25 mL) was added TFA (25 mL). The reaction was stirred at ambient temperature for 1 h. The solvents were removed under reduced pressure and the residue was dissolved in EtOAc (100 mL) and washed with saturated aqueous sodium bicarbonate (4×50 mL). The organic layer was dried (MgSO$_4$), filtered, and the solvent was removed under reduced pressure to give the title compound as a foam in 95% yield.

Analysis: C$_{27}$H$_{44}$N$_4$O$_5$S$_2$ 0.40 EtOAc 0.45 H$_2$O FW=612.15 calc. C 56.11 H 7.92 N 9.15 found C 56.14 H 7.78 N 9.16

TLC: R$_f$=0.16 (97:3 DCM:MeOH)

HPLC (method A): retention time=8.23 min, 99+% purity

FAB MS: m/z=569 (M+H$^+$)

EXAMPLE 124

1-((7,7-Dimethyl-2-endo-(2S-trideuteromethylamino-4-(methylsulfonyl)butyramido)-bicyclo(2.2.1)heptan-1-yl)methanesulfonyl)-4-(2-methylphenyl)piperazine

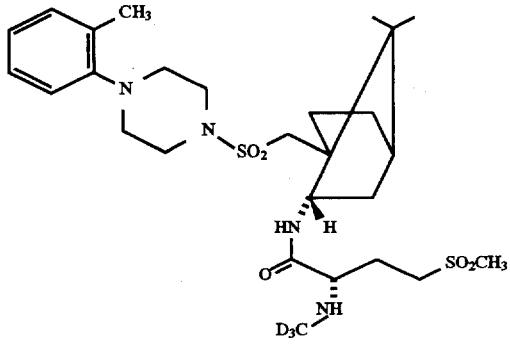

The title compound was prepared from N-Boc-N-trideuteromethyl-L-methionine sulfone and 1-((7,7-dimethyl-2-endo-amino-bicyclo(2.2.1)heptan-1-yl)methane-sulfonyl)-4-(2-methylphenyl)piperazine using the procedures set forth in Examples 122 and 123. The title compound was obtained as a white foam by evaporation under reduced pressure from EtOAc-hexane.

Analysis: $C_{27}D_3H_{41}N_4O_5S_2$ 0.35 EtOAc, 0.20 $H_2O$ FW=606.22 calc. C 56.26 H 7.28 N 9.24 found C 55.93 H 7.67 N 9.18

TLC: $R_f$=0.16 (97:3 DCM:MeOH)

HPLC (method A): retention time=8.23 min, 99+% purity

FAB MS: m/z=572 (M+H$^+$)

EXAMPLE 125

1-((7,7-Dimethyl-2-endo-(2S-bis(trideuteromethyl) amino-4-yl)methylsulfonyl)butyramido)-bicyclo (2.2.1)heptan -1-yl)methanesulfonyl)-4-(2-methylphenyl)piperazine

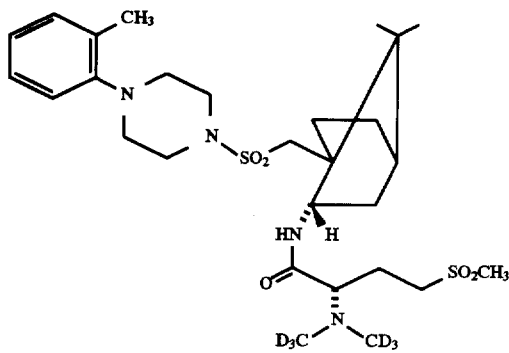

A stirred solution of 1-((7,7-dimethyl-2-endo-(2S-amino-4-(methylsulfonyl)butyramido)-bicyclo(2.2.1)-heptan-1-yl) methanesulfonyl)-4-(2-methylphenyl)piperazine (0.433 g, 0.781 mmol) and DIEA (0.203 mL; 1.17 mmol) in DMF (10 mL) was cooled to 0° C. Iodomethane-d$_3$ (0.50 mL, 0.786 mmol) was added dropwise via syringe. The reaction was gradually warmed to ambient temperature and then stirred for 16 h. The reaction was cooled to 0° C. and an additional 0.5 eq of CD$_3$I and DIEA were added, and the reaction was stirred for 16 h. at ambient temperature. The solvent was removed under reduced pressure and the residue was dissolved in EtOAc (50 mL). The EtOAc solution was washed with saturated aqueous sodium bicarbonate (2×25 mL), dried (MgSO$_4$), filtered, and the solvent was removed under reduced pressure. HPLC analysis of the crude product indicated the presence of unreacted mono-, bis-, and tris-alkylated products. The desired bis-alkylated product was isolated by silica gel flash column chromatography eluting with 98:2 CH$_2$Cl$_2$:MeOH. Pure fractions were combined and the solvent was removed under reduced pressure to give an oil. The oil was lyophilized from 1:2 CH$_3$CN:H$_2$O containing 0.1% TFA to give the trifluoroacetate salt of the title compound as a white powder.

Analysis: $C_{28}D_6H_{40}N_4O_5S_2$ 0.80 TFA, 2.45 $H_2O$ FW=724.256 calc. C 49.08 H 6.36 N 7.74 found C 49.12 H 6.55 N 7.43

TLC: $R_f$=0.43 (95:5:0.5 DCM:MeOH:NH$_4$OH)

HPLC (method A): retention time=8.33 min, 99+% purity

FAB MS: m/z=589 (M+H$^+$)

EXAMPLE 126

1-((7,7-Dimethyl-2-endo-(2S-tris(trideuteromethyl) amino-4-(methylsulfonyl)butyramido)-bicyclo(2.2.1) heptan-1-yl)methanesulfonyl)-4-(2-methylphenyl) piperazine trifluoroacetate

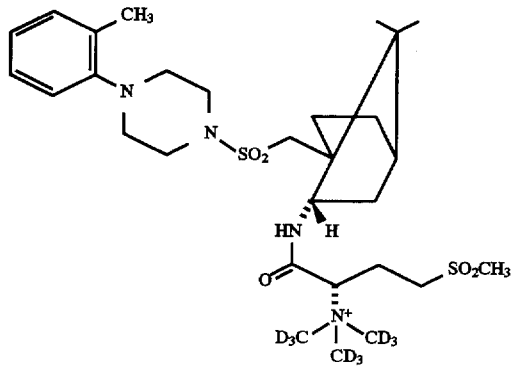

A stirred solution of 1-((7,7-dimethyl-2-endo-(2S-amino-4-(methylsulfonyl)butyramido)-bicyclo(2.2.1)-heptan-1-yl) methanesulfonyl)-4-(2-methylphenyl)piperazine (0.426 g, 0.768 mmol) and DIEA (0.40 mL; 2.3 mmol) in DMF (20 mL) was cooled to 0° C. Iodomethane-d$_3$ (0.16 mL; 2.5 mmol) was added dropwise via syringe. The reaction was gradually warmed to ambient temperature and stirred for 48 h. The solvent was removed under reduced pressure and the residue was purified by preparative reverse-phase HPLC using a water:acetonitrile gradient containing 0.1% TFA. The title compound was obtained by lyophilization to give a white powder in 50% yield.

Analysis: $C_{31}H_4D_9F_{30}N_4O_7S_2$ 0.6 TFA FW=788.284 calc. C 49.06 H 6.34 N 7.11 found C 49.13 H 6.61 N 6.96

TLC: $R_f$=0.11 (90:10:0.5 DCM:MeOH:NH$_4$OH)

HPLC (method A): retention time=8.51 min, 99+% purity

FAB MS: m/z=606 (M$^+$)

EXAMPLE 127

1-((7,7-Dimethyl-2-endo-(2S-N,N-dimethylformamidinyl-4-(methylsulfonyl) butyramido)-bicyclo(2.2.1)heptan-1-yl) methanesulfonyl)-4-(2-methylphenyl)piperazine

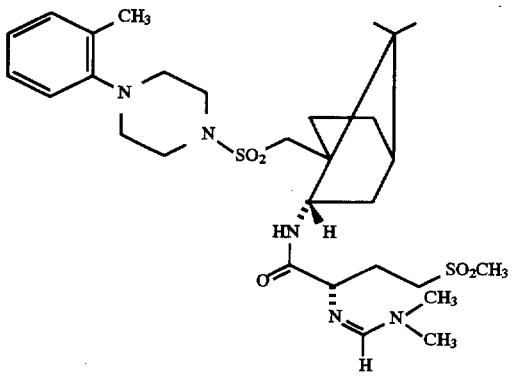

To a stirred solution of 1-((7,7-dimethyl-2-endo-(2S-amino-4-(methylsulfonyl)butyramido)-bicyclo(2.2.1)-heptan-1-yl)methanesulfonyl)- 4-(2-methylphenyl)

piperazine (100 mg; 0.18 mmol) in DMF (2 mL) was added dimethyl-formamide-dimethylacetal (xx mL; 0.54 mmol). After 24 h, the solvent was removed under reduced pressure. The resulting oil was dissolved in EtOAc (50 mL) and washed with water (2×25 mL). The organic phase was dried (MgSO$_4$), filtered, and the solvent was removed under reduced pressure. The title compound was obtained as a white foam by evaporation under reduced pressure from chloroform in 90% yield.

Analysis: C$_{29}$H$_{47}$N$_5$O$_5$S$_2$ 0.4 CHCl$_3$ calc. C 53.70 H 7.27 N 10.65 found C 53.87 H 7.27 N 10.66

TLC: R$_f$=0.35 (95:5:0.5 DCM:MeOH:NH$_4$OH)

HPLC (method A): retention time=8.34 min, 99+% purity

FAB MS: m/z=610 (M+H$^+$)

EXAMPLE 128

1-((7,7-Dimethyl-2-endo-(2S-acetamidinyl-4-(methylsulfonyl)butyramido)-bicyclo(2.2.1)heptan-1-yl)methane-sulfonyl)-4-(2-methylphenyl) piperazine

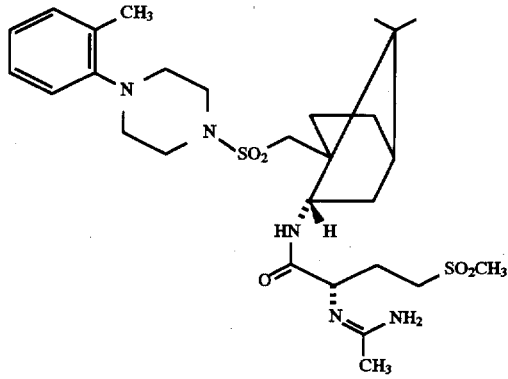

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (100 mg; 0.18 mmol) in DMF (4 mL) was added methyl acetimidate hydrochloride (100 mg; 0.91 mmol) and sodium carbonate (150 mg; 1.5 mmol). After 48 h, the mixture was filtered through Celite and the solvent was removed under reduced pressure. The resulting dark oil was purified by silica gel flash column chromatography using a gradient elution of 95:5:0.5 CHCl$_3$:MeOH:NH$_4$OH to 85:15:0.75 CHCl$_3$:MeOH:NH$_4$OH. The trifluoroacetate salt of the title compound was obtained as a white powder in 25% yield by lyophilization from 1:3 CH$_3$CN:H$_2$O containing 0.1% TFA.

Analysis: C$_{28}$H$_{45}$N$_5$O$_5$S$_2$ 1.0 TFA, 1.5 H$_2$O calc. C 48.90 H 6.70 N 9.50 found C 48.71 H 6.45 N 9.62

TLC: R$_f$=0.29 (85:15:0.75 CHCl$_3$:MeOH:NH$_4$OH)

HPLC (method A): retention time=9.05 min, 97.9% purity

FAB MS: m/z=596 (M+H$^+$)

EXAMPLE 129

1-((7,7-Dimethyl-2-endo-(2S-(4-(1-tert-butyloxycarbony)piperidinyl)amino-4-(methylsulfonyl)butyramido)-bicyclo(2.2.1)heptan-1-yl)methanesulfonyl)-4-(2-methylphenyl)-piperazine

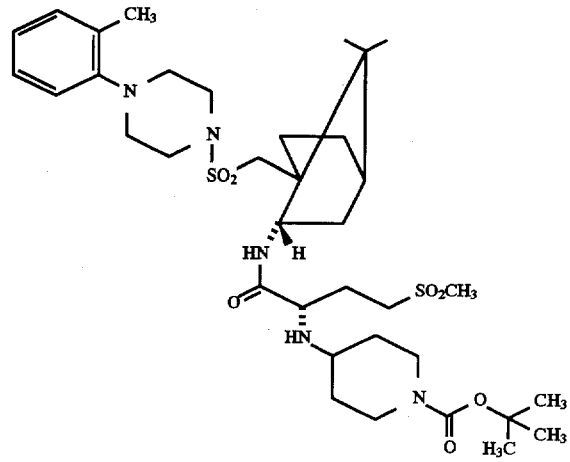

To a stirred solution of 1-((7,7-dimethyl-2-endo-(2S-amino-4-(methylsulfonyl)butyramido)-bicyclo(2.2.1)-heptan-1-yl)methanesulfonyl)-4-(2-methylphenyl) piperazine (200 mg; 0.36 mmol) in methanol containing 1% by volume of acetic acid (4 mL) was added 4–5 molecular sieves (3 Å), 1-tert-butyloxycarbonyl-4-piperidinone (78 mg, 0.39 mmol) and sodium cyanoborohydride (20 mg; 0.36 mmol). After 5 h, the reaction was quenched with aqueous sodium bicarbonate (0.5 mL) and the solvent was removed under reduced pressure. The residue was taken up in ethyl acetate (50 mL) and washed with saturated aqueous sodium bicarbonate (2×50 mL), brine (2×50 mL), dried over magnesium sulfate, and filtered. The solvent was removed under reduced pressure. The residue was purified by silica gel flash column chromatography using 95:5 CHCl$_3$:MeOH as eluant. The resulting oil was lyophilized from H$_2$O:CH$_3$CN containing 0.1% TFA. The trifluoroacetate salt of the title compound was obtained in 85% yield as a white powder.

Analysis: C$_{36}$H$_{59}$N$_5$O$_7$S$_2$, 0.45 H$_2$O, 2.5 TFA calc. C 47.75 H 6.10 N 6.79 found 47.76 6.07 7.12

TLC: R$_f$=0.27 (95:5 CHCl$_3$:MeOH)

HPLC (method A): retention time=0.72 min, purity=99+%

FAB MS: m/z=738 (M+H$^+$)

EXAMPLE 130

1-((7,7-Dimethyl-2-endo-(2S-(4-piperidinyl)amino-4-(methylsulfonyl)butyramido)-bicyclo(2.2.1)heptan-1-yl)methanesulfonyl)-4-(2-methylphenyl)piperazine

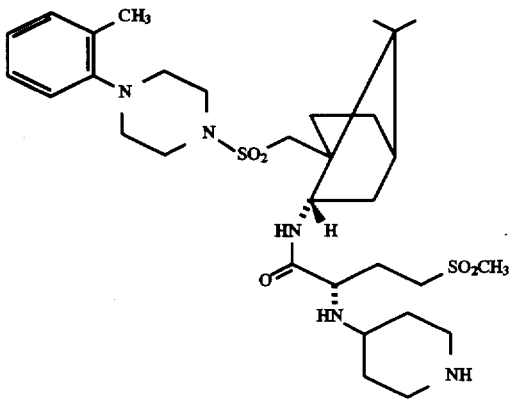

To a stirred solution of 1-((7,7-dimethyl-2-endo-(2S-(4-(1-tert-butyloxycarbony)piperidinyl)amino-4-(methylsulfonyl)butyramido)-bicyclo(2.2.1)heptan-1-yl)methanesulfonyl)-4-(2-methylphenyl)piperazine (0.10 g; 0.14 mmol) in dichloromethane (20 mL) was added TFA (15 mL). After 1 h, the solvents were removed under reduced pressure and the residue was dissolved in EtOAc (50 mL) and washed with saturated aqueous sodium bicarbonate (4×25 mL), brine (25 mL), dried (MgSO₄) and filtered. The solvent was removed under reduced pressure and the residue was purified by silica gel flash column chromatography using 90:10:1 CHCl₃:MeOH:NH₄OH as eluant. The title compound was obtained as a white foam in 90% yield by evaporation under reduced pressure from dichloromethane.

Analysis: $C_{31}H_{51}N_5O_5S_2$, 0.6 $CH_2Cl_2$ calc. C 55.13 H 7.70 N 9.79 found 55.09 7.64 10.07

TLC: $R_f$=0.11 (90:10:1 CHCl₃:MeOH:NH₄OH)

HPLC (method A): retention time=8.13 min, purity= 99+%

FAB MS: m/z=638 (M+H+)

EXAMPLE 131

1-((7,7-Dimethyl-2-Endo-(2S-Amino-4-Hydroxybutyramido)-Bicyclo(2.2.1)Heptan-1-yl)Methanesulfonyl)-4-(2-Methylphenyl)Piperazine

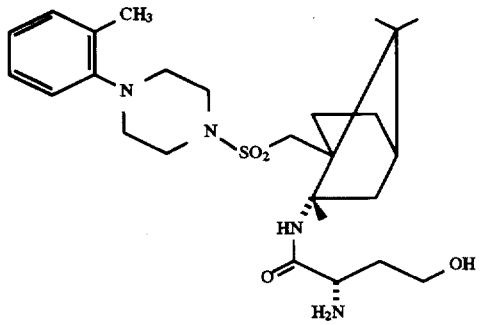

To a stirred solution of 1-((7,7-dimethyl-2-endo-amino-bicyclo(2.2.1)heptan-1-yl)methanesulfonyl)-4-(2-methylphenyl)piperazine (2.0 g; 5.1 mmol) in DMF (20 mL) was added N-Boc-L-homoserine, O-benzyl ether (1.73 g; 5.61 mmol), hydroxybenzotriazole hydrate (0.87 g; 5.7 mmol), DIEA (2.0 mL; 11.5 mmol), and EDC (1.09 g; 5.7 mmol). After 24 h, the solvent was removed under reduced pressure and the residue was dissolved in EtOAc (100 mL) and washed with 5% aqueous citric acid (2×25 mL), water (25 mL), saturated aqueous sodium bicarbonate (2×50 mL), dried (MgSO₄) and filtered. The solvent was removed under reduced pressure and the residue was purified by silica gel flash column chromatography using 1:1 ethyl acetate:hexane as eluant. 1-((7,7-Dimethyl-2-endo-(2S-tert-butyloxycarbonylamino-4-(benzyloxy)butyramido)-bicyclo(2.2.1)heptan-1-yl)methanesulfonyl)-4-(2-methylphenyl)piperazine was obtained as a white foam in 90% yield. This compound was N-deprotected by dissolving in dichloromethane (15 mL) and adding TFA (10 mL). After 1 h, the solvents were removed under reduced pressure and the residue was dissolved in ethyl acetate (100 mL) and washed with saturated aqueous sodium bicarbonate (4×50 mL), dried (MgSO₄), and filtered. The solvent was removed under reduced pressure to give ((7,7-dimethyl-2-endo-(2S-amino-4-(benzyloxy)butyramido)-bicyclo(2.2.1)heptan-1-yl)methanesulfonyl)-4-(2-methylphenyl)piperazine as a white foam in 95% yield. This compound was O-deprotected by dissolving in methanol containing 5% by volume of acetic acid (50 mL) and stirring with palladium black (150 mg) under an atmosphere of hydrogen (ambient pressure). After 24 h, the reaction was flushed with argon, the catalyst was removed by filtration through Celite, and the solvents were removed under reduced pressure. The residue was purified by silica gel flash column chromatography using 90:10:1 CHCl₃:MeOH:NH₄OH as eluant. The title compound was obtained as a white foam in 90% yield after evaporation under reduced pressure from chloroform-ether.

Analysis: $C_{25}H_{40}N_4O_4S$, 0.15 CHCl₃, 0.15 ether calc. C 59.28 H 8.05 N 10.74 found 59.42 8.02 10.72

TLC: $R_f$=0.18 (90:10:1 CHCl₃:MeOH :NH₄OH)

HPLC (method A): retention time=8.31 min, purity= 99+%

FAB MS: m/z=493 (M+H+)

EXAMPLE 132

1-((7,7-Dimethyl-2-Endo-(2S-(4-Piperidinyl)Amino-4-Hydroxybutyramido)-Bicyclo(2.2.1)Heptan-1-Yl) Methanesulfonyl)-4-(2-Methylphenyl)Piperazine

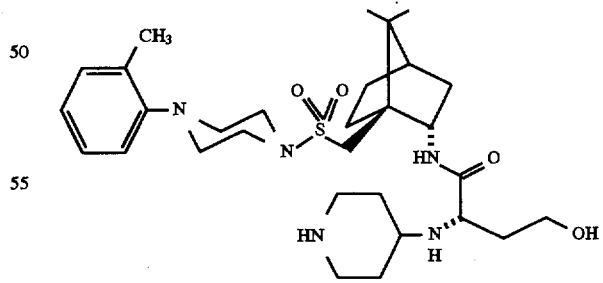

The title compound was prepared by reductive alkylation of 1-((7,7-dimethyl-2-endo-(2S-amino-4-hydroxybutyramido)-bicyclo(2.2.1)heptan-1-yl)methanesulfonyl)-4-(2-methylphenyl)piperazine with 1-tert-butyloxycarbonyl-4-piperidinone followed by TFA N-deprotection using procedures analogous to those set forth in Example 93 and Example 94. The crude product was purified by preparative reverse phase HPLC using a water-acetonitrile gradient containing 0.1% by volume of TFA. The trifluoroacetate of the title compound was obtained as a white lyophilized powder in 50% yield.

Analysis: $C_{30}H_{49}N_5O_4S$, 3.9 TFA, 1.15 $H_2O$ calc. C 43.60 H 5.34 N 6.73 found 43.61 4.95 7.12

TLC: $R_f$=0.10 (90:10:1 $CHCl_3$:MeOH:$NH_4OH$)

HPLC (method A): retention time=7.85 min, purity=99+%

FAB MS: m/z=576 (M+H+)

EXAMPLE 133

1-((7,7-Dimethyl-2-Endo-(2S-(4-Tetrahydropyranyl)-Amino-4-Hydroxybutyramido)-Bicyclo(2.2.1)Heptan-1-yl)Methanesulfonyl)-4-(2-Methylphenyl)Piperazine

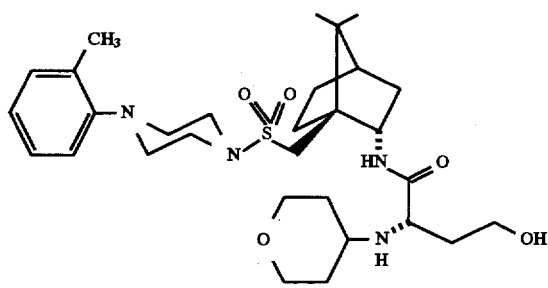

The title compound was prepared by reductive alkylation of 1-((7,7-dimethyl-2-endo-(2S-amino-4-hydroxybutyramido)-bicyclo(2.2.1)heptan-1-yl)methanesulfonyl)-4-(2-methylphenyl)piperazine with 4-tetrahydropyranone using a procedure analogous that set forth in Example 68. The crude product was purified by silica gel flash column chromatography using 95:5:0.5 chloroform:methanol:$NH_4OH$ as eluant. The title compound was obtained as a white foam by evaporation under reduced pressure from chloroform-methanol.

Analysis: $C_{30}H_{48}N_4O_5S$, 0.2 $CHCl_3$, 0.3 $CH_3OH$ calc. C 60.02 H 8.16 N 9.18 found 60.04 8.09 9.14

TLC: $R_f$=0.35 (95:5:0.5 $CHCl_3$:MeOH:$NH_4OH$)

HPLC (method A): retention time=8.82 min, purity=96%

FAB MS: m/z=577 (M+H+)

EXAMPLE 134

1-((7,7-Dimethyl-2-Endo-(2S-(1,1-Dioxo-4-Tetrahydrothiopyranyl)Amino-4-Hydroxybutyramido)-Bicyclo( 2.2.1)Heptan-1-yl)Methanesulfonyl)-4-(2-Methylphenyl)Piperazine

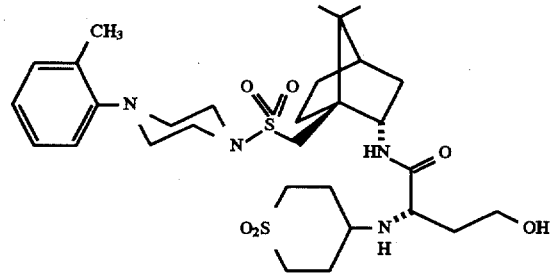

The title compound was prepared by reductive alkylation of 1-((7,7-dimethyl-2-endo-(2S-amino-4-hydroxybutyramido)-bicyclo(2.2.1)heptan-1-yl)methanesulfonyl)-4-(2-methylphenyl)piperazine with 4-tetrahydrothiopyranone followed by oxidation to the sulfone using procedures analogous those set forth in Example 73 and Example 74. The crude product was purified by silica gel flash column chromatography using 95:5:0.5 chloroform:methanol:$NH_4OH$ as eluant. The title compound was obtained as a white foam by evaporation under reduced pressure from chloroform.

Analysis: $C_{30}H_{48}N_4O_6S_2$, 0.4 $CHCl_3$, 0.1 $H_2O$ calc. C 54.13 H 7.26 N 8.31 found 54.15 6.91 8.15

TLC: $R_f$=0.30 (95:5:0.5 $CHCl_3$:MeOH:$NH_4OH$)

HPLC (method A): retention time=8.79 min, purity=97%

FAB MS: m/z=625 (M+H+)

EXAMPLE 135

1-((7,7-dimethyl-2-endo-(2S-amino-3-hydroxypropionamido)-bicyclo(2.2.1)heptan-1-yl)methanesulfonyl)-4-(2-methylphenyl)piperazine

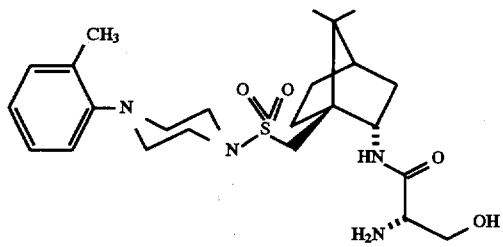

The title compound was prepared from 1-((7,7-dimethyl-2-endo-amino-bicyclo(2.2.1)heptan-1-yl)methanesulfonyl)-4-(2-methylphenyl)piperazine and Boc-L-serine followed by TFA N-deprotection using procedures analogous to those set forth in Example 35 and Example 36. The crude product was purified by silica gel flash column chromatography using 95:5:0.5 $CHCl_3$:MeOH:$NH_4OH$ as eluant. The title compound was obtained as a white foam in 90% yield after evaporation under reduced pressure from chloroform.

Analysis: $C_{24}H_{38}N_4O_4S$, 0.35 $CHCl_3$ calc. C 56.19 H 7.43 N 10.77 found 56.24 7.50 10.86

TLC: $R_f$=0.32 (95:5:0.5 $CHCl_3$:MeOH:$NH_4OH$)

HPLC (method A): retention time=8.23 min, purity=99+%

FAB MS: m/z=479 (M+H+)

EXAMPLE 136

1-((7,7-dimethyl-2-endo-(2S-(4-piperidinyl)amino-
3-hydroxypropionamido)-bicyclo(2.2.1)heptan-1-yl)
methanesulfonyl)-4-(2-methylphenyl)piperazine

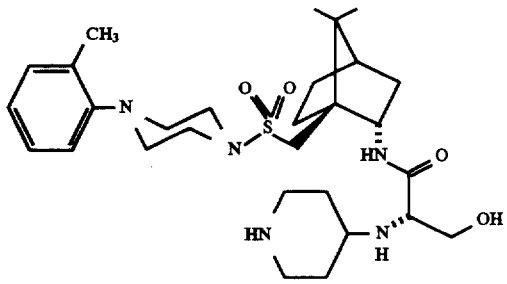

The title compound was prepared by reductive alkylation of 1-((7,7-dimethyl-2-endo-(2S-amino-3-hydroxypropionamido)-bicyclo(2.2.1)heptan-1-yl)methanesulfonyl)-4-(2-methylphenyl)piperazine with 1-tert-butyloxycarbonyl-4-piperidinone followed by TFA N-deprotection using procedures analogous to those set forth in Example 93 and Example 94. The crude product was purified by preparative reverse phase HPLC using a water-acetonitrile gradient containing 0.1% by volume of TFA. The trifluoroacetate of the title compound was obtained as a white lyophilized powder in 80% yield.

Analysis: $C_{29}H_{47}N_5O_4S$, 4 TFA, 0.9 $CH_3CN$ calc. C 44.20 H 5.14 N 7.89 found 44.63 4.62 7.88

TLC: $R_f$=0.05 (90:10:1 $CHCl_3$:MeOH:$NH_4OH$)

HPLC (method A): retention time=7.99 min, purity=99+%

FAB MS: m/z=562 (M+H$^+$)

EXAMPLE 137

1-((7,7-dimethyl-2-endo-(2S-(4-tetrahydropyranyl)
amino-3-hydroxypropionamido)-bicyclo(2.2.1)
heptan-1-yl)methanesulfonyl)-4-(2-methylphenyl)
piperazine

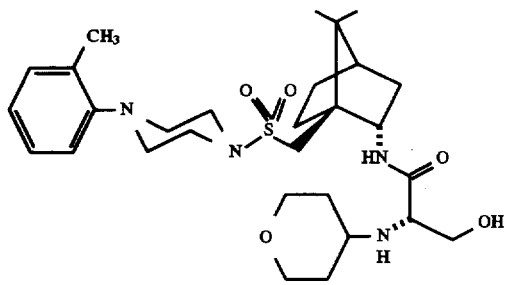

The title compound was prepared by reductive alkylation of 1-((7,7-dimethyl-2-endo-(2S-amino-3-hydroxypropionamido)-bicyclo(2.2.1)heptan-1-yl)methanesulfonyl)-4-(2-methylphenyl)piperazine with 4-tetrahydropyranone using a procedure analogous that set forth in Example 68. The crude product was purified by silica gel flash column chromatography using 95:5:0.5 chloroform:methanol:$NH_4OH$ as eluant. The title compound was obtained as a white foam by evaporation under reduced pressure from ethyl acetate in 90% yield.

Analysis: $C_{29}H_{46}N_4O_5S$, 0.45 ethyl acetate calc. C 61.40 H 8.30 N 9.30 found 61.03 8.13 9.54

TLC: $R_f$=0.30 (95:5:0.5 $CHCl_3$:MeOH:$NH_4OH$)

HPLC (method A): retention time=8.76 min, purity=98%

FAB MS: m/z=563 (M+H$^+$)

EXAMPLE 138

1-((7,7-dimethyl-2-endo-(2S-(1,1-dioxo-4-
tetrahydrothiopyranyl)amino-3-
hydroxypropionamido)-bicyclo(2.2.1)heptan-1-yl)
methanesulfonyl)-4-(2-methylphenyl)piperazine

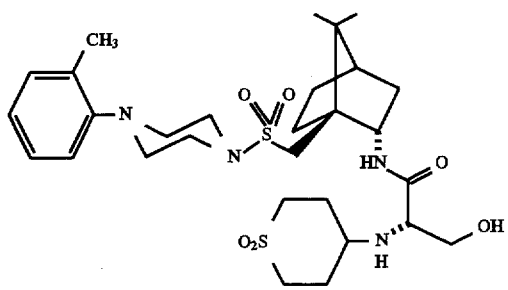

The title compound was prepared by reductive alkylation of 1-((7,7-dimethyl-2-endo-(2S-amino-3-hydroxypropionamido)-bicyclo(2.2.1)heptan-1-yl)methanesulfonyl)-4-(2-methylphenyl)piperazine with 4-tetrahydrothiopyranone followed by oxidation to the sulfone using procedures analogous those set forth in Example 109 and Example 110. The crude product was purified by silica gel flash column chromatography using 95:5:0.5 chloroform:methanol:$NH_4OH$ as eluant. The title compound was obtained as a white foam by evaporation under reduced pressure from chloroform.

Analysis: $C_{29}H_{46}N_4O_6S_2$, 1.25 $H_2O$ calc. C 54.99 H 7.72 N 8.85 found 55.01 7.99 8.76

TLC: $R_f$=0.35 (95:5:0.5 $CHCl_3$:MeOH:$NH_4OH$)

HPLC (method A): retention time=8.88 min, purity=99%

FAB MS: m/z=611 (M+H$^+$)

EXAMPLE 139

1-((7,7-dimethyl-2-endo-(2S-amino-3r-
hydroxybutyramido)-bicyclo(2.2.1)heptan-1-yl)
methanesulfonyl)-4-(2-methylphenyl)piperazine

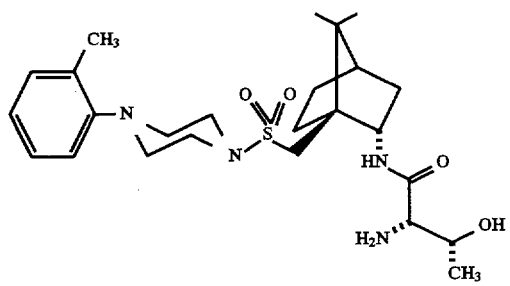

The title compound was prepared from 1-((7,7-dimethyl-2-endo-amino-bicyclo(2.2.1)heptan-1-yl)methanesulfonyl)-4-(2-methylphenyl)piperazine and Boc-L-threonine followed by TFA N-deprotection using procedures analogous to those set forth in Example 71 and Example 72. The crude product was purified by silica gel flash column chromatography using 95:5:0.5 $CHCl_3$:MeOH:$NH_4OH$ as eluant. The trifluoroacetate salt of the title compound was obtained as a white powder by lyophilization from H₂O:CH₃CN containing 0.1% by volume of TFA.

Analysis: $C_{25}H_{40}N_4O_4S$, 1.75 TFA, 0.1 H₂O calc. C 49.32 H 6.09 N 8.07 found 49.35 6.01 7.93

TLC: $R_f$=0.15 (95:5:0.5 CHCl₃:MeOH:NH₄OH)

HPLC (method A): retention time=8.51 min, purity= 99+%

FAB MS: m/z=493 (M+H⁺)

EXAMPLE 140

1-((7,7-dimethyl-2-endo-(2S-(4-piperidinyl)amino-3S-hydroxybutyramido)-bicyclo(2.2.1)heptan-1-yl)methanesulfonyl)-4-(2-methylphenyl)piperazine

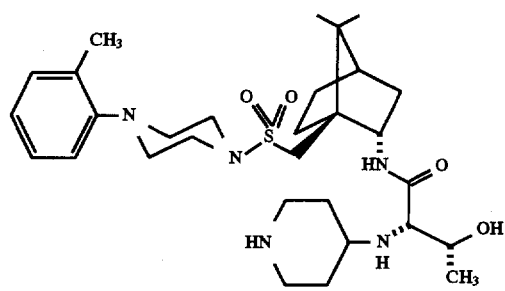

The title compound was prepared by reductive alkylation of 1-((7,7-dimethyl-2-endo-(2S-amino-3S-hydroxybutyramido)-bicyclo(2.2.1)heptan-1-yl)methanesulfonyl)-4-(2-methylphenyl)piperazine with 1-tert-butyloxycarbonyl-4-piperidinone followed by TFA N-deprotection using procedures analogous to those set forth in Example 129 and Example 140. The crude product was purified by preparative reverse phase HPLC using a water-acetonitrile gradient containing 0.1% by volume of TFA. The trifluoroacetate of the title compound was obtained as a white lyophilized powder in 80% yield.

Analysis: $C_{30}H_{49}N_5O_4S$, 2.5 TFA, 0.2 H₂O calc. C 46.87 H 6.24 N 7.81 found 46.88 6.01 8.00

TLC: $R_f$=0.09 (90:10:1 CHCl₃:MeOH:NH₄OH)

HPLC (method A): retention time=8.10 min, purity= 99+%

FAB MS: m/z=576 (M+H⁺)

EXAMPLE 141

1-((7,7-dimethyl-2-endo-(2S-(4-tetrahydropyranyl)amino-3S-hydroxybutyramido)-bicyclo(2.2.1)heptan-1-yl)methanesulfonyl)-4-(2-methylphenyl)piperazine

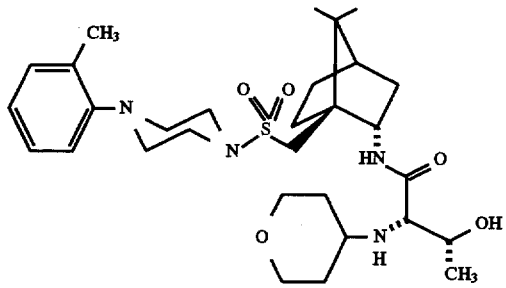

The title compound was prepared by reductive alkylation of 1-((7,7-dimethyl-2-endo-(2S-amino-3S-hydroxybutyramido)-bicyclo(2.2.1)heptan-1-yl)methanesulfonyl)-4-(2-methylphenyl)piperazine with 4-tetrahydropyranone using a procedure analogous that set forth in Example 104. The crude product was purified by silica gel flash column chromatography using 95:5:0.5 chloroform:methanol:NH₄OH as eluant. The title compound was obtained as a white foam by evaporation under reduced pressure from chloroform in 90% yield.

Analysis: $C_{30}H_{48}N_4O_5S$, 0.35 CHCl₃ calc. C 58.92 H 7.88 N 9.06 found 59.07 7.87 9.13

TLC: $R_f$=0.44 (95:5:0.5 CHCl₃:MeOH:NH₄OH)

HPLC (method A): retention time=8.96 min, purity=99%

FAB MS: m/z=577 (M+H⁺)

EXAMPLE 142

1-((7,7-dimethyl-2-endo-(2S-(4-ethoxycarbonyl)cyclohexylamino-4-(methylsulfonyl)butyramido)-bicyclo(2.2.1)heptan-1-yl)methanesulfonyl)-4-(2-methylphenyl)piperazine

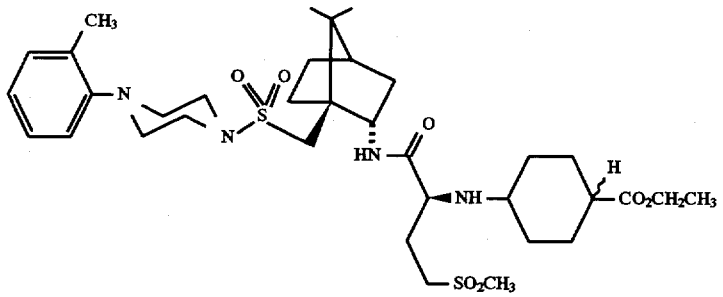

The title compound was prepared by reductive alkylation of 1-((7,7-dimethyl-2-endo-(2S-amino-4-(methylsulfonyl)butyramido)-bicyclo(2.2.1)heptan-1-yl)methanesulfonyl)-4-(2-methylphenyl)piperazine with 4-ethoxycarbonylcyclohexanone using a procedure analogous that set forth in Example 68. The crude product was purified by silica gel flash column chromatography using 2:1 ethyl acetate:hexane as eluant. Two isomers of the title compound differing in configuration at the point of attachment of the ethoxycarbonyl substituent were obtained as a white foams.

Isomer Number 1

Analysis: $C_{35}H_{56}N_4O_7S_2$, 1.55 CH₃OH calc. C 57.86 H 8.26 N 7.39 found 57.85 7.95 7.62

TLC: $R_f$=0.13 (2:1 ethyl acetate:hexane)

HPLC (method A): retention time=10.24 min, purity= 99%

FAB MS: m/z=709 (M+H⁺)

Isomer Number 2

Analysis: $C_{35}H_{56}N_4O_7S_2$, 0.2 ethyl acetate, 0.9 $CH_2Cl_2$
calc. C 54.89 H 7.46 N 6.98 found 54.95 7.51 7.00

TLC: $R_f$=0.26 (2:1 ethyl acetate:hexane)

HPLC (method A): retention time=10.27 min, purity=99%

FAB MS: m/z=709 (M+H⁺)

EXAMPLE 143

1-((7,7-dimethyl-2-endo-(2S-(4-carboxy)
cyclohexylamino-4-(methylsulfonyl)butyramido)-
bicyclo(2.2.1)heptan-1-yl)methanesulfonyl)-4-(2-
methylphenyl)piperazine

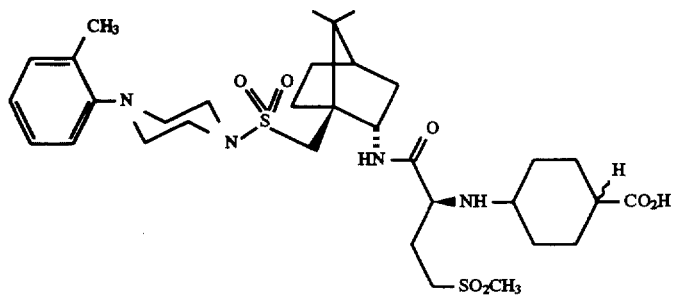

The title compound was prepared by saponification of the lower Rf isomer from Example 106. 1-((7,7-Dimethyl-2-endo-(2S-(4-ethoxycarbonyl)cyclohexylamino-4-(methylsulfonyl)butyramido)-bicyclo(2.2.1)heptan-1-yl)methanesulfonyl)-4-(2-methylphenyl)piperazine (50 mg; 0.071 mmol) was dissolved in THF (2 mL) containing 2N NaOH (1 mL). After the reaction had been stirred at ambient temperature for 2 days, aqueous citric acid was added to obtain a pH 3 solution and the product was extracted into ethyl acetate. The solvent was removed under reduced pressure to give the title compound as a foam.

Analysis: $C_{33}H_{52}N_4O_7S_2$, 0.55 ethyl acetate, 0.85 $CH_2Cl_2$
calc. C 54.01 H 7.31 N 6.99 found 54.12 7.18 6.99

TLC: $R_f$=0.42 (90:10:0.5 $CHCl_3$:MeOH:HOAc)

HPLC (method A): retention time=9.06 min, purity=99%

FAB MS: m/z=781 (M+H⁺)

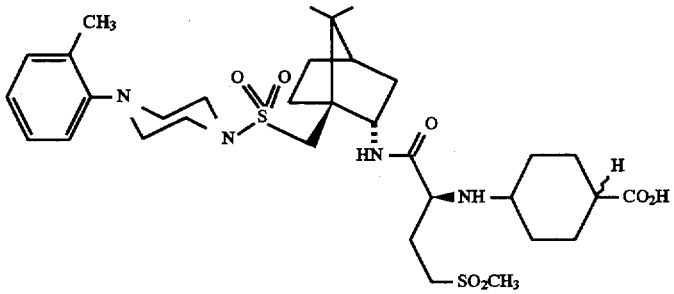

EXAMPLE 144

1-((7,7-dimethyl-4-(methylsulfonyl)-butyramido)-
bicyclo(2.2.1)heptan-1-yl)methanesulfonyl)-4-(2-
methylphenyl)piperazine The title compound was prepared by saponification of the higher Rf isomer from Example 106. 1-((7,7-Dimethyl-2-endo-(2S-(4-ethoxycarbonyl)cyclohexylamino-4-(methylsulfonyl)butyramido)-bicyclo(2.2.1)heptan-1-yl) methanesulfonyl)-4-(2-methylphenyl)piperazine (50 mg; 0.071 mmol) was dissolved in THF (2 mL) containing 2N NaOH (1 mL). After the reaction had been stirred at ambient temperature for 2 days, aqueous citric acid was added to obtain a pH 3 solution and the product was extracted into ethyl acetate. The solvent was removed under reduced pressure to give the title compound as a foam.

Analysis: $C_{33}H_{52}N_4O_7S_2$, 0.65 ethyl acetate, 0.95 $CHCl_3$ calc. C 53.60 H 7.27 N 6.84 found 53.64 7.15 6.85

TLC: $R_f$=0.44 (90:10:0.5 $CHCl_3$:MeOH:HOAc)

HPLC (method A): retention time=9.39 min, purity=99%

FAB MS: m/z=781 (M+H$^+$)

TABLE

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

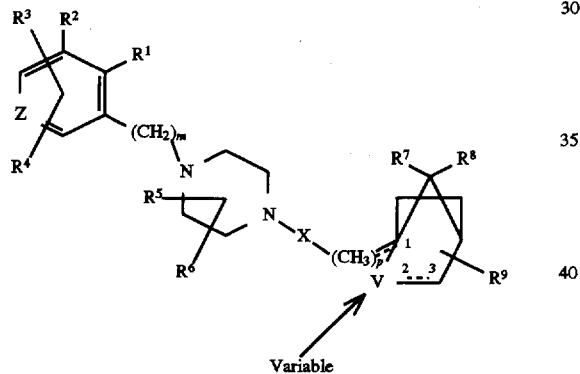

In this generic structure, all values for V are for a substituted carbon atom which is to be understood to be in the 2 position of the camphor ring; therefore, in the following table, said substituted carbon atom generally only shows two valence bonds, the other two valence bonds being understood to be part of the camphor ring. When said substituted carbon atom only shows one valence bond, it is to be understood that a double bond is present between the 2 and 3 positions of the camphor ring.

TABLE OF SUBSTITUENTS REPRESENTED BY "V"

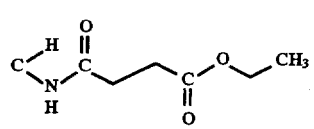

TABLE OF SUBSTITUENTS REPRESENTED BY "V" -continued

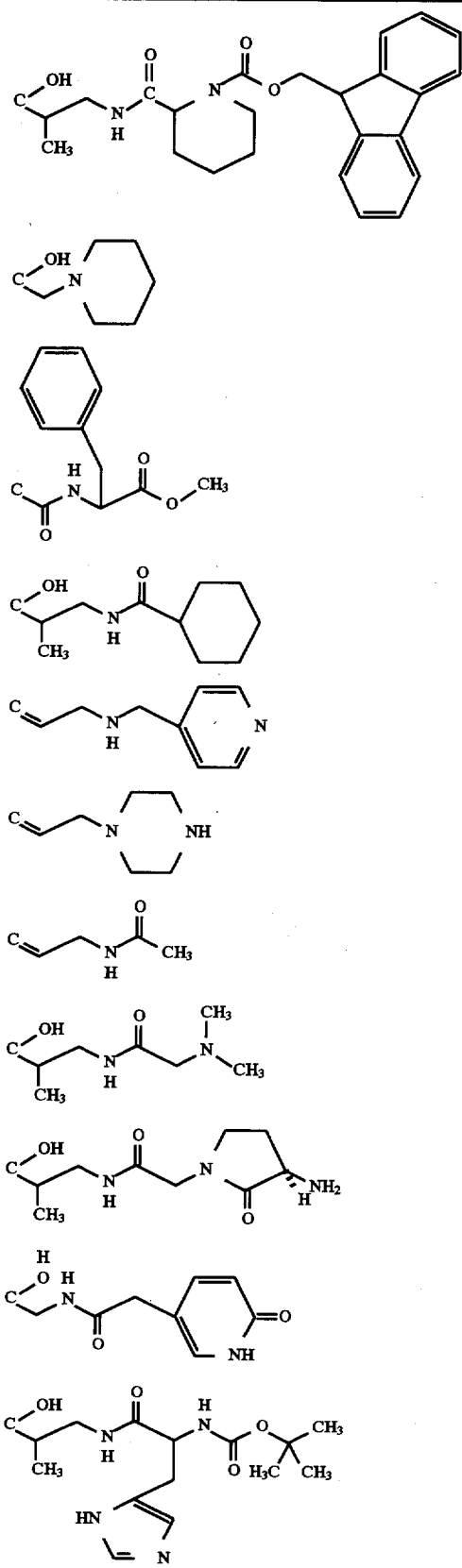

TABLE OF SUBSTITUENTS REPRESENTED BY "V"
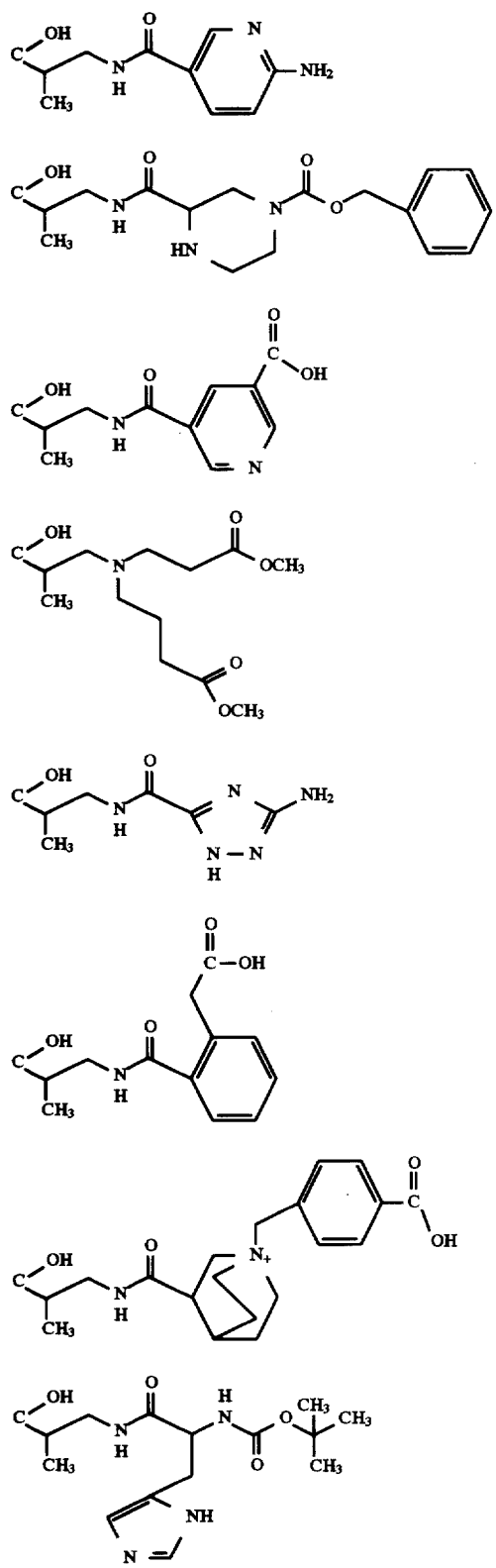
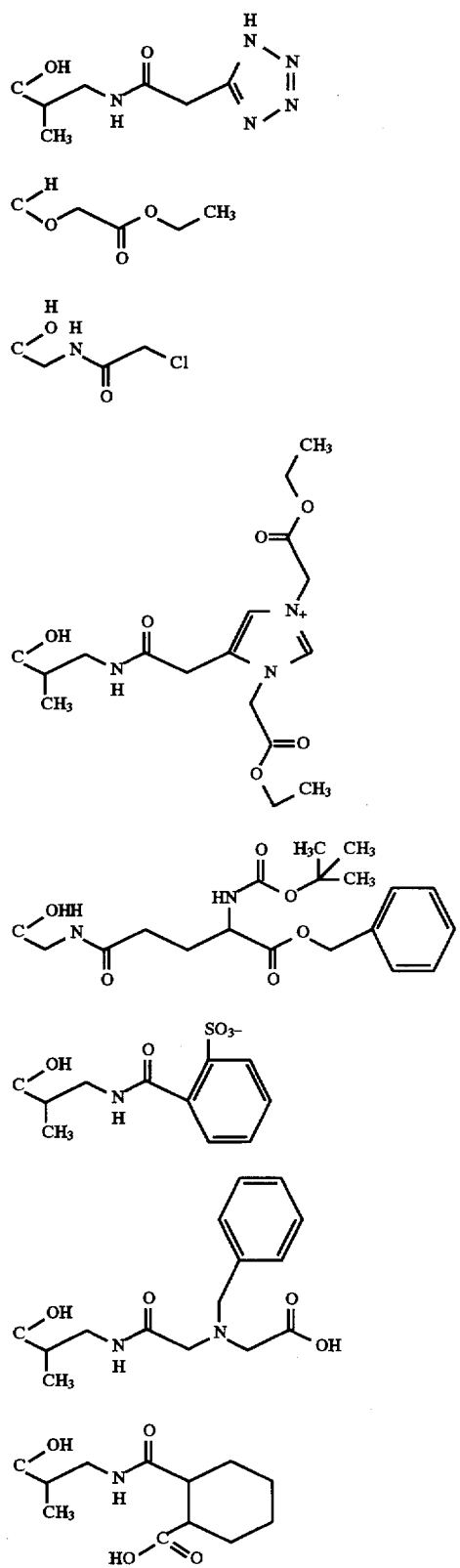

121
-continued
TABLE OF SUBSTITUENTS REPRESENTED BY "V"
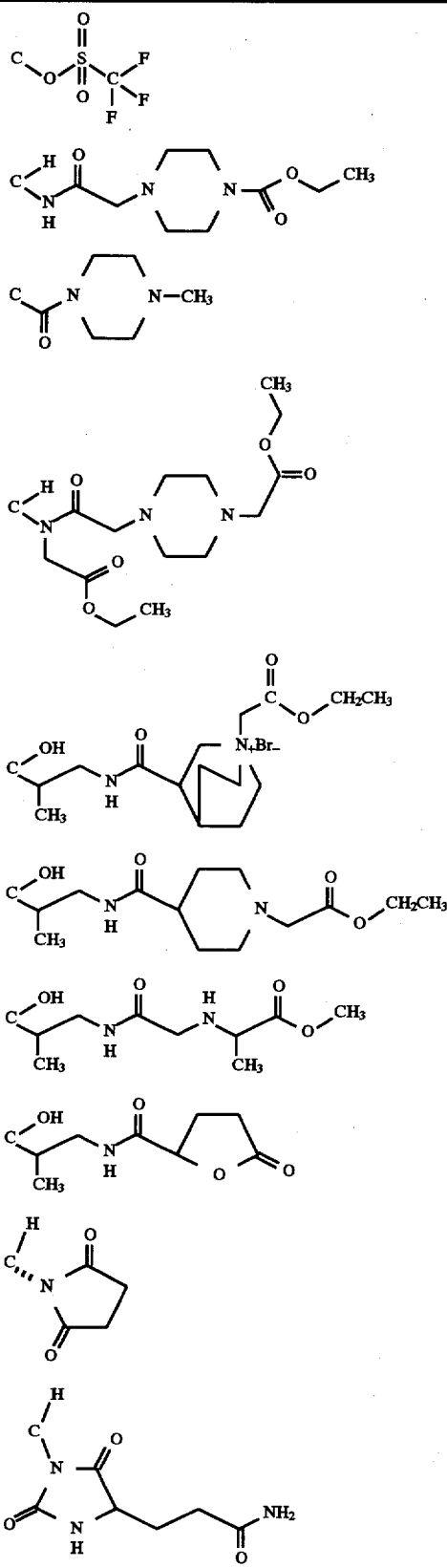
122
-continued
TABLE OF SUBSTITUENTS REPRESENTED BY "V"
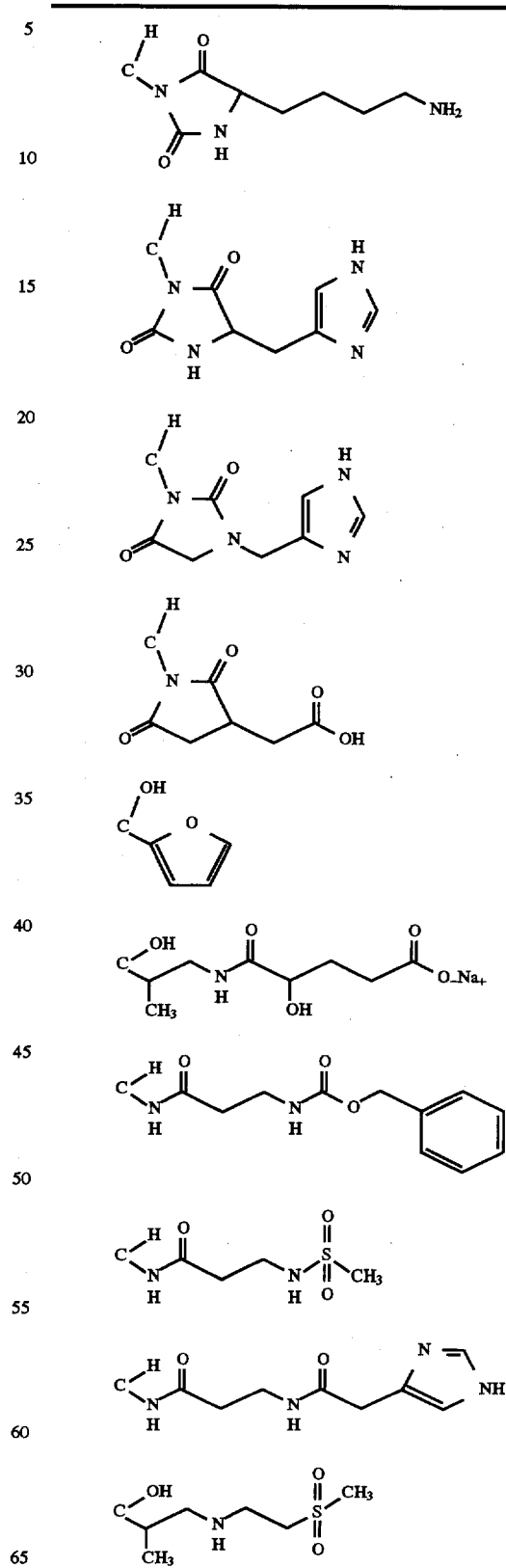

TABLE OF SUBSTITUENTS REPRESENTED BY "V"

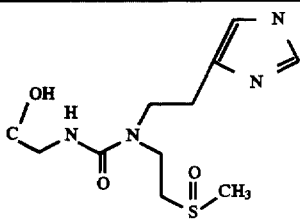

Additional examples of species covered by this invention include the following non-limiting list:

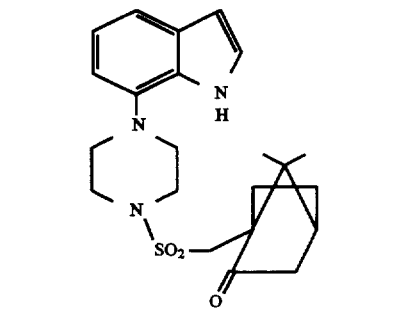

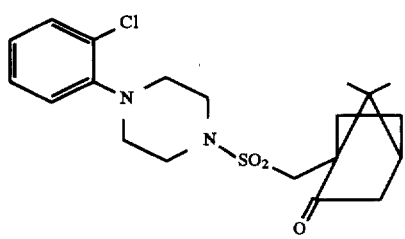

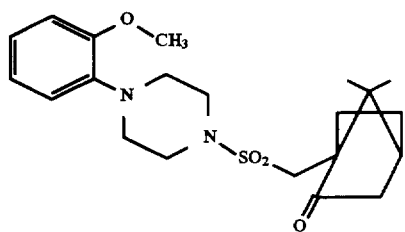

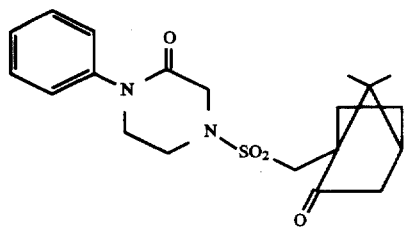

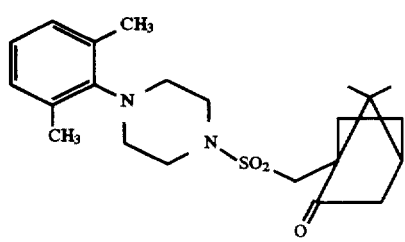

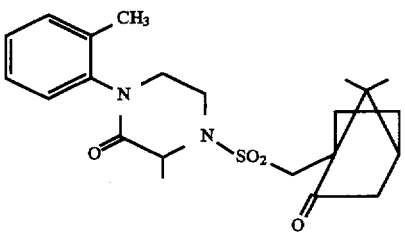

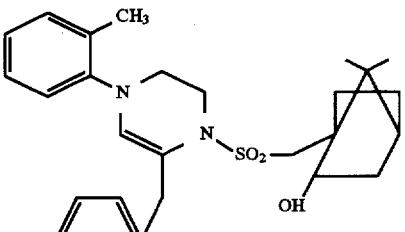

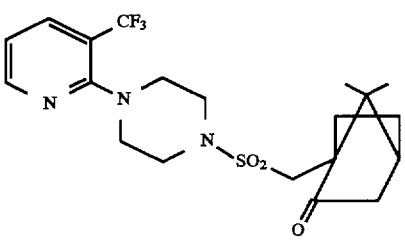

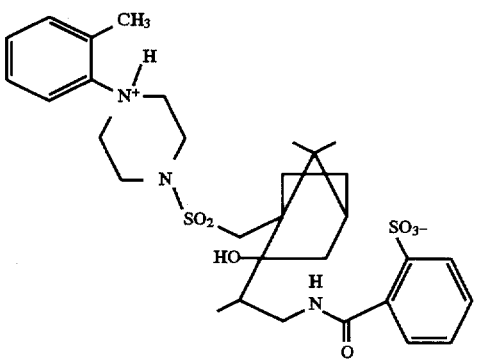

EXAMPLE 145

RADIOGLIGAND BINDING ASSAYS

The high affinity binding of [$^3$H] Oxytocin (OT)([tyrosyl, 3,5-[$^3$H]OT; 30–60 Ci/mmol; New England Nuclear. Boston, Mass.) to uterine OT receptors was based on an assay (Fuchs, A-R; Fuchs, F; Soloff, MS. 1985 J. Clin. Endocrinol. Metab. 60:37) using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 mM unlabeled OT and the binding reaction was terminated by filtration through glass fiber filters using a cell harvester (model 7019, Skatron, Inc., Sterling, Va.). IC$_{50}$ (the concentration of tested compound that inhibits 50% of OT) was reported, unless otherwise noted.

The measurement of [$^3$H]Vasopressin (AVP) ([phenylalanyl-3,4,5-$^3$H]AVP; 80–90 Ci/mmol; New England Nuclear)binding to a crude membrane preparation of male rat liver (AVP-$V_1$ sites) or kidney medulla (AVP-$V_2$ sites) was determined according to the method of Butlen, et al. (Butlen, D; Guillon, G; Rajerison, R. M.;Jard, S; Sawyer, W. H.;Manning, M. 1978 Mol Pharmacol 14:1006).

Competition assays were conducted at equilibrium (30 minutes at 30° C.) using 1 nM [$^3$H]AVP (liver) or 2 nM [3H]AVP (kidney) in the following assay buffer: 100 mM Tris-HCl, 5 mM $MgCl_2$, 0.1% BSA, 50 mM phenylmethylsulfonylfluoride, and 50 mg/ml bacitracin, pH 8.0. Nonspecific binding (5–10% of the total binding) was determined using 10 mM unlabeled AVP, and the binding reaction was terminated by filtration as described above for the [$^3$H]OT binding assay.

$K_i$ values were obtained for each compound from three to six separate determinations of the $IC_{50}$ values ($K_i=IC_{50}/1+c/K_d$) (Cheng, Y-C; Prusoff, W. H.; 1973 Biochem Pharmacol 22:3099) using $K_d$ values obtained from a saturation binding assay: [$^3$H]OT (uterus), 0.7 nM; [$^3$H]AVP (liver), 0.4 nM; [$^3$H] (kidney), 1.4 nM.

| Example | $IC_{50}$ |
| --- | --- |
| 1 | 145; 155 nM |
| 2 | 800 nM |
| 3 | 150 nM |
| 4 | 53% inhib. at 1000 nM |
| 5 | 27% inhib. at 1000 nM |
| 6 | 82 nM |
| 7 | 830; 16000 nM |
| 8 | 4.3 |
| 9 | 6.5 nM |
| 10 | 75% inhib. at 1000 nM |
| 11 | 1100 nM |
| 12 | 15.3 nM |
| 13 | 33.3 nM |
| 14 | 55 nM |
| 15 | 60 nM |
| 16 | 27 nM |
| 17 | 16 nM |
| 18 | 120 nM |
| 19 | 160 nM |
| 20 | 3.6 nM |
| 37 | 1,000 nM |
| 38 | 150 nM |
| 39 | 180 nM |
| 40 | 34 nM |
| 41 | 100 nM |
| 42 | 10 nM |
| 43 | 8 nM |
| 44 | 18 nM |
| 45 | 5 nM |
| 46 | 48% inhibition at 100 nM |
| 47 | 54 nM |
| 48 | 23% inhibition at 100 nM |
| 49 | 1,100 nM |
| 50 | 44% inhibition at 1,000 nM |
| 51 | 64% inhibition at 1,000 nM |
| 52 | 36% inhibition at 100 nM |
| 53 | 75% inhibition at 1,000 nM |
| 54 | 31% inhibition at 1,000 nM |
| 55 | 72% inhibition at 1,000 nM |
| 56 | 38% inhibition at 1,000 nM |
| 57 | 78% inhibition at 1,000 nM |
| 58 | 120 nM |
| 59 | 260 nM |
| 60 | 34% inhibition at 100 nM |
| 61 | 35 nM |
| 62 | 37% inhibition at 100 nM |
| 63 | 35% inhibition at 100 nM |
| 64 | 78% inhibition at 1,000 nM |
| 65 | 16% inhibition at 10,000 nM |
| 66 | 5% inhibition at 10,000 nM |
| 67 | 37% inhibition at 1,000 nM |
| 68 | 460 nM |
| 69 | — |
| 70 | 91% inhibition at 100 nM |
| 71 | 7.7 nM |
| 72 | 1.2 nM |
| 73 | 5.4 nM |
| 74 | 54% inhibition at 1,000 nM |
| 75 | 35% inhibition at 1,000 nM |
| 76 | 6.3 nM |
| 77 | 9.2 nM |
| 78 | 110 nM |
| 79 | 26 nM |
| 80 | 12 nM |
| 81 | 20 nM |
| 82 | 15 nM |
| 83 | 30 nM |
| 84 | 25 nM |
| 85 | 66% inhibition at 100 nM |
| 86 | 38 nM |
| 87 | 66% inhibition at 110 nM |
| 88 | 28 nM |
| 89 | 14 nM |
| 90 | 30 nM |
| 91 | 54 nM |
| 92 | 66% inhibition at 100 nM |
| 94 | 56 nM |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of formula:

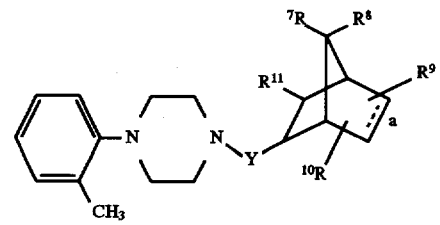

wherein
a is a single or double bond;
Y is —C=O;
$R^7$ and $R^8$ are independently alkyl;
$R^9$ and $R^{10}$ are independently hydrogen or methyl;
$R^{11}$ is
—NH—CO—$R^{13}$ or
$R^{13}$ is
(1) hydrogen, (2) alkoxy, (3) unsubstituted or substituted pyrrolidinyl, wherein the substituent is alkoxycarbonylalkyl; or (4) unsubstituted or substituted alkyl, wherein the substituent is one or more of hydroxyl, alkylsulfonyl, imidazolyl, or unsubstituted or substituted amino, wherein the substituent is one or more of tetrahydropyranyl or alkoxycarbonyl.

2. The compound of claim 1 selected from the group consisting of

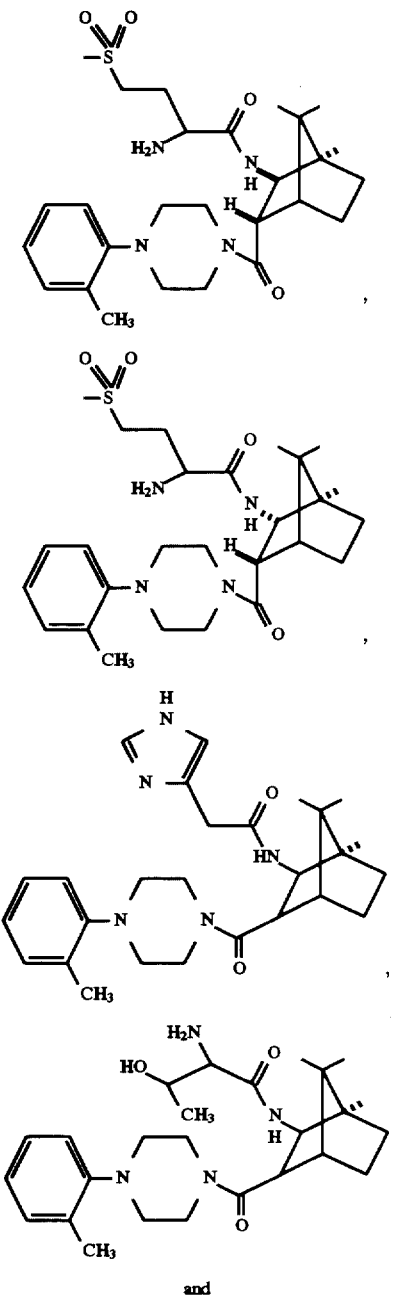

and

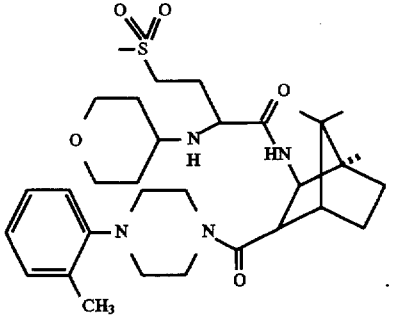

3. A pharmaceutical composition comprising a pharmaceutically acceptable carrier and the compound as claimed in claim 1.

4. A method of antagonizing the binding of oxytocin to its receptor binding site in a mammalian biologic system, comprising the step of introducing a pharmacologically effective amount of the compound of claim 1 into said mammalian biologic system.

5. A method of preventing preterm labor in a mammal in need thereof, comprising the step of administering to said mammal a pharmacologically effective amount of the compound of claim 1.

6. A method of stopping labor prior to cesarian delivery in a mammal in need thereof, comprising the step of administering to said mammal a pharmacologically effective amount of the compound of claim 1.

7. A method of treating dysmenorrhea in a mammal in need thereof, comprising the step of administering to said mammal a pharmacologically effective amount of the compound of claim 1.

8. A method of antagonizing vasopressin from binding to its receptor site in a mammal, comprising the step of administering to said mammal a pharmacologically effective amount of the compound of claim 1.

9. A method of inducing vasodilation in a mammal in need thereof, comprising the step of administering to said mammal a pharmacologically effective amount of the compound of claim 1.

10. A method of treating hypertension in a mammal in need thereof, comprising the step of administering to said mammal a pharmacologically effective amount of the compound of claim 1.

11. A method of inducing diuresis in a mammal in need thereof, comprising the step of administering to said mammal a pharmacologically effective amount of the compound of claim 1.

12. A method of inhibiting platelet agglutination in a mammal in need thereof, comprising the step of administering to said mammal a pharmacologically effective amount of the compound of claim 1.

* * * * *

UNITED STATES PATENT AND TRADEMARK OFFICE
CERTIFICATE OF CORRECTION

PATENT NO. : 5,686,454

DATED : 11/11/97

INVENTOR(S) : Marck G. Bock, et al

It is certified that error appears in the above-identified patent and that said Letters Patent is hereby corrected as shown below: On the title page: Item [54] and Column 1, line 1, delete "CAMPHORCARBONYL" and add in its place -- SUBSTITUTED AMIDE DERIVATIVES OF PIPERAZINYLCAMPHOR CARBONYL OXYTOCIN ANTAGONISTS --.

Signed and Sealed this

Twenty-third Day of June, 1998

Attest:

BRUCE LEHMAN

Attesting Officer

Commissioner of Patents and Trademarks